US011498933B2

(12) United States Patent
Rannard et al.

(10) Patent No.: US 11,498,933 B2
(45) Date of Patent: Nov. 15, 2022

(54) PRODRUG COMPOSITIONS

(71) Applicants: The University of Liverpool, Liverpool (GB); The Johns Hopkins University, Baltimore, MD (US)

(72) Inventors: Steven Paul Rannard, Liverpool (GB); Andrew Owen, Liverpool (GB); Paul Curley, Liverpool (GB); James Hobson, Liverpool (GB); Marco Siccardi, Liverpool (GB); Caren L. Freel Meyers, Baltimore, MD (US); Amer Al-Khouja, Baltimore, MD (US); David J. Meyers, Baltimore, MD (US); Charles Williams Flexner, Baltimore, MD (US)

(73) Assignees: The John Hopkins University, Baltimore, MD (US); The University of Liverpool

( * ) Notice: Subject to any disclaimer, the term of this patent is extended or adjusted under 35 U.S.C. 154(b) by 0 days.

(21) Appl. No.: 16/499,650

(22) PCT Filed: Mar. 29, 2018

(86) PCT No.: PCT/GB2018/050888
§ 371 (c)(1),
(2) Date: Sep. 30, 2019

(87) PCT Pub. No.: WO2018/178722
PCT Pub. Date: Oct. 4, 2018

(65) Prior Publication Data
US 2020/0040015 A1 Feb. 6, 2020

Related U.S. Application Data

(60) Provisional application No. 62/479,581, filed on Mar. 31, 2017.

(51) Int. Cl.
*A61K 9/16* (2006.01)
*C07D 411/04* (2006.01)
*A61K 9/00* (2006.01)
*C07F 7/18* (2006.01)
*C07F 9/6561* (2006.01)

(52) U.S. Cl.
CPC .......... *C07F 7/1804* (2013.01); *A61K 9/1635* (2013.01); *A61K 9/1641* (2013.01); *A61K 9/1652* (2013.01); *C07D 411/04* (2013.01); *C07F 9/65616* (2013.01); *A61K 9/0019* (2013.01)

(58) Field of Classification Search
None
See application file for complete search history.

(56) References Cited

U.S. PATENT DOCUMENTS

| 5,210,085 A | 5/1993 | Liotta et al. |
| 6,350,753 B1 | 2/2002 | Belleau et al. |
| 2003/0013880 A1 | 1/2003 | Murthy et al. |
| 2014/0220140 A1 | 8/2014 | Giardiello |
| 2014/0288025 A1 | 9/2014 | Milne et al. |

FOREIGN PATENT DOCUMENTS

| CN | 1465574 A | 1/2004 |
| CN | 1465582 A | 1/2004 |
| CN | 101450954 A | 6/2009 |
| EP | 0382526 A2 | 8/1990 |
| WO | 1991011186 A1 | 8/1991 |
| WO | 2011083484 A2 | 7/2011 |
| WO | 2013090420 A2 | 6/2013 |
| WO | 2016057866 A1 | 4/2016 |

OTHER PUBLICATIONS

International Search Report and Written Opinion for Application No. PCT/GB2018/050888 dated Jun. 26, 2018 (20 pages).
International Preliminary Report on Patentability for Application No. PCT/GB2018/050888 dated Jun. 26, 2018 (20 pages).
Anastasi et al., "Potent Nonclassical Nucleoside Antiviral Drugs Based on the N,N-Diarylformamidine Concept," J. Med Chem., 2004, 47:1183-1192.
STN Chemical Abstracts record for Li et al., "Preparation of nucleotide analogs as antiviral agents," CN 101450954 A, Jan. 4, 2009.
STN Chemical Abstracts record for Li et al., "Preparation of nucleotide analogs as antiviral agents and antitumor agents," CN 1465582 A, Jan. 13, 2004.
Jeong et al., "Asymmetric synthesis and biological evaluation of .beta.-L-(2R,5S)- and .alpha.-L-(2R,5R)-1,3-oxathiolane-pyrimidine and -purine nucleosides as potential anti-HIV agents," 1993, J. of Medicinal Chemistry, 36(2):181-195.
STN Chemical Abstracts record for Vorbrüggen et al., "Synthesis of Nucleosides," 2000, Organic Reactions, 1-2.
STN Chemical Abstracts record for Xue et al., "Preparation of lamivudine palmitate solid lipid nanoparticles," 2003, Dis Junyi Daxue Xuebao Bianjibu, 24(10):890-892.
Alferiev et al., "Nanoparticle-mediated delivery of a rapidly activatable prodrug of SN-38 for neuroblastoma therapy," Biomaterials, 2015, 51:22-29.
Anastasi et al., "Are 50-0-Carbamate-20,30-dideoxythiacytidine New Anti-HIV and Anti-HBV Nucleoside Drugs or Prodrugs?," Bioorganic & Medicinal Chemistry Letters, 2003, 2459-2463.
Van Heerden et al., "Synthesis and In Vitro Transdermal Penetration of Methoxypol y(ethylene glycol) Carbonate and Carbamate Derivatives of Lamivudine (3TC)," Medicinal Chemistry, 2010, 6(2):91-99.
Vasilyeva et al., "Conjugates of phosphorylated zalcitabine and lamivudine with Si02 nanoparticles: Synthesis by CuAAC click chemistry and preliminary assessment of anti-HIV and anti proliferative activity", Bioorganic & Medicinal Chemistry, 2017, 25(5):1696-1702.

(Continued)

*Primary Examiner* — Bong-Sook Baek
(74) *Attorney, Agent, or Firm* — Michael Best & Friedrich LLP

(57) ABSTRACT

The present invention provides a composition comprising nanoparticles of prodrugs of certain pharmaceutically active agents, wherein the nanoparticles of prodrugs are dispersed within a carrier material. The present invention further provides processes for the making of the same.

18 Claims, 20 Drawing Sheets

(56) References Cited

OTHER PUBLICATIONS

Caso et al., "Highly Stereoselective Synthesis of Lamivudine (3TC) and Emtricitabine (FTC) by a Novel N-Glycosidation Procedure," Organic Letters, 2015, 17(11):2626-2629.

Jeong et al., "Structure-activity relationships of beta.-D-(2S, 5R)- and .alpha.-D-(2S,5S)-1,3-oxathiolanyl nucleosides as potential anti-HIV agents," 1993, J. of Medicinal Chemistry, 36(18):2627-2638.

STN Chemical Abstracts record for Gendelman et al., "Compositions and Methods for the Delivery of Therapeutics," WO 2016057866 A1, Jan. 3, 2016.

Ramanathan et al., "Biophysical characterization of small molecule antiviral-loaded nanolipogels for HIV-1 chemoprophylaxis and topical mucosal application," 2016, Acta Biomaterialia, 36:122-131.

Date et al., "A review of nanotechnological approaches for the prophylaxis of HIV/AIDS," 2013, Biomaterials, 34:6202-6228.

Sosnik et al., "Challenges in oral drug delivery of antiretrovirals and the innovative strategies to overcome them," 2016, Advanced Drug Delivery Reviews, 103:105-120.

Nayak et al., "Lymphatic Delivery of Anti-HIV Drug Nanoparticles," 2016, Recent Patents on Nanotechnology, 10(2):116-127.

Hari et al., "Engineered nanoparticles of Efavirenz using methacrylate co-polymer (Eudragit-E100) and its biological effects in-vivo," 2016, Materials Science and Engineering C, 67:522-532.

European Patent Office Examination Report for Application No. 18715947.0 dated Feb. 9, 2021 (6 pages).

Al-Khouja et al., "Development of Prodrug Approaches for Long-Acting Nanoformulations of Emtricitabine-Based Regimens," The Johns Hopkins University, publicly disclosed May 14, 2016 (1 page).

Guo et al., "Creation of a Long-Acting Nanoformulated 2',3'-Dideoxy-3'-Thiacytidine," 2017, J Acquir Immune Defic Syndr, 74(3):e75-e83.

Xue, K.-C et al. Preparation of Lamivudyl Palmitate Solid Lipid Nanoparticles. J. Fourth Mil. Med. Univ. China 2003 vol. 24 No. 10 890-892 (with English abstract).

Gallarate, M., et al. "Preparation of solid lipid nanoparticles from W/O/W emulsions: Preliminary studies on insulin encapsulation." Journal of microencapsulation 26.5 (2009): 394-402.

China National Intellectual Property Administration. Notification of the First Office Action dated Dec. 29, 2021 with English translation (15 pages).

Japan Patent Office. Office Action for application 2019-553534 dated Feb. 1, 2022 with translation (8 pages).

IP India. Office Action for application 201917042992, dated Sep. 24, 2021 (6 pages).

| Prodrug compound | IUPAC name | Structure | Yield and NMR data | Melting point (°C) |
|---|---|---|---|---|
| 1 | methyl (5-fluoro-1-((2R,5S)-2-(((methoxycarbonyl)oxy)methyl)-1,3-oxathiolan-5-yl)-2-oxo-1,2-dihydropyrimidin-4-yl)carbamate | 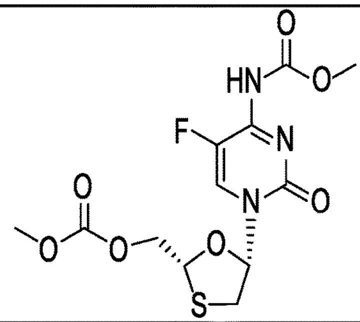 | Yield 68%. $^1$H NMR (500 MHz, CD$_3$OD) δ ppm 3.34 (br. s., 1 H) 3.63 (dd, J=12.50, 5.27 Hz, 1 H) 3.77 - 3.84 (m, 6 H) 4.54 - 4.70 (m, 2 H) 5.49 (br. s., 1 H) 6.26 (br. s., 1 H) 8.33 (d, J=6.45 Hz, 1 H) | 97-103 |
| 2 | ethyl (1-((2R,5S)-2-(((ethoxycarbonyl)oxy)methyl)-1,3-oxathiolan-5-yl)-5-fluoro-2-oxo-1,2-dihydropyrimidin-4-yl)carbamate | 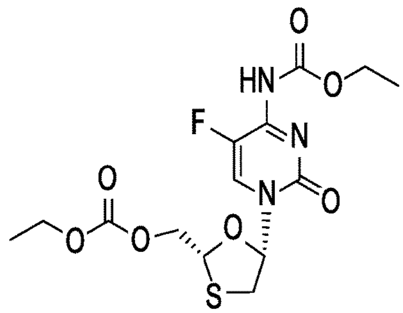 | Yield 89%. $^1$H NMR (500 MHz, CDCl$_3$) δ ppm 1.30 - 1.39 (m, 6 H) 3.21 (d, J=10.38 Hz, 1 H) 3.53 (d, J=6.92 Hz, 1 H) 4.25 (q, J=7.07 Hz, 4 H) 4.57 (br. s., 2 H) 5.39 (t, J=3.22 Hz, 1 H) 6.31 (br. s., 1 H) 8.01 (br. s., 1 H) 12.08 (br. s., 1 H) | - |
| 3 | propyl (5-fluoro-2-oxo-1-((2R,5S)-2-(((propoxycarbonyl)oxy)methyl)-1,3-oxathiolan-5-yl)-1,2-dihydropyrimidin-4-yl)carbamate | 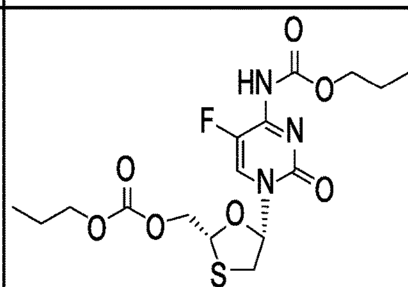 | Yield 88%. $^1$H NMR (500 MHz, CDCl$_3$) δ ppm 0.98 (dt, J=11.00, 7.47 Hz, 6 H) 1.66 - 1.81 (m, 4 H) 3.21 (d, J=10.22 Hz, 1 H) 3.54 (br. s., 1 H) 4.16 (t, J=6.45 Hz, 4 H) 4.57 (br. s., 2 H) 5.39 (br. s., 1 H) 6.31 (br. s., 1 H) 8.02 (br. s., 1 H) 12.10 (br. s., 1 H) | 102-107 |
| 4 | butyl (1-((2R,5S)-2-(((butoxycarbonyl)oxy)methyl)-1,3-oxathiolan-5-yl)-5-fluoro-2-oxo-1,2-dihydropyrimidin-4-yl)carbamate | 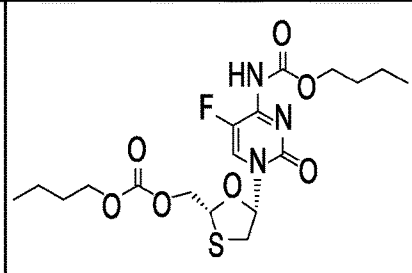 | Yield 95%. $^1$H NMR (500 MHz, CDCl$_3$) δ ppm 0.94 (td, J=7.39, 2.20 Hz, 6 H) 1.41 (tq, J=14.72, 7.43 Hz, 4 H) 3.20 (d, J=9.59 Hz, 1 H) 3.53 (d, J=9.60 Hz, 1 H) 4.19 (t, J=6.68 Hz, 4 H) 4.56 (br. s., 2 H) 5.39 (t, J=3.22 Hz, 1 H) 6.30 (br. s., 1 H) 8.00 (br. s., 1 H) 12.09 (br. s., 1 H) | - |

*Fig.1*

| Prodrug compound | IUPAC name | Structure | Yield and NMR data | Melting point (°C) |
|---|---|---|---|---|
| 5 | pentyl (5-fluoro-2-oxo-1-((2R,5S)-2-((((pentyloxy)carbonyl)oxy)methyl)-1,3-oxathiolan-5-yl)-1,2-dihydropyrimidin-4-yl)carbamate | 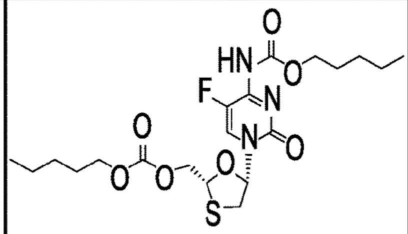 | Yield 90%. ¹H NMR (500 MHz, CDCl₃) δ ppm 0.83 - 0.98 (m, 6 H) 1.29 - 1.44 (m, 8 H) 1.62 - 1.77 (m, 4 H) 3.20 (d, J=10.38 Hz, 1 H) 3.53 (d, J=7.39 Hz, 1 H) 4.15 - 4.29 (m, 4 H) 4.56 (br. s., 2 H) 5.39 (t, J=3.22 Hz, 1 H) 6.30 (br. s., 1 H) 7.99 (br. s., 1 H) 12.10 (br. s., 1 H) | 103-106 |
| 6 | hexyl (5-fluoro-1-((2R,5S)-2-((((hexyloxy)carbonyl)oxy)methyl)-1,3-oxathiolan-5-yl)-2-oxo-1,2-dihydropyrimidin-4-yl)carbamate | 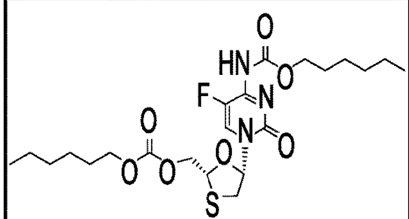 | Yield 95%. ¹H NMR (500 MHz, CDCl₃) δ ppm 0.78 - 0.97 (m, 6 H) 1.21 - 1.45 (m, 12 H) 1.60 - 1.74 (m, 4 H) 3.19 (d, J=9.90 Hz, 1 H) 3.53 (br. s., 1 H) 4.18 (t, J=6.68 Hz, 4 H) 4.47 - 4.69 (m, 2 H) 5.38 (t, J=3.22 Hz, 1 H) 6.30 (br. s., 1 H) 7.99 (br. s., 1 H) 12.09 (br. s., 1 H) | 110 |
| 7 | heptyl (5-fluoro-1-((2R,5S)-2-((((heptyloxy)carbonyl)oxy)methyl)-1,3-oxathiolan-5-yl)-2-oxo-1,2-dihydropyrimidin-4-yl)carbamate | 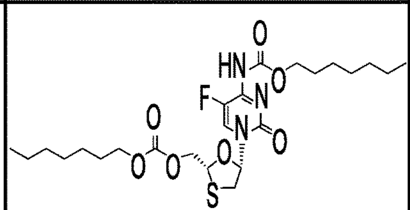 | Yield 99%. ¹H NMR (500 MHz, CDCl₃) δ ppm 0.82 - 0.95 (m, 6 H) 1.18 - 1.43 (m, 16 H) 1.66 - 1.75 (m, 4 H) 3.20 (br. s., 1 H) 3.53 (br. s., 1 H) 4.16 (t, J=6.30 Hz, 4 H) 4.56 (br. s., 2 H) 5.38 (t, J=3.30 Hz, 1 H) 6.30 (br. s., 1 H) 7.99 (br. s., 1 H) 12.09 (br. s., 1 H) | - |

*Fig. 1 (continued)*

| Prodrug compound | IUPAC name | Structure | Yield and NMR data | Melting point (°C) |
|---|---|---|---|---|
| 8 | octyl (5-fluoro-1-((2R,5S)-2-(((((octyloxy)carbonyl)oxy)methyl)-1,3-oxathiolan-5-yl)-2-oxo-1,2-dihydropyrimidin-4-yl)carbamate | 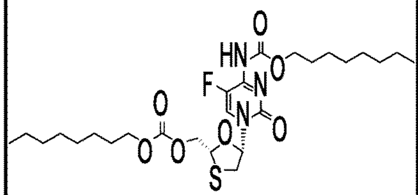 | Yield 89%. $^1$H NMR (500 MHz, CDCl$_3$) δ ppm 0.88 (t, $J$=1.00 Hz, 6 H) 1.21 - 1.42 (m, 20 H) 1.66 - 1.73 (m, 4 H) 3.19 (d, $J$=10.38 Hz, 1 H) 3.53 (d, $J$=6.60 Hz, 1 H) 4.18 (t, $J$=6.40 Hz, 4 H) 4.56 (br. s., 2 H) 5.39 (t, $J$=3.22 Hz, 1 H) 6.30 (br. s., 1 H) 7.99 (br. s., 1 H) 12.10 (br. s., 1 H) | 216-218 |
| 9 | methyl (5-fluoro-1-((2R,5S)-2-(hydroxymethyl)-1,3-oxathiolan-5-yl)-2-oxo-1,2-dihydropyrimidin-4-yl)carbamate | 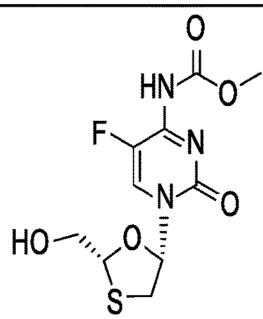 | Yield 58%. $^1$H NMR (500 MHz, CD$_3$OD) δ ppm 3.27 - 3.30 (m, 1 H) 3.61 (dd, $J$=12.58, 5.34 Hz, 1 H) 3.80 (s, 3 H) 3.90 (dd, $J$=12.81, 3.07 Hz, 1 H) 4.08 (dd, $J$=12.80, 2.80 Hz, 1 H) 5.33 (t, $J$=2.91 Hz, 1 H) 6.22 - 6.27 (m, 1 H) 8.79 (d, $J$=6.76 Hz, 1 H) | 85-89 |
| 10 | ethyl (5-fluoro-1-((2R,5S)-2-(hydroxymethyl)-1,3-oxathiolan-5-yl)-2-oxo-1,2-dihydropyrimidin-4-yl)carbamate | 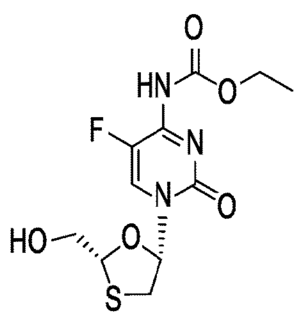 | Yield 59%. $^1$H NMR (500 MHz, CD$_3$OD) δ ppm 1.32 (t, $J$=7.15 Hz, 3 H) 3.29 (dd, $J$=12.58, 2.83 Hz, 1 H) 3.60 (dd, $J$=12.42, 5.34 Hz, 1 H) 3.90 (dd, $J$=12.73, 3.14 Hz, 1 H) 4.07 (dd, $J$=12.81, 2.91 Hz, 1 H) 4.24 (q, $J$=7.07 Hz, 2 H) 5.32 (t, $J$=2.99 Hz, 1 H) 6.24 (ddd, $J$=4.95, 2.91, 1.57 Hz, 1 H) 8.70 (d, $J$=6.76 Hz, 1 H) | - |

*Fig. 1 (continued)*

| Prodrug compound | IUPAC name | Structure | Yield and NMR data | Melting point (°C) |
|---|---|---|---|---|
| 11 | propyl (5-fluoro-1-((2R,5S)-2-(hydroxymethyl)-1,3-oxathiolan-5-yl)-2-oxo-1,2-dihydropyrimidin-4-yl)carbamate | 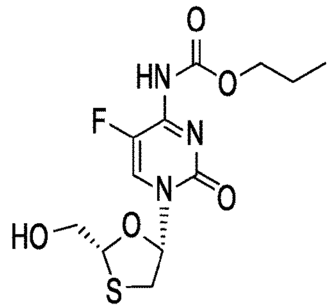 | Yield 46%. $^1$H NMR (500 MHz, CD$_3$OD) δ ppm 0.99 (t, J=7.47 Hz, 3 H) 1.72 (sxt, J=7.14 Hz, 2 H) 3.26 - 3.30 (m, 1 H) 3.61 (dd, J=12.58, 5.19 Hz, 1 H) 3.90 (dd, J=12.89, 2.99 Hz, 1 H) 4.08 (dd, J=12.81, 2.59 Hz, 1 H) 4.16 (t, J=6.68 Hz, 2 H) 5.33 (t, J=2.91 Hz, 1 H) 6.24 (dt, J=3.07, 1.77 Hz, 1 H) 8.79 (br. s., 1 H) | 82-86 |
| 12 | butyl (5-fluoro-1-((2R,5S)-2-(hydroxymethyl)-1,3-oxathiolan-5-yl)-2-oxo-1,2-dihydropyrimidin-4-yl)carbamate | 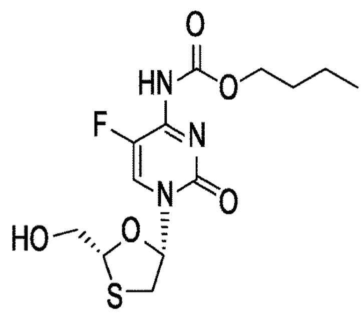 | Yield 58%. $^1$H NMR (500 MHz, CDCl$_3$) ppm 0.89 (t, J=7.23 Hz, 3 H) 1.28 - 1.46 (m, 2 H) 1.53 - 1.72 (m, 2 H) 3.22 (d, J=12.26 Hz, 1 H) 3.48 (d, J=12.30 Hz, 1 H) 3.97 (d, J=11.00 Hz, 1 H) 4.06 - 4.26 (m, 3 H) 5.27 (br. s., 1 H) 6.20 (br. s., 1 H) 8.55 (br. s., 1 H) 11.97 (br. s., 1 H) | 47 |
| 13 | pentyl (5-fluoro-1-((2R,5S)-2-(hydroxymethyl)-1,3-oxathiolan-5-yl)-2-oxo-1,2-dihydropyrimidin-4-yl)carbamate | 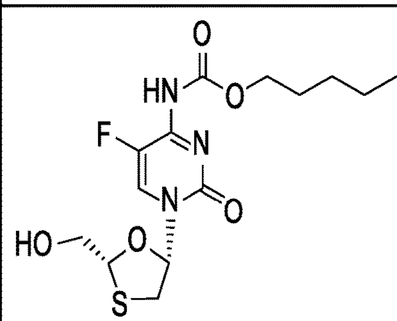 | Yield 98%. $^1$H NMR (500 MHz, CDCl$_3$) δ ppm 0.86 - 0.92 (m, 3 H) 1.26 - 1.42 (m, 4 H) 1.68 (quin, J=7.03 Hz, 2 H) 3.24 (dd, J=12.58, 2.83 Hz, 1 H) 3.51 (br. s., 1 H) 3.91 - 4.06 (m, 1 H) 4.09 - 4.26 (m, 3 H) 5.30 (t, J=2.52 Hz, 1 H) 6.24 (ddd, J=4.99, 3.10, 1.34 Hz, 1 H) 8.52 (br. s., 1 H) 12.09 (br. s., 1 H) | 44-47 |

*Fig. 1* (continued)

| Prodrug compound | IUPAC name | Structure | Yield and NMR data | Melting point (°C) |
|---|---|---|---|---|
| 14 | hexyl (5-fluoro-1-((2R,5S)-2-(hydroxymethyl)-1,3-oxathiolan-5-yl)-2-oxo-1,2-dihydropyrimidin-4-yl)carbamate | 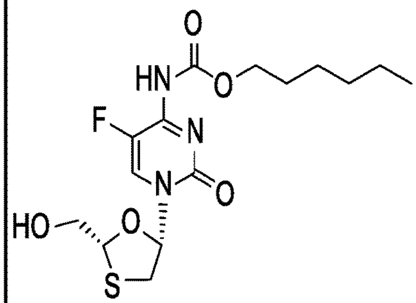 | Yield 64%. $^1$H NMR (500 MHz, CDCl$_3$) δ ppm 0.90 (t, J=7.00 Hz, 3 H) 1.26 - 1.47 (m, 6 H) 1.70 (quin, J=7.00 Hz, 2 H) 3.21 (d, J=11.16 Hz, 1 H) 3.52 (d, J=8.02 Hz, 1 H) 3.97 (d, J=12.10 Hz, 1 H) 4.17 (br. s., 3 H) 5.33 (br. s., 1 H) 6.30 (t, J=3.85 Hz, 1 H) 8.25 (br. s., 1 H) 12.11 (br. s., 1 H) | 46-49 |
| 15 | heptyl (5-fluoro-1-((2R,5S)-2-(hydroxymethyl)-1,3-oxathiolan-5-yl)-2-oxo-1,2-dihydropyrimidin-4-yl)carbamate | 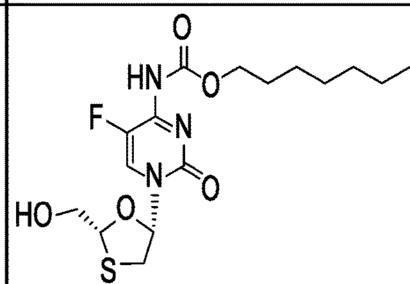 | Yield 67%. $^1$H NMR (500 MHz, CDCl$_3$) δ ppm 0.85 (t, J=7.00 Hz, 3 H) 1.16 - 1.41 (m, 8 H) 1.65 (quin, J=6.50 Hz, 2 H) 3.23 (dd, J=12.65, 2.75 Hz, 1 H) 3.50 (d, J=7.70 Hz, 1 H) 3.98 (dd, J=12.89, 2.83 Hz, 1 H) 4.08 - 4.24 (m, 3 H) 5.28 (t, J=2.59 Hz, 1 H) 6.17 - 6.29 (m, 1 H) 8.55 (br. s., 1 H) 12.07 (br. s., 1 H) | 46 |
| 16 | octyl (5-fluoro-1-((2R,5S)-2-(hydroxymethyl)-1,3-oxathiolan-5-yl)-2-oxo-1,2-dihydropyrimidin-4-yl)carbamate | 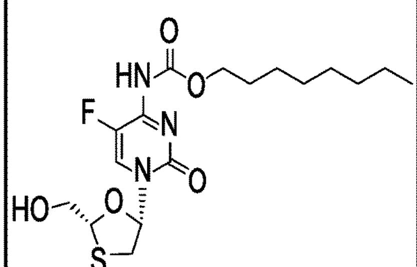 | Yield 81%. $^1$H NMR (500 MHz, CDCl$_3$) δ ppm 0.82 (t, J=6.60 Hz, 3 H) 1.16 - 1.37 (m, 10 H) 1.56 - 1.69 (m, 2 H) 3.20 (dd, J=12.42, 1.73 Hz, 1 H) 3.47 (d, J=8.17 Hz, 1 H) 3.95 (dd, J=12.58, 1.57 Hz, 1 H) 4.08 - 4.21 (m, 3 H) 5.26 (br. s., 1 H) 6.19 (br. s., 1 H) 8.55 (br. s., 1 H) 12.03 (br. s., 1 H) | 41-44 |

*Fig. 1 (continued)*

| Prodrug compound | IUPAC name | Structure | Yield and NMR data | Melting point (°C) |
|---|---|---|---|---|
| 17 | ((2R,5S)-5-(5-fluoro-2-oxo-4-(((pentyloxy)carbonyl)amino)pyrimidin-1(2H)-yl)-1,3-oxathiolan-2-yl)methyl acetate | 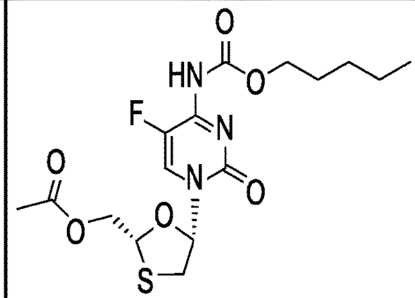 | Yield 91%. $^1$H NMR (500 MHz, CDCl$_3$) δ ppm 0.85 (t, J=6.90 Hz, 3 H) 1.24 - 1.38 (m, 4 H) 1.65 (quin, J=7.00 Hz, 2 H) 2.12 (s, 3 H) 3.22 (d, J=12.26 Hz, 1 H) 3.50 - 3.60 (m, 1 H) 4.13 (br. s., 2 H) 4.43 (dd, J=12.73, 2.67 Hz, 1 H) 4.58 (d, J=9.59 Hz, 1 H) 5.35 (dd, J=3.77, 2.99 Hz, 1 H) 6.24 (br. s., 1 H) 8.03 (br. s., 1 H) 12.03 (br. s., 1 H) | - |
| 18 | ((2R,5S)-5-(5-fluoro-4-(((hexyloxy)carbonyl)amino)-2-oxopyrimidin-1(2H)-yl)-1,3-oxathiolan-2-yl)methyl acetate | 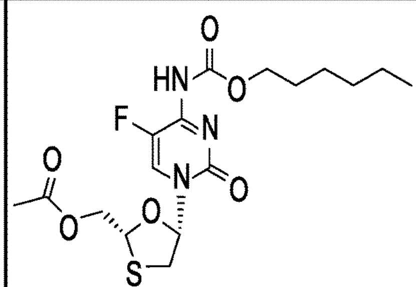 | Yield 74%. $^1$H NMR (500 MHz, CDCl$_3$) δ ppm 0.80 (t, J=6.90 Hz, 3 H) 1.11 - 1.39 (m, 6 H) 1.60 (quin, J=7.20 Hz, 2 H) 2.07 (s, 3 H) 3.19 (dd, J=12.73, 2.36 Hz, 1 H) 3.51 (dd, J=12.65, 5.27 Hz, 1 H) 4.08 (t, J=6.45 Hz, 2 H) 4.39 (dd, J=12.73, 2.67 Hz, 1 H) 4.54 (d, J=10.85 Hz, 1 H) 5.32 (t, J=3.38 Hz, 1 H) 6.20 (br. s., 1 H) 8.03 (br. s., 1 H) 11.96 (br. s., 1 H) | 64-67 |
| 19 | ((2R,5S)-5-(5-fluoro-4-(((heptyloxy)carbonyl)amino)-2-oxopyrimidin-1(2H)-yl)-1,3-oxathiolan-2-yl)methyl acetate | 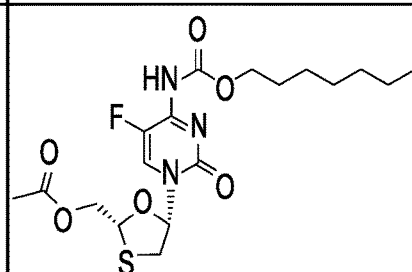 | Yield 74%. $^1$H NMR (500 MHz, CDCl$_3$) δ ppm 0.89 (t, J=6.68 Hz, 3 H) 1.19 - 1.47 (m, 8 H) 1.71 (quin, J=7.11 Hz, 2 H) 2.17 (s, 3 H) 3.24 (d, J=12.42 Hz, 1 H) 3.57 (dd, J=12.73, 5.34 Hz, 1 H) 4.19 (t, J=6.60 Hz, 2 H) 4.48 (dd, J=12.65, 2.44 Hz, 1 H) 4.63 (dd, J=12.65, 3.69 Hz, 1 H) 5.38 (t, J=3.22 Hz, 1 H) 6.29 (br. s., 1 H) 8.08 (br. s., 1 H) 12.10 (br. S., 1 H) | 54 |

*Fig. 1* (continued)

| Prodrug compound | IUPAC name | Structure | Yield and NMR data | Melting point (°C) |
|---|---|---|---|---|
| 20 | ((2R,5S)-5-(5-fluoro-4-(((octyloxy)carbonyl)amino)-2-oxopyrimidin-1(2H)-yl)-1,3-oxathiolan-2-yl)methyl acetate | 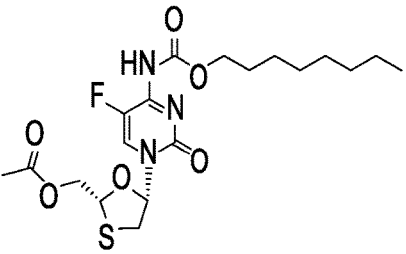 | Yield 69%. ¹H NMR (500 MHz, CDCl₃) δ ppm 0.83 (t, J=6.90 Hz, 3 H) 1.12 - 1.41 (m, 10 H) 1.65 (quin, J=7.10 Hz, 2 H) 2.12 (s, 3 H) 3.22 (d, J=12.26 Hz, 1 H) 3.54 (dd, J=12.18, 4.95 Hz, 1 H) 4.13 (br. s., 2 H) 4.43 (dd, J=12.65, 2.59 Hz, 1 H) 4.58 (d, J=11.32 Hz, 1 H) 5.35 (dd, J=3.77, 2.99 Hz, 1 H) 6.24 (br. s., 1 H) 7.95 (br. s, 1 H) 12.02 (br. s., 1 H) | 48 |
| 21 | ((2R,5S)-5-(5-fluoro-4-(((octyloxy)carbonyl)amino)-2-oxopyrimidin-1(2H)-yl)-1,3-oxathiolan-2-yl)methyl isobutyrate | 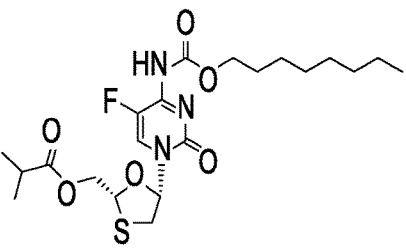 | Yield 22%. ¹H NMR (500 MHz, CDCl₃) δ ppm 0.88 (t, J=6.68 Hz, 3 H) 1.22 (d, J=6.92 Hz, 6 H) 1.25 - 1.38 (m, 10 H) 1.70 (quin, J=7.20 Hz, 2 H) 2.65 (dt, J=13.99, 7.00 Hz, 1 H) 3.21 (d, J=10.85 Hz, 1 H) 3.56 (d, J=7.86 Hz, 1 H) 4.17 (d, J=5.50 Hz, 2 H) 4.45 (dd, J=12.73, 2.20 Hz, 1 H) 4.63 (d, J=10.85 Hz, 1 H) 5.38 (br. s., 1 H) 6.28 (br. s., 1 H) 8.01 (br. s., 1 H) 12.10 (br. s., 1 H) | - |
| 22 | ((2R,5S)-5-(5-fluoro-2-oxo-4-(((pentyloxy)carbonyl)aminopyrimidin-1(2H)-yl)-1,3-oxathiolan-2-yl)methyl butyrate | 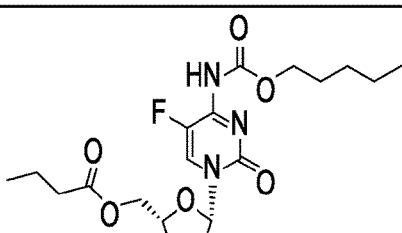 | Yield 97%. ¹H NMR (500 MHz, CDCl₃) δ ppm 0.91 (t, J=7.00 Hz, 3 H) 0.98 (t, J=7.39 Hz, 3 H) 1.34 - 1.44 (m, 4 H) 1.65 - 1.78 (m, 4 H) 2.41 (t, J=7.47 Hz, 2 H) 3.16 - 3.33 (m, 1 H) 3.48 - 3.69 (m, 1 H) 4.18 (br. s., 2 H) 4.47 (dd, J=12.73, 2.67 Hz, 1 H) 4.65 (d, J=13.83 Hz, 1 H) 5.38 (br. s., 1 H) 6.29 (br. s., 1 H) 8.06 (br. s., 1 H) 12.11 (br. s., 1 H) | 57-59 |

*Fig. 1* (continued)

| Prodrug compound | IUPAC name | Structure | Yield and NMR data | Melting point (°C) |
|---|---|---|---|---|
| 23 | (Z)-N'-(5-fluoro-1-((2R,5S)-2-(hydroxymethyl)-1,3-oxathiolan-5-yl)-2-oxo-1,2-dihydropyrimidin-4-yl)-N,N-dimethylformimidamide | 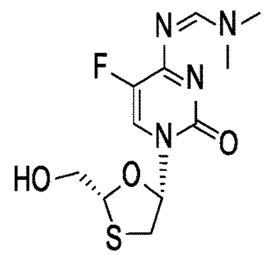 | Yield 100%. $^1$H NMR (500 MHz, CD$_3$OD, reference to TMS) δ 8.71 (s, 1H), 8.45 (d, J = 6.45 Hz, 1H), 6.26 (ddd, J = 1.65, 3.50, 5.23 Hz, 1H), 5.31 (t, J = 3.38 Hz, 1H), 4.03 (dd, J = 3.14, 12.73 Hz, 1H), 3.89 (dd, J = 3.62, 12.73 Hz, 1H), 3.57 (dd, J = 5.34, 12.26 Hz, 1H), 3.26 (s, 3H), 3.22 (dd, J = 3.38, 12.34 Hz, 1H), 3.20 (d, J = 0.63 Hz, 3H). $^{13}$C NMR (126 MHz, CD$_3$OD) 164.9, 164.8, 160.4, 156.2, 142.64 (d), 129.08 (d), 89.3 (d, J=12.7 Hz), 63.4, 42.2, 39.3, 36.0 | 159-170 |
| 24 | 2-(4-((1-((2R,5S)-2-(((tert-butyldimethylsilyl)oxy)methyl)-1,3-oxathiolan-5-yl)-5-fluoro-2-oxo-1,2-dihydropyrimidin-4-yl)amino)-2-methyl-4-oxobutan-2-yl)-3,5-dimethylphenyl acetate | 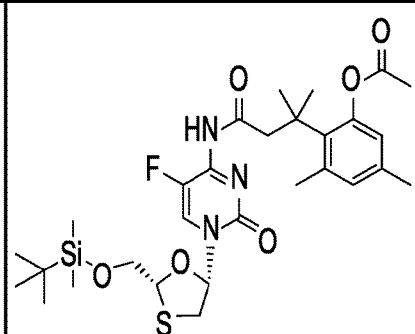 | Yield 65%. $^1$H NMR (500 MHz, CDCl$_3$) δ 8.49 (br. s., 1H), 7.73 (br. s., 1H), 6.73 - 6.87 (m, 1H), 6.49 - 6.61 (m, 1H), 6.16 - 6.33 (m, 1H), 5.25 (t, J = 2.36 Hz, 1H), 4.24 (dd, J = 2.20, 12.10 Hz, 1H), 3.94 (dd, J = 2.36, 11.95 Hz, 1H), 3.55 (dd, J = 4.24, 12.26 Hz, 1H), 3.31 - 3.46 (m, 1H), 3.07 - 3.31 (m, 2H), 2.55 (s, 3H), 2.30 (s, 3H), 2.21 (s, 3H), 1.62 (d, J = 6.13 Hz, 6H), 0.94 (s, 9H), 0.14 (s, 6H). $^{13}$C NMR (126 MHz, CDCl$_3$) 170.7, 170.4, 152.8, 152.4, 149.3, 138.2, 136.2, 133.0, 132.5, 129.4, 129.2, 123.0, 89.2, 87.4, 63.0, 51.3, 39.4, 39.2, 31.7, 25.7, 25.4, 21.8, 20.1, 18.5, -5.6 | - |

*Fig. 1* (continued)

| Prodrug compound | IUPAC name | Structure | Yield and NMR data | Melting point (°C) |
|---|---|---|---|---|
| 25 | 2-(4-((5-fluoro-1-((2R,5S)-2-(hydroxymethyl)-1,3-oxathiolan-5-yl)-2-oxo-1,2-dihydropyrimidin-4-yl)amino)-2-methyl-4-oxobutan-2-yl)-3,5-dimethylphenyl acetate | 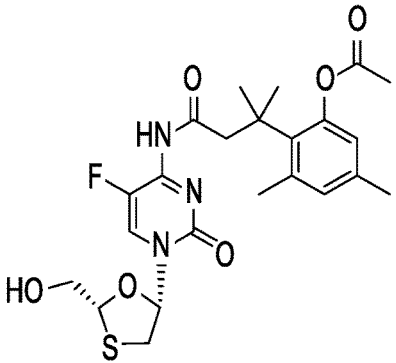 | Yield 86%. $^1$H NMR (500 MHz, CDCl$_3$) δ ppm 1.63 (d, J=4.09 Hz, 6 H) 2.22 (s, 3 H) 2.32 (s, 3 H) 2.56 (s, 3 H) 3.18 - 3.36 (m, 3 H) 3.60 (dd, J=12.50, 5.27 Hz, 1 H) 3.90 - 4.01 (m, 1 H) 3.96 (dd, J=12.73, 2.83 Hz, 1 H) 4.19 (d, J=12.10 Hz, 1 H) 5.33 (t, J=2.67 Hz, 1 H) 6.27 (td, J=3.38, 1.41 Hz, 1 H) 6.58 (s, 1 H) 6.81 (s, 1 H) 7.62 (br. s., 1 H) 8.37 (d, J=5.50 Hz, 1 H) | 76-81 |
| 26 | (2S)-isopropyl (((((R)-1-(6-(3-(2-acetoxy-4,6-dimethylphenyl)-3-methylbutanamido)-9H-purin-9-yl)propan-2-yl)oxy)methyl)(phenoxy)phosphoryl)-L-alaninate | 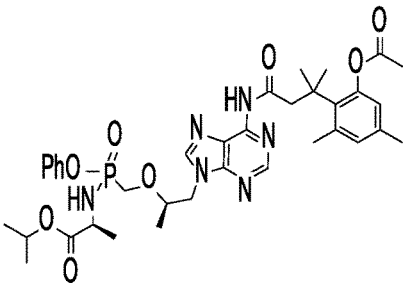 | Yield 12%. | - |

*Fig. 1 (continued)*

| Compound | Normalized velocity (nmol/h/mg) |
|---|---|
| Capecitabine | 18.7 |
| 10 (n = 1) | 0.4 |
| 11 (n = 2) | 1.5 |
| 12 (n = 3) | 12.2 |
| 13 (n = 4) | 32.1 |
| 14 (n = 5) | 51.5 |
| 15 (n = 6) | 90.8 |
| 16 (n = 7) | 64.6 |

| Compound | $K_{m, avg}$ (mM) | $V_{max, avg}$ (nmol/h/mg) | Intrinsic Clearance (µL/h/mg) |
|---|---|---|---|
| 9 (n = 0) | 11.7 ± 2.2 | 235 ± 37 | 20.1 ± 0.6 |
| 10 (n = 1) | 11.3 ± 1.8 | 179 ± 56 | 15.6 ± 2.7 |
| 11 (n = 2) | 10.8 ± 4.6 | 242 ± 103 | 22.6 ± 3.6 |
| 12 (n = 3) | 6.2 ± 0.6 | 397 ± 33 | 64.2 ± 7.8 |
| Capecitabine | 2.9 ± 1.1 | 435 ± 143 | 151.3 ± 24.3 |
| 13 (n = 4) | 2.9 ± 0.3 | 320 ± 68 | 110.4 ± 19.6 |
| 14 (n = 5) | 3.0 ± 0.5 | 605 ± 73 | 208.5 ± 36.6 |
| 15 (n = 6) | 3.7 ± 0.7 | 1048 ± 248 | 287.0 ± 27.1 |
| 16 (n = 7) | 2.7 ± 0.5 | 889 ± 169 | 328.3 ± 6.6 |

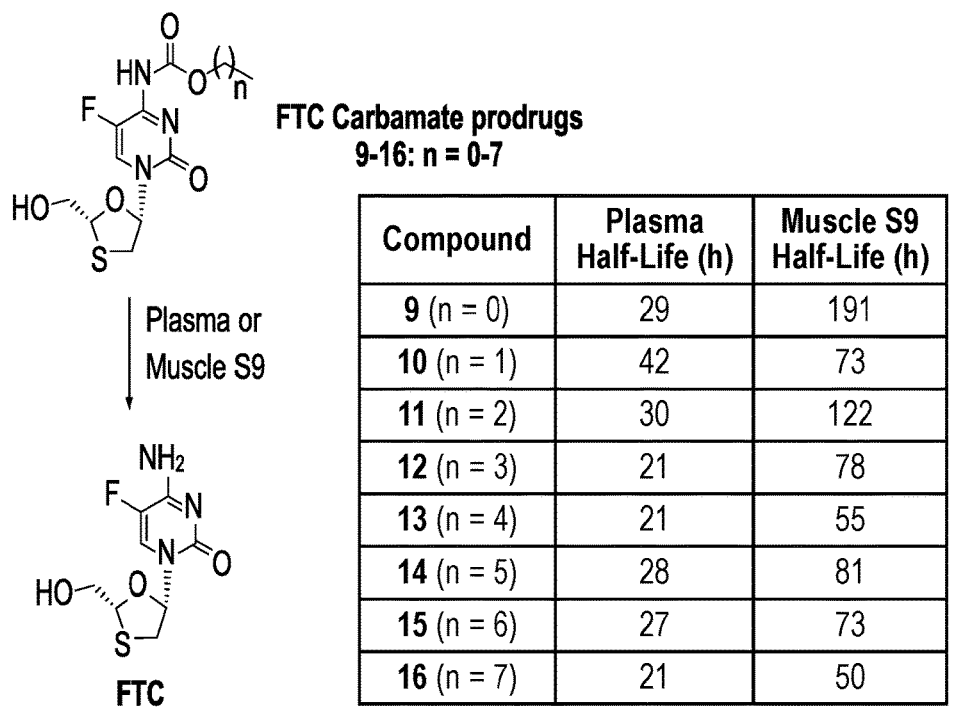
FTC Carbamate prodrugs
9-16: n = 0-7
| Compound | Plasma Half-Life (h) | Muscle S9 Half-Life (h) |
|---|---|---|
| 9 (n = 0) | 29 | 191 |
| 10 (n = 1) | 42 | 73 |
| 11 (n = 2) | 30 | 122 |
| 12 (n = 3) | 21 | 78 |
| 13 (n = 4) | 21 | 55 |
| 14 (n = 5) | 28 | 81 |
| 15 (n = 6) | 27 | 73 |
| 16 (n = 7) | 21 | 50 |
*Fig. 4*
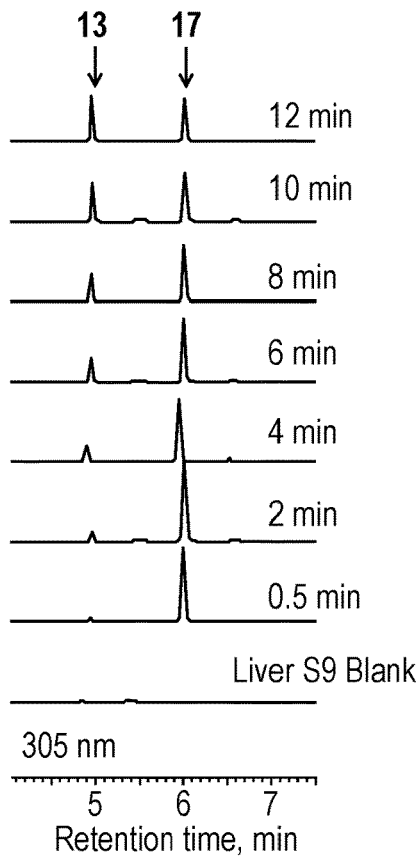
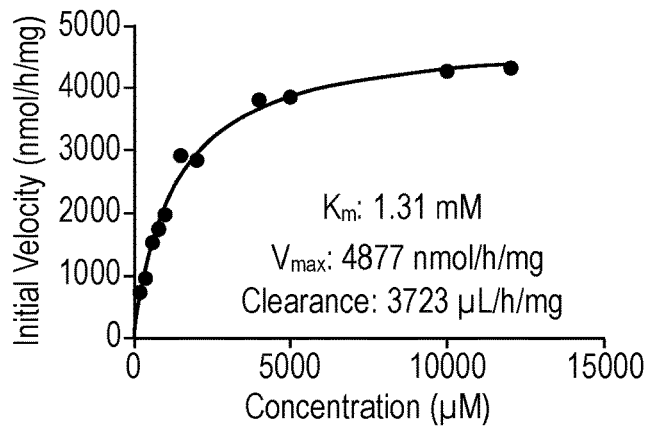
$K_m$: 1.31 mM
$V_{max}$: 4877 nmol/h/mg
Clearance: 3723 μL/h/mg
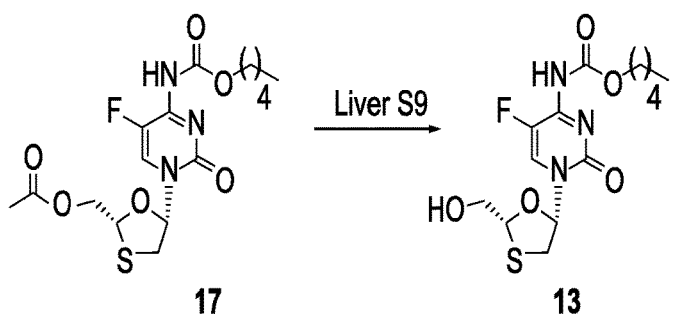
*Fig. 5*

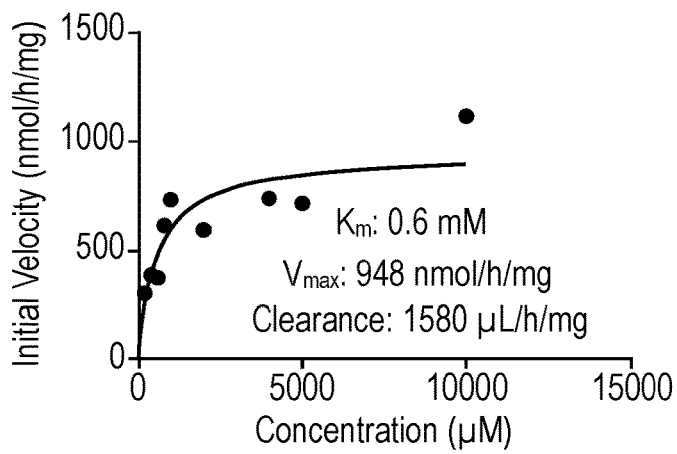
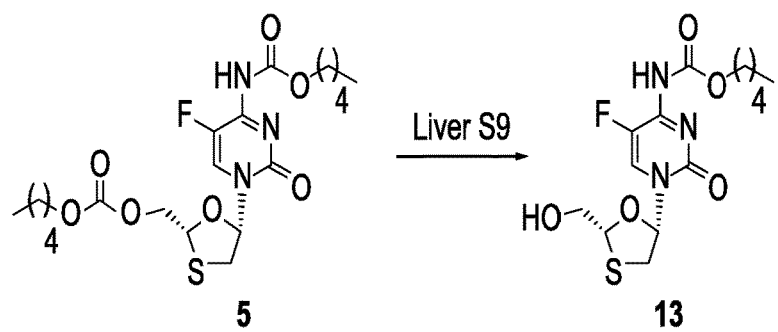
*Fig. 6*
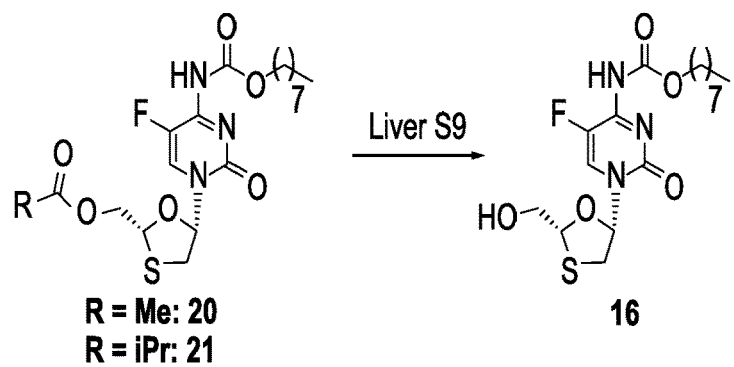
| Compound | Half-Life in Liver S9 (min) |
| --- | --- |
| 20 | 1.2 (at 1 mg/mL) |
| 21 | 1.9 (at 4 mg/mL) |
*Fig. 7*

| Prodrug | LogP |
|---|---|
| FTC | -1.11 ± 0.02 |
| 1 (n = 0) | -0.10 |
| 3 (n = 2) | 2.29 |
| 5 (n = 4) | 3.88 |
| 6 (n = 5) | 4.39 |
| 8 (n = 7) | >5 |
| 9 (n = 0) | -1.37 ± 0.03 |
| 10 (n = 1) | -0.79 ± 0.07 |
| 11 (n = 2) | -0.16 ± 0.08 |
| 12 (n = 3) | 0.67 ± 0.08 |
| 13 (n = 4) | 1.11 ± 0.07 |
| 14 (n = 5) | 1.78 ± 0.17 |
| 15 (n = 6) | 2.50 ± 0.09 |
| 16 (n = 7) | 3.15 ± 0.11 |
| 23 | -0.58 |

- FTC is not metabolized by CYP enzymes.
- Metabolite formation requires liver microsomes and NADPH.
- LC-MS suggests hydroxylated metabolite.

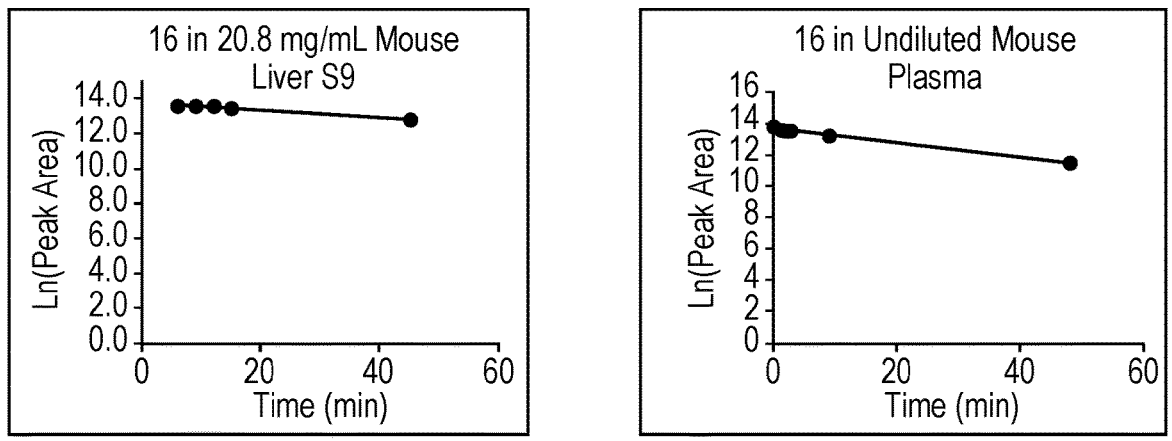
$t_{1/2}$ in 20.8 mg/mL mouse liver = 33 min
$t_{1/2}$ in 20 mg/mL human liver = 48 min
$t_{1/2}$ in undiluted mouse plasma = 74 min
$t_{1/2}$ in undiluted human plasma = 1260 min (21h)
16 hydrolysis rate:
- comparable in mouse and human liver S9
- dramatically enhanced in mouse plasma
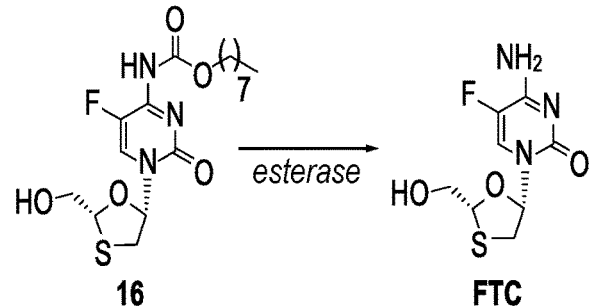
*Fig. 12*
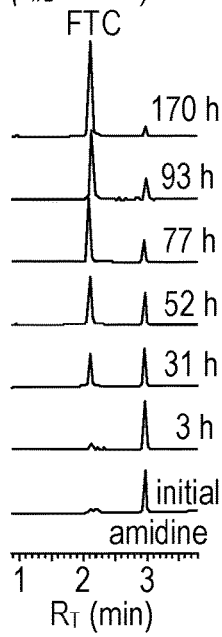
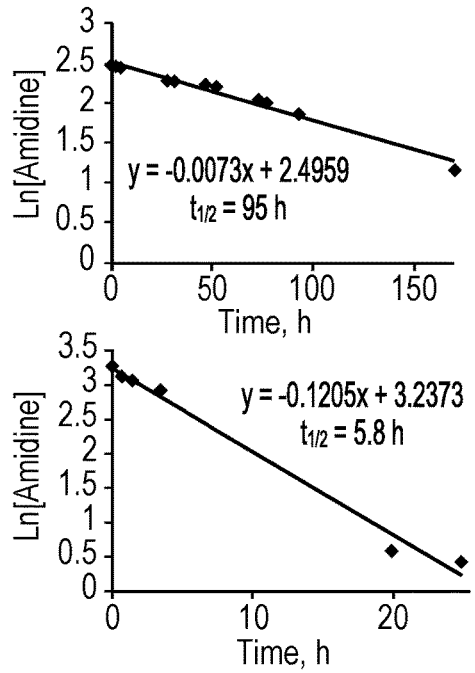
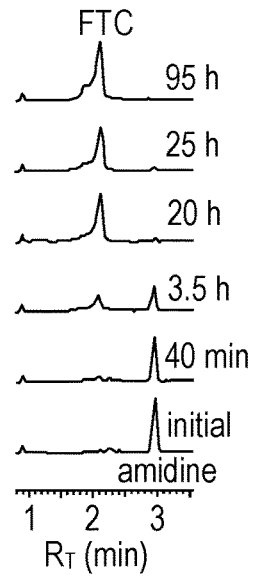
*Fig. 13*

| | F68 | PVPk30 | HPMC | PEG1K | F127 | Kollicoat | PVA | Surfactan Totals |
|---|---|---|---|---|---|---|---|---|
| TPGS | 5 | 3 | 4 | 1 | 4 | 2 | 3 | 22 |
| Tween 20 | 4 | 8 | 6 | 5 | 4 | 5 | 6 | 38 |
| Tween 80 | 4 | 4 | 4 | 4 | 7 | 3 | 6 | 32 |
| NDC | 6 | 7 | 9 | 7 | 5 | 7 | 5 | 46 |
| AOT | 4 | 5 | 5 | 6 | 4 | 4 | 5 | 33 |
| Solutol | 4 | 6 | 5 | 4 | 6 | 2 | 5 | 32 |
| Polymer Totals | 27 | 33 | 33 | 27 | 30 | 23 | 30 | 203 |

PRODRUG COMPOSITIONS

CROSS-REFERENCE TO RELATED APPLICATIONS

This patent application is the U.S. national stage entry, under 35 U.S.C. § 371, of International Application Number PCT/GB2018/050888, filed Mar. 29, 2018, which claims priority to U.S. Patent Application No. 62/479,581, filed Mar. 31, 2017, the entire contents of each of which are hereby incorporated by reference.

STATEMENT OF GOVERNMENT INTEREST

This invention was made with government support under grant number AI114405 awarded by the National Institutes of Health. The government has certain rights in the invention.

TECHNICAL FIELD

The present invention relates to a composition comprising nanoparticles of a prodrug of a pharmaceutically active agent.

BACKGROUND ART

Many solid materials with desirable biological or functional properties (herein referred to as "active agents") may be administered in various nanoparticle forms. This may be achieved via various nano-milling technologies known in the art. International patent applications published as WO2006/079409 and WO2008/006712 disclose nano-dispersion approaches for forming useful nano-formulated compositions. These approaches include forming water/solvent emulsion systems before performing a step of drying, such as freeze drying or spray-drying.

While these nano-dispersion approaches represent significant improvements over conventional grinding/milling techniques and have also been successful in providing useful long acting pharmaceutical formulations it has been discovered that such nano-dispersion approaches are incompatible with a range of useful pharmaceutically active compound classes, including some nucleoside analogues and some nucleotide analogues, which are used, inter alia, as the basis for HIV and/or cancer treatment and/or prevention. One example is the nucleoside reverse transcriptase inhibitors (NRTIs) class used in a range of disease areas, for example as antiretroviral (ARV) medications for HIV treatment and prevention. Such medications require life-long dosing which can lead to reduced patient adherence thus decreasing the chances of treatment failure. Long acting ARVs would allow for less frequent administration and, therefore, would reduce the risk of patient non-adherence. An improved approach to providing long acting ARVs is desirable, from any one or more of the points of view of reduction in dosing, ease of administration and increased patient adherence/compliance.

It is therefore an object of the present invention to obviate or mitigate the issue of pharmaceutically active compound classes demonstrating incompatibilities with the nano-dispersion approaches mentioned above.

SUMMARY OF INVENTION

In its broadest sense, the inventors propose use of prodrugs of certain pharmaceutically active agents for the treatment and/or prevention of HIV and/or cancer. The inventors in particular propose prodrug compounds of the formula (I) or pharmaceutically acceptable derivatives thereof, as defined in the claims and further described in aspects and embodiments of the invention below, for the treatment or prevention of HIV and/or cancer.

As indicated by the examples and Figures described herein, the inventors also propose to use novel prodrug compounds compatible with the nano-dispersion approaches (described above) to provide nano-formulated prodrug compositions suitable for delivering pharmaceutically active agents, which are incompatible with the prior art nano-dispersion approaches, over a prolonged period of time. This provides long acting pharmaceutical formulations which have, prior to this developmental work, been inaccessible to patients.

In an aspect of the invention there is a composition comprising nanoparticles of a prodrug compound dispersed within one or more carrier materials, wherein the log P value of the prodrug compound is at least about 1 and greater than the log P value of the pharmaceutically active agent.

In embodiments the one or more carrier materials comprise a hydrophilic polymer and/or surfactant.

In further embodiments the hydrophilic polymer is selected from the group consisting of ethylene oxide-propylene oxide block copolymers (available under the trade name Pluronics® F-68 or Pluronics® F-127), polyvinyl alcohol ('PVA'), polyvinyl alcohol-polyethylene glycol graft copolymer (available under the trade name Kollicoat™); polyethylene glycol k1 (having average $M_w$ of 1,000), hydroxylpropyl methyl cellulose (HPMC), polyvinylpyrrolidone k30 ('PVP k30') or any combination thereof.

In some embodiments the surfactant is selected from the group consisting of vitamin-E-polyethylene glycol-succinate (Vit-E-PEG-succinate, TPGS or D-α-tocopherol polyethylene glycol 1000 succinate), sodium deoxycholate (NDC), polyoxyethylene (20) sorbitan monolaurate (also known as polysorbate 20 and available under the trade name Tween™ 20), polyoxyethylene (20) sorbitan monooleate (also known as polysorbate 80 and available under the trade name Tween™ 80), dioctyl sulfosuccinate sodium salt (AOT), polyethylene glycol (15)-hydroxystearate (available under the trade name Solutol™ HS) or any combination thereof.

According to certain embodiments the one or more carrier materials are provided in any one of the following combinations:

Pluronics® F-68 AND vitamin-E-polyethylene glycol-succinate;
Pluronics® F-68 AND sodium deoxycholate;
Pluronics® F-68 AND polyoxyethylene (20) sorbitan monolaurate;
Pluronics® F-68 AND polyoxyethylene (20) sorbitan monooleate;
Pluronics® F-68 AND dioctyl sulfosuccinate sodium salt;
Pluronics® F-68 AND polyethylene glycol (15)-hydroxystearate;
Pluronics® F-127 AND vitamin-E-polyethylene glycol-succinate;
Pluronics® F-127 AND sodium deoxycholate;
Pluronics® F-127 AND polyoxyethylene (20) sorbitan monolaurate;
Pluronics® F-127 AND polyoxyethylene (20) sorbitan monooleate;
Pluronics® F-127 AND dioctyl sulfosuccinate sodium salt;
Pluronics® F-127 AND polyethylene glycol (15)-hydroxystearate;

polyvinyl alcohol AND vitamin-E-polyethylene glycol-succinate;
polyvinyl alcohol AND sodium deoxycholate;
polyvinyl alcohol AND polyoxyethylene (20) sorbitan monolaurate;
polyvinyl alcohol AND polyoxyethylene (20) sorbitan monooleate;
polyvinyl alcohol AND dioctyl sulfosuccinate sodium salt;
polyvinyl alcohol-polyethylene glycol graft copolymer AND vitamin-E-polyethylene glycol-succinate;
polyvinyl alcohol-polyethylene glycol graft copolymer AND sodium deoxycholate;
polyvinyl alcohol-polyethylene glycol graft copolymer AND polyoxyethylene (20) sorbitan monolaurate;
polyvinyl alcohol-polyethylene glycol graft copolymer AND dioctyl sulfosuccinate sodium salt;
polyethylene glycol k1 AND sodium deoxycholate;
polyethylene glycol k1 AND polyoxyethylene (20) sorbitan monolaurate;
polyethylene glycol k1 AND polyoxyethylene (20) sorbitan monooleate;
polyethylene glycol k1 AND dioctyl sulfosuccinate sodium salt;
polyethylene glycol k1 AND polyethylene glycol (15)-hydroxystearate;
hydroxylpropyl methyl cellulose AND vitamin-E-polyethylene glycol-succinate;
hydroxylpropyl methyl cellulose AND sodium deoxycholate;
hydroxylpropyl methyl cellulose AND polyoxyethylene (20) sorbitan monolaurate;
hydroxylpropyl methyl cellulose AND polyoxyethylene (20) sorbitan monooleate;
hydroxylpropyl methyl cellulose AND dioctyl sulfosuccinate sodium salt;
hydroxylpropyl methyl cellulose AND polyethylene glycol (15)-hydroxystearate;
polyvinylpyrrolidone k30 AND vitamin-E-polyethylene glycol-succinate;
polyvinylpyrrolidone k30 AND sodium deoxycholate;
polyvinylpyrrolidone k30 AND polyoxyethylene (20) sorbitan monolaurate;
polyvinylpyrrolidone k30 AND polyoxyethylene (20) sorbitan monooleate;
polyvinylpyrrolidone k30 AND dioctyl sulfosuccinate sodium salt; or
polyvinylpyrrolidone k30 AND polyethylene glycol (15)-hydroxystearate.

In yet further embodiments the one or more carrier materials are provided in any one of the following combinations:
polyvinyl alcohol AND polyoxyethylene (20) sorbitan monolaurate;
Pluronics® F-127 AND vitamin-E-polyethylene glycol-succinate; hydroxylpropyl methyl cellulose AND N alkyldimethylbenzylammonium chloride; and
hydroxylpropyl methyl cellulose AND dioctyl sulfosuccinate sodium salt.

In some embodiments the prodrug compound is as defined according to formula (I).

In other embodiments the prodrug of a pharmaceutically active agent is present in an amount of from about 10 wt % to about 90 wt % or from about 10 wt % to about 70 wt %.

In still further embodiments the prodrug compound is present in an amount of from about 25 wt % to about 50 wt % or from about 40 wt % to about 60 wt %. The composition may be a solid.

In further embodiments the nanoparticles of a prodrug compound may have a Z-average particle diameter of less than 1000 nm. The nanoparticles of a prodrug compound may have a Z-average particle diameter of from about 100 to about 800 nm or may have a Z-average particle diameter of from about 100 to about 400 nm.

In embodiments, the polydispersity of the nanoparticles of a prodrug compound may be less than 0.5 or the polydispersity of the nanoparticles of a prodrug compound may be from about 0.01 to about 0.45. In some embodiments, the polydispersity of the nanoparticles of a prodrug compound may be from about 0.1 to about 0.2.

In yet some embodiments, the log P of the prodrug compound may be from about 1 to about 10 or the log P of the prodrug compound may be from about 3 to about 8 or from about 5 to about 8.

In a second aspect of the invention there is provided a process for preparing a composition according to the first aspect, the process comprising:
(i) preparing an oil-in-water emulsion comprising:
an oil phase comprising a prodrug compound as defined herein and according to formula (I) and
an aqueous phase comprising one or more selected carrier materials, the one or more selected carrier materials being defined herein; and
(ii) removing the oil and water from the oil-in-water emulsion to form the composition.

In a third aspect of the invention there is provided a process for preparing a composition according to the first aspect, the process comprising:
(i) preparing a single phase solution comprising a prodrug compound as defined herein and according to formula (I), and one or more selected carrier materials as being defined herein, in one or more solvents; and
(ii) removing the one or more solvents to form the solid composition.

In embodiments of the aspects described above step (ii) comprises a freeze drying step.

In a fourth aspect there is a pharmaceutical or veterinary composition in injectable form comprising a composition according to any one of the aspects above, and optionally one or more additional (pharmaceutically acceptable) excipients.

In a fifth aspect there is a pharmaceutical or veterinary composition as described in the aspect above in intramuscularly-injectable and/or subcutaneously-injectable form.

In a sixth aspect there is an intramuscularly-injectable formulation of nanoparticles of a prodrug compound as defined herein and according to formula (I).

In a seventh aspect there is a subcutaneously-injectable formulation of nanoparticles of a prodrug compound as defined herein and according to formula (I).

In an eighth aspect there is intramuscularly-injectable formulation according to the aspects above, or a subcutaneously-injectable formulation according to the aspects above, wherein each nanoparticle of the prodrug compound is a core around which an outer layer composed of one or more carrier materials is provided.

In a ninth aspect there is a pharmaceutical or veterinary composition according to the aspects above, an intramuscularly-injectable formulation according to the aspects above, or a subcutaneously-injectable formulation according to the aspects above, in depot form.

In a tenth aspect there is a pharmaceutical or veterinary composition, an intramuscularly-injectable formulation, or a subcutaneously-injectable formulation, according to the aspects above, when administered to a patient releases the prodrug compound as defined herein and according the formula (I) into the bloodstream of the patient over a period of at least about two weeks from the date of administration.

In an eleventh aspect there is an aqueous dispersion, comprising a plurality of nanoparticles of a prodrug compound as defined herein and according to formula (I) dispersed in an aqueous medium, each nanoparticle of the prodrug compound being a core around at least some of which an outer layer composed of one or more carrier materials is provided, wherein the prodrug is present in a concentration of at least 10 mg/mL.

In a twelfth aspect there is an oily dispersion, comprising a plurality of nanoparticles of a prodrug compound as defined herein and according to formula (I) and one or more carrier materials dispersed in an oily medium, wherein the prodrug is present in a concentration of at least 10 mg/mL.

In an thirteenth aspect there is a composition according to the aspects above, a pharmaceutical or veterinary composition in injectable form according to the aspects above, an intramuscularly-injectable formulation according to the aspects above, a subcutaneously-injectable formulation according to the aspects above, an aqueous dispersion according to the aspects above, or an oily dispersion as according to the aspects above, for use as a medicament.

In a fourteenth aspect there is a composition according to the aspects above, a pharmaceutical or veterinary composition in injectable form according to the aspects above, an intramuscularly-injectable formulation according to the aspects above, a subcutaneously-injectable formulation according to the aspects above, an aqueous dispersion according to the aspects above, or an oily dispersion as according to the aspects above, for use in treating and/or preventing an HIV infection or cancer.

In a fifteenth aspect there is a composition according to the aspects above, a pharmaceutical or veterinary composition in injectable form according to the aspects above, an intramuscularly-injectable formulation according to the aspects above, a subcutaneously-injectable formulation according to the aspects above, an aqueous dispersion according to the aspects above, or an oily dispersion as according to the aspects above, further comprising at least one other anti-HIV compound and for use in treating and/or preventing an HIV infection or further comprising at least one other anti-cancer compound and for use in treating and/or preventing cancer.

In a sixteenth aspect there is a method of treating and/or preventing an HIV infection or treating and/or preventing cancer, the method comprising administering a therapeutically effect amount of a composition according to the aspects above, a pharmaceutical or veterinary composition in injectable form according to the aspects above, an intramuscularly-injectable formulation according to the aspects above, a subcutaneously-injectable formulation according to the aspects above, an aqueous dispersion according to the aspects above, or an oily dispersion according to the aspects above.

In a seventeenth aspect there is a prodrug compound according to the formula (I):

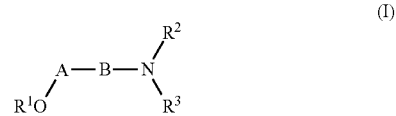

wherein,

A may be a linker with a chain length having an integer of from 1 to 10 atoms;

B may be an optionally substituted heterocycle;

$R^1$ may be —H, optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl, optionally substituted —C(=O)$C_{1-20}$alkyl, optionally substituted —$CO_2C_{1-20}$alkyl, optionally substituted —C(=O)NH$C_{1-20}$alkyl, optionally substituted —C(=O)N($C_{1-20}$alkyl)$_2$, optionally substituted —P(=O)O$R^4$O$R^5$, optionally substituted —P(=O)O$R^6R^7$, optionally substituted —(CH$_2$)$_n$P(=O)O$R^8$O$R^9$, optionally substituted —(CH)$_n$P(=O)O$R^{10}$NH$R^{11}$, optionally substituted —SiR$^{Si1}$R$^{Si2}$R$^{Si3}$, optionally substituted

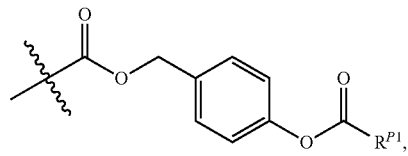

optionally substituted

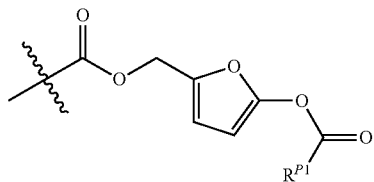

or substituted optionally substituted

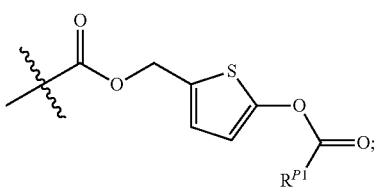

wherein $R^4$ to $R^{11}$ and $R^{Si1}$ to $R^{Si3}$ and may be each independently selected from —H, optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl;

$R^{P1}$ may be selected from optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl;

n may be an integer selected from 1, 2, 3, 4 or 5;

$R^2$ and $R^3$ may be each independently selected from —H, optionally substituted —C(=O)$C_{1-20}$alkyl, optionally substituted —C(=O)$C_{6-14}$aryl, optionally substituted —C(=O)$C_{5-14}$heteroaryl, optionally substituted —$CO_2C_{1-20}$alkyl, optionally substituted —$CO_2C_{6-14}$aryl, optionally substituted —$CO_2C_{5-14}$heteroaryl, optionally substituted —C(=O)NH$C_{1-20}$alkyl, optionally substituted —C(=O)NH$C_{6-14}$aryl, optionally substituted —C(=O)NH$C_{5-14}$heteroaryl, optionally substituted =$CR^{12}NR^{12a}R^{12b}$, an optionally substituted trimethyl lock analogue or an optionally substituted trimethyl lock analogue, optionally substituted

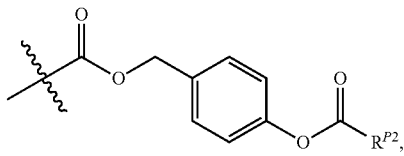

optionally substituted

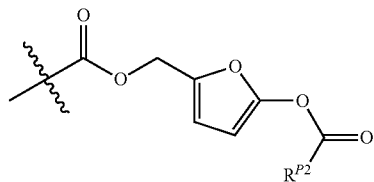

or optionally substituted

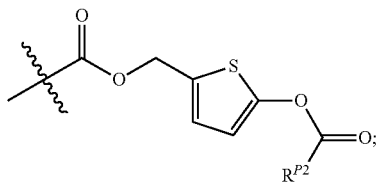

wherein at least one of $R^2$ or $R^3$ is not —H $R^{12}$, $R^{12a}$ and $R^{12b}$ may be each independently selected from —H, optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$ alkynyl, optionally substituted —$C_{2-6}$heteroalkynyl, optionally substituted —$C_{6-14}$aryl or optionally substituted —$C_{5-14}$heteroaryl; and $R^{P2}$ may be selected from optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl.

In some embodiments there is prodrug compound according to the seventeenth aspect, wherein A may be a linker according to formula (II):

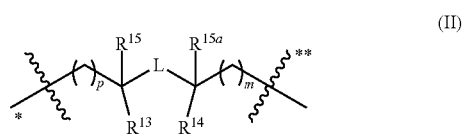

(II)

wherein (*) denotes the point of attachment to $R^1O$ and () denotes the point of attachment to B; or () denotes the point of attachment to $R^1O$ and (*) denotes the point of attachment to B L may be —O, —$NR^{L1}$, —S or —$CR^{L2}R^{L3}$; wherein $R^{L1}$, $R^{L2}$ and $R^{L3}$ are each independently selected from —H, optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl;

$R^{13}$, $R^{14}$, $R^{15}$ and $R^{15a}$ may be each independently selected from —H, optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl;

optionally wherein $R^{13}$ and $R^{14}$ may be taken together with the carbons to which they are attached to form an optionally substituted —$C_{3-10}$cycloalkyl, optionally substituted —$C_{3-10}$heterocycloalkyl, optionally substituted —$C_{3-10}$cycloalkenyl, optionally substituted —$C_{3-10}$heterocycloalkenyl, optionally substituted —$C_{6-14}$aryl or optionally substituted —$C_{5-14}$heteroaryl; and m and p may be each independently selected as integers from 0, 1, 2, 3, 4 or 5.

In further embodiments, there is a prodrug compound, wherein:

(*) denotes the point of attachment to $R^1O$ and (**) denotes the point of attachment to B;

L may be —$CH_2$ or —O;

$R^{13}$ and $R^{14}$ may be taken together with the carbons to which they are attached to form an optionally substituted —$C_{3-10}$cycloalkyl, optionally substituted —$C_{3-10}$heterocycloalkyl or optionally substituted —$C_{3-10}$cycloalkenyl;

$R^{15}$ may be —H, optionally substituted —$C_{1-6}$alkyl, optionally substituted —$C_{2-6}$heteroalkyl, optionally substituted —$C_{2-6}$alkenyl, optionally substituted —$C_{2-6}$ heteroalkenyl, optionally substituted —$C_{2-6}$alkynyl or optionally substituted —$C_{2-6}$heteroalkynyl;

$R^{15a}$ may be —H; and p may be 1.

In another embodiment there is a prodrug compound, wherein A may be optionally substituted

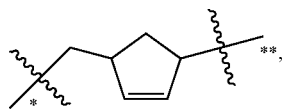 [SMILES: *CC1C=CC(*)C1]

optionally substituted

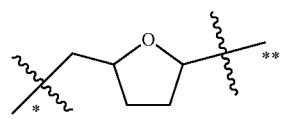 [SMILES: *CC1CCC(*)O1]

or optionally substituted

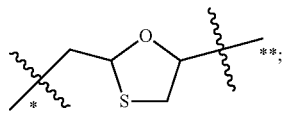 [SMILES: *CC1OC(*)CS1]

and (*) denotes the point of attachment to $R^1O$ and (**) denotes the point of attachment to B.

In a further embodiment B may be an optionally substituted —$C_{5-14}$heteroaryl.

In still further embodiments, B may be a purine analogue or pyrimidine analogue.

In other embodiments there is a prodrug compound, wherein B may be a purine analogue according to the formula (III) or pyrimidine analogue according to the formula (IV):

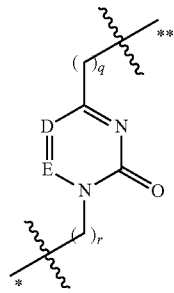

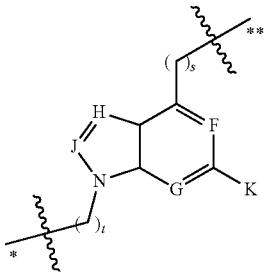

wherein (*) denotes the point of attachment to A and (**) denotes the point of attachment to $NR^2R^3$;

D, E, F, G, H and J may be each independently selected from —CH, —N, —CF, —CCl, —CBr, —$CR^{16}$, —$CNR^{16a}R^{16b}$, —$COR^{16c}$ or —$CSR^{16d}$;

K may be —H, halogen, optionally substituted —$C_{1-6}$haloalkyl, —$OR^{17}$, —$NR^{17a}R^{17b}$, —$NO_2$, —CN, optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl;

wherein $R^{16}$, $R^{16a}$, $R^{16b}$, $R^{16c}$, $R^{16d}$, $R^{17}$, $R^{17a}$ and $R^{17b}$ may be each independently selected from —H, optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl; and q, r, s and t may be each independently selected as integers from 0, 1, 2, 3, 4 or 5.

In further embodiments, therefore is prodrug compound wherein B may be a purine analogue according to the formula (III):

D may be —CH or —CF;

E may be —CH; and q may be 0 and r is 0 or 1;

or
wherein B may be a pyrimidine analogue according to the formula (IV):
F, G, H and J may be each independently selected from —CH or —N;
K may be —CH$_3$, —NH$_2$ or halogen;
s may be 0 and
t may be 0 or 1.

In yet still further embodiments there is a prodrug compound wherein,
R$^1$ may be —H, optionally substituted —C(=O)C$_{1-8}$alkyl, optionally substituted —CO$_2$C$_{1-8}$alkyl, optionally substituted —C(=O)NHC$_{1-8}$alkyl, optionally substituted —C(=O)N(C$_{1-8}$alkyl)$_2$, optionally substituted —(CH$_2$)$_n$P(=O)OR$^8$OR$^9$ or optionally substituted —(CH)$_n$P(=O)OR$^{10}$NHR$^{11}$;
R$^8$ to R$^{11}$ may be each independently selected from —H, optionally substituted —C$_{1-6}$alkyl, optionally substituted —C$_{2-6}$heteroalkyl, optionally substituted —C$_{3-6}$cycloalkyl, optionally substituted —C$_{3-6}$heterocycloalkyl, optionally substituted —C$_{6-14}$aryl or optionally substituted —C$_{5-14}$heteroaryl; and
n may be 1.

In some embodiments, R$^1$ may be —H, optionally substituted —C(=O)C$_{4-8}$alkyl, optionally substituted —CO$_2$C$_{4-8}$alkyl; optionally substituted —(CH$_2$)$_n$P(=O)OR$^8$OR$^9$ or optionally substituted —(CH)$_n$P(=O)OR$^{10}$NHR$^{11}$; and
R$^8$ to R$^{11}$ may be each independently selected from —H, optionally substituted —C$_{1-6}$alkyl, optionally substituted —C$_{2-6}$heteroalkyl or optionally substituted —C$_{6-14}$aryl.

In other embodiments R$^1$ may be optionally substituted —C(=O)C$_{4-8}$alkyl.

In still other embodiments R$^1$ may be optionally substituted —(CH$_2$)$_n$P(=O)OR$^8$OR$^9$ or optionally substituted —(CH)$_n$P(=O)OR$^{10}$NHR$^{11}$;

R$^8$ and/or R$^9$ may be —CH$_2$OC(=O)OR$^{18}$ wherein R$^{18}$ may be optionally substituted —C$_{1-6}$alkyl;
R$^{10}$ may be optionally substituted —C$_{1-6}$alkyl or optionally substituted —C$_{6-14}$aryl and R$^{11}$ may be —CHR$^{19}$CO$_2$R$^{20}$ wherein R$^{19}$ and R$^{20}$ may be optionally substituted —C$_{1-6}$alkyl.

In embodiments there is a prodrug compound wherein:
R$^2$ may be optionally substituted —CO$_2$C$_{1-20}$alkyl, optionally substituted =CR$^{12}$N(C$_{1-6}$alkyl)$_2$ or an optionally substituted trimethyl lock analogue;
R$^3$ may be H.

In other embodiments R$^2$ may be optionally substituted —CO$_2$C$_{1-8}$alkyl, preferably optionally substituted —CO$_2$C$_{4-8}$alkyl;
=CR$^{12}$N(CH$_3$)$_2$;

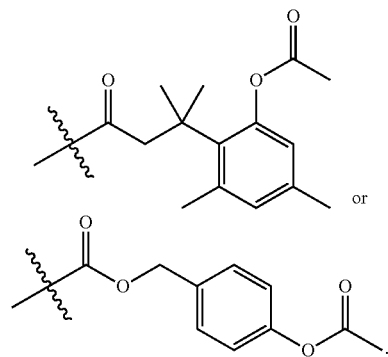

In an eighteen aspect there is a prodrug compound selected from any one of the following formulae:

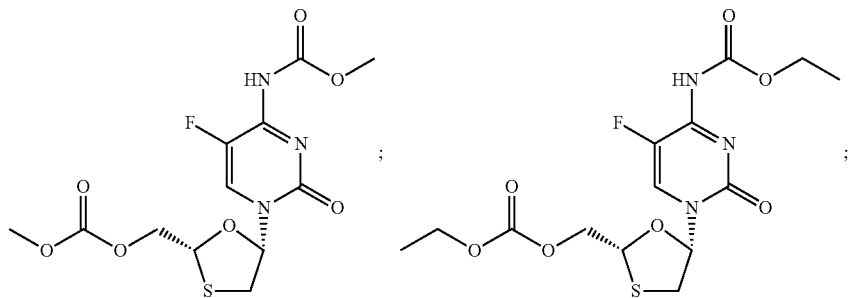

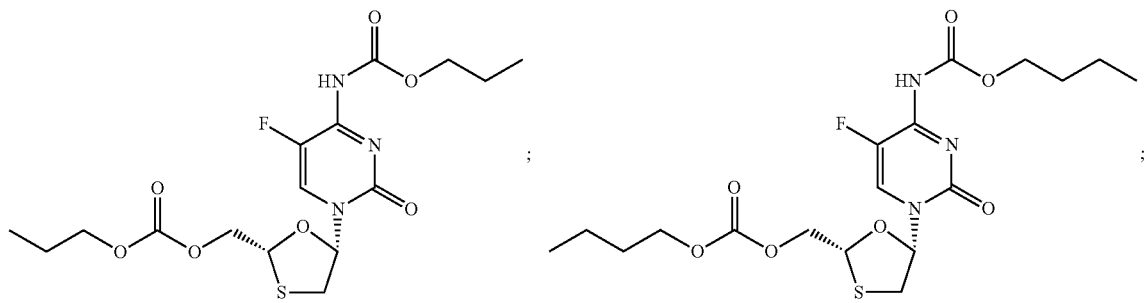

-continued
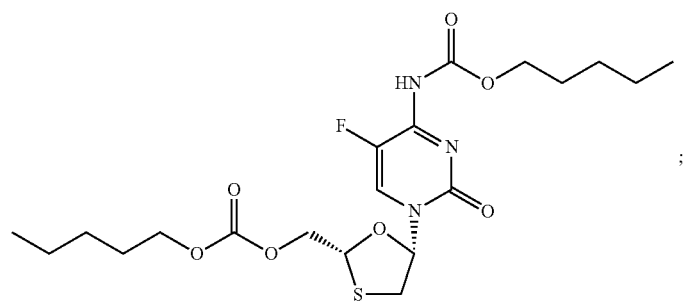
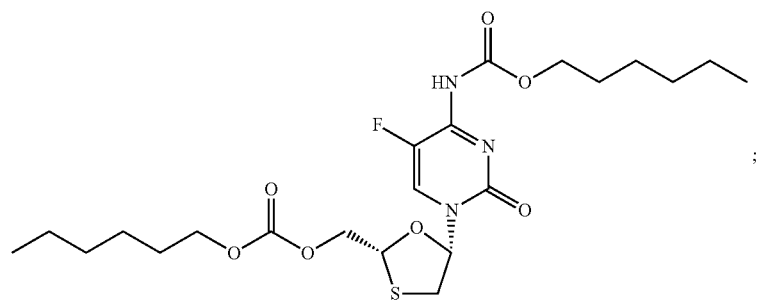
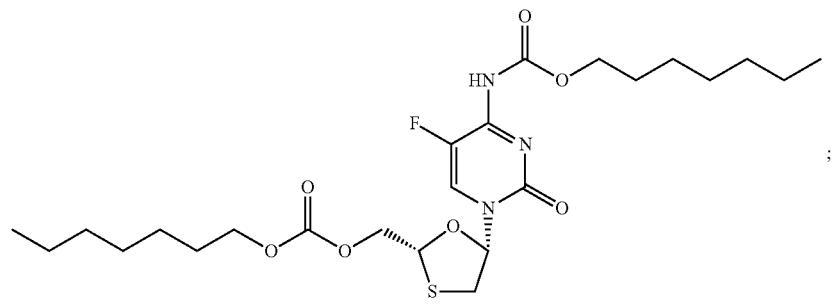
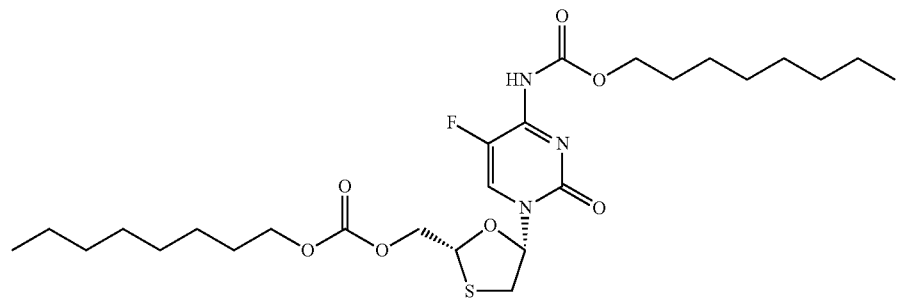 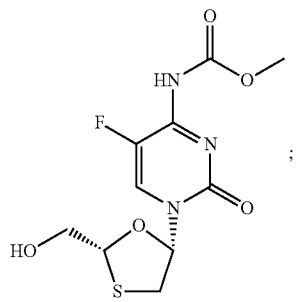
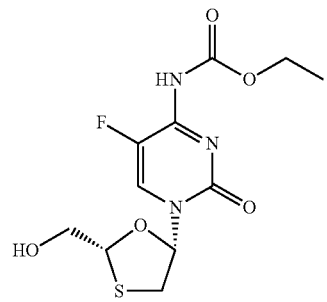 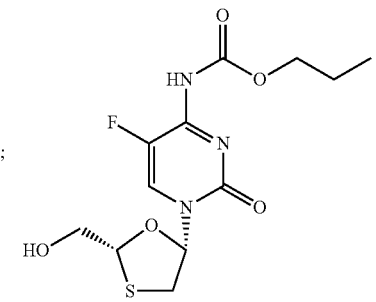 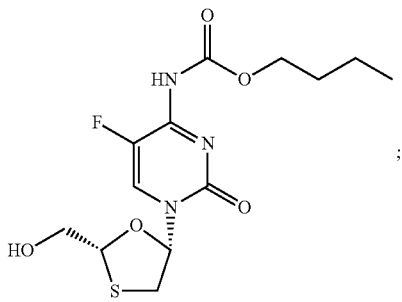

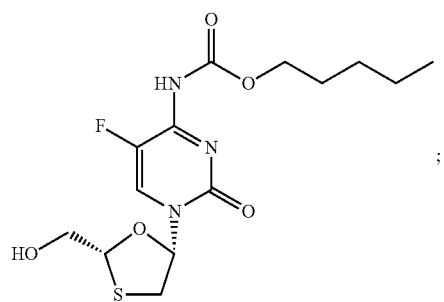
;
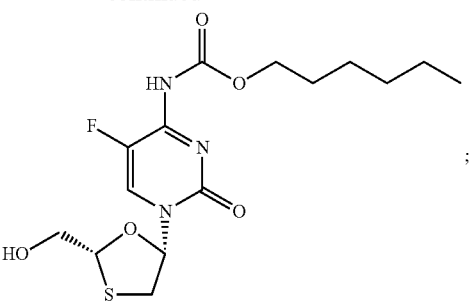
;
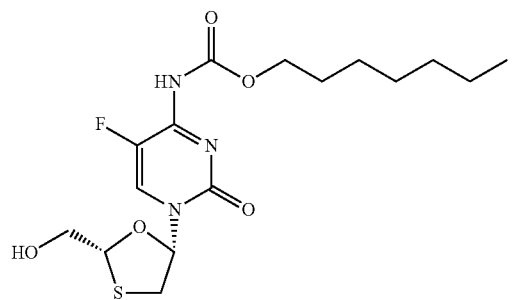
;
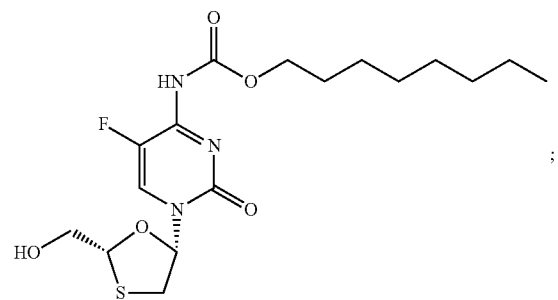
;
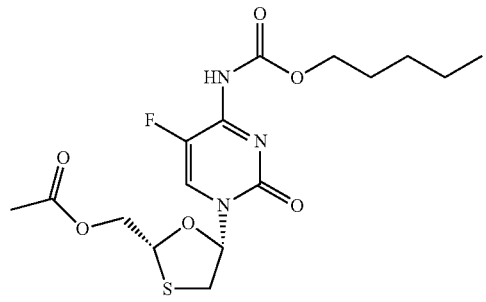
;
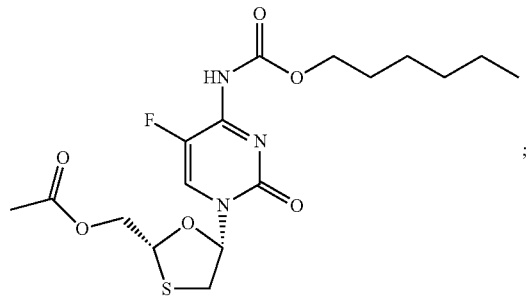
;
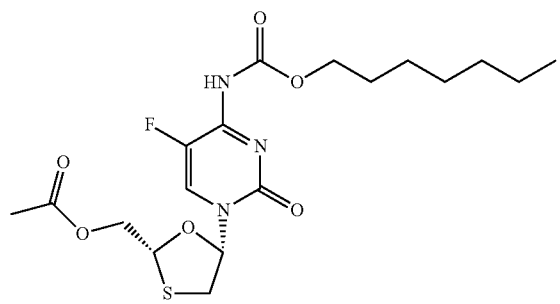
;
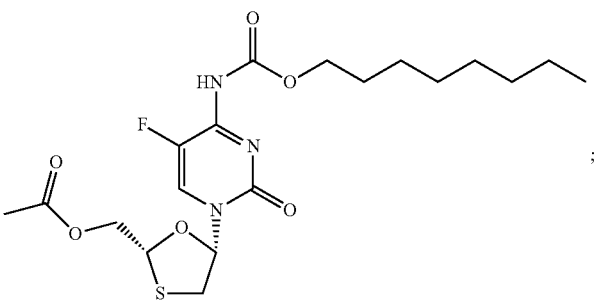
;
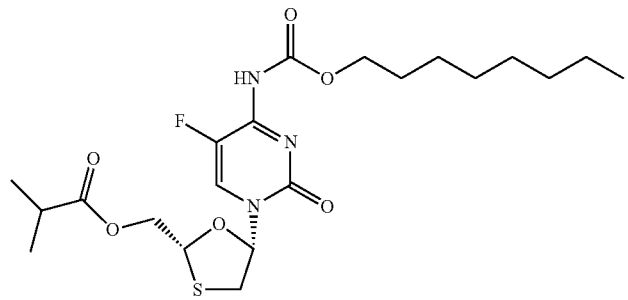
;
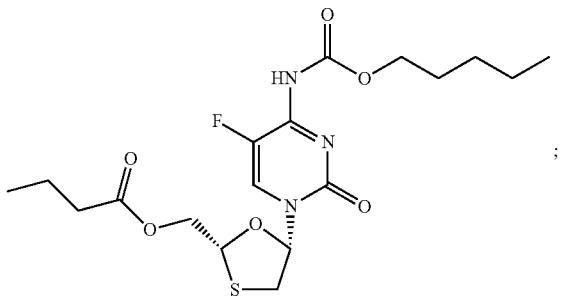
;

-continued

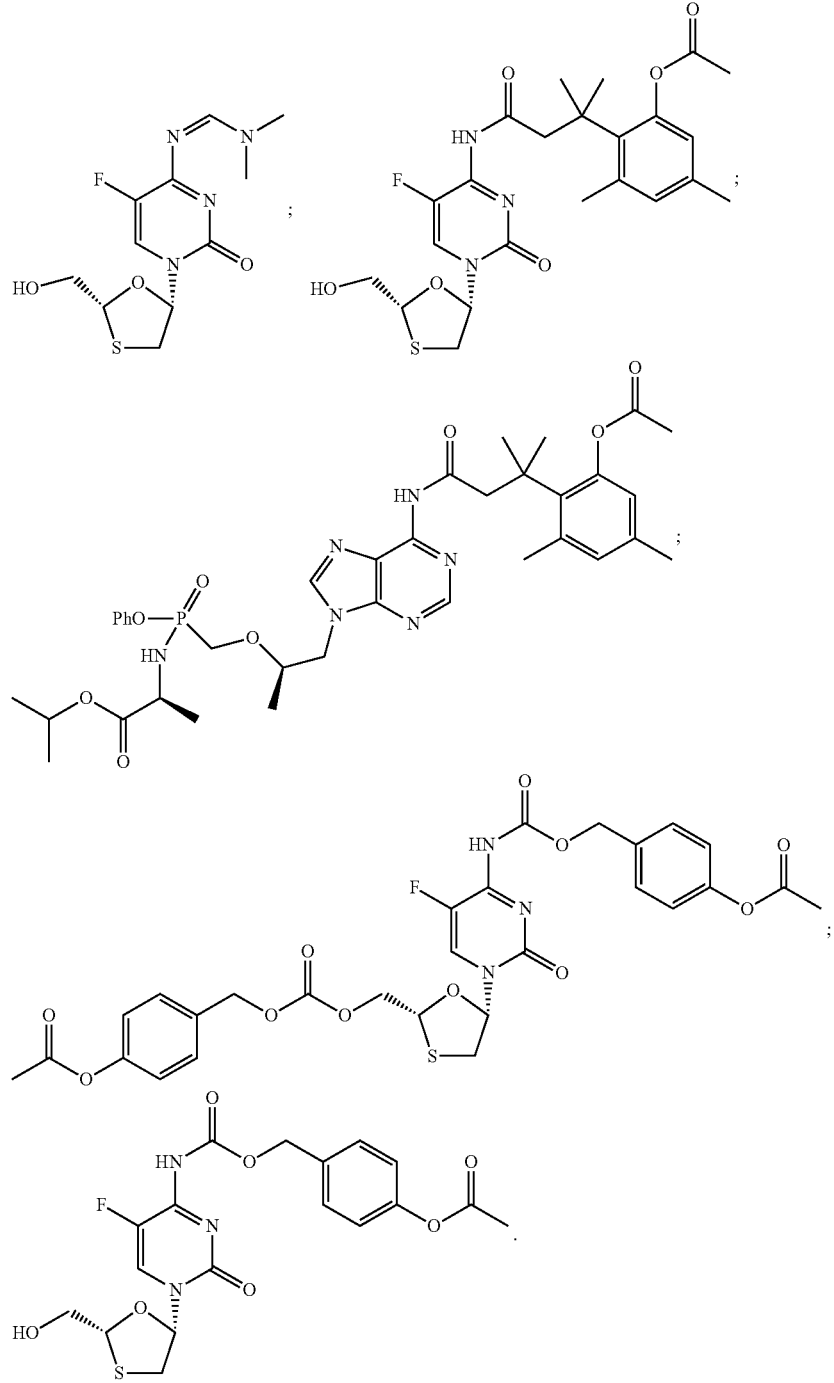

In a nineteenth aspect there is a prodrug according to any one of the seventeenth and/or eighteenth aspect for use as a medicament.

In a twentieth aspect there is a prodrug according to any one of the seventeenth and/or eighteenth aspect for use as a medicament for use in treating and/or preventing an HIV infection or cancer.

In a twenty first aspect there is a prodrug according to any one of the seventeenth and/or eighteenth aspect for use as a medicament, further comprising at least one other anti-HIV compound and for use in treating and/or preventing an HIV infection or further comprising at least one other anti-cancer compound and for use in treating and/or preventing cancer.

In a twenty second aspect there is a method of treating and/or preventing an HIV infection or treating and/or preventing cancer, the method comprising administering a therapeutically effect amount of a prodrug compound according to any one of the seventeenth and/or eighteenth aspect.

Prodrug Nanoparticle Compositions

In an aspect of the present invention there is a composition comprising nanoparticles of a prodrug compound dispersed within one or more carrier materials, wherein the log P value of the prodrug compound is at least about 1 and greater than the log P value of the pharmaceutically active agent.

The term "nanoparticle" or "nanoparticulate" is used herein to mean a particle having a hydrodynamic diameter of less than or equal to 1 micron (µm), but greater than or equal to 1 nanometre (nm), i.e. in the range 1-1000 nm. These terms are clear and well understood by a person skilled in the art, without any confusion, not least as evidenced by Petros and DeSimone, *Nature Reviews Drug Discovery*, 2010, 9, 615-627.

The term "prodrug" compound is used herein to mean compounds which may have little or no pharmacological activity themselves, which can, when administered in vivo, be converted into "pharmaceutically active agents". Prodrug compounds can, for example, be produced by replacing functionalities present in the pharmaceutically active agents with appropriate moieties which are metabolized in vivo to form the active agents or pharmaceutically active agents. Examples of prodrugs compounds of the invention are carbamates, carbonates, esters, amides, and imidines of pharmaceutically active agents. For example, where the pharmaceutically active agents contains —$NH_2$ at least one hydrogen atom of the $NH_2$ group may be replaced in order to form a carbamate, trimethyl lock derivative or imine. Where the pharmaceutically active agents contains an alcohol group (—OH), the hydrogen atom of the alcohol group may be replaced in order to form an ester (e.g. the hydrogen atom may be replaced by —$C(O)C_{1-6}$alkyl) or carbonate (e.g. the hydrogen atom may be replaced by —$CO_2C_{1-6}$ alkyl).

The prodrug nanoparticle compositions as described herein may be in solid form (or substantially solid form, e.g. a paste) or liquid form or semi-solid form, in which the prodrug is present in the form of nanoparticles. The nanoparticles of the prodrug may be dispersed within one or more solid carrier materials. Preferably, the prodrug nanoparticle compositions of the present invention are in solid form.

The term "emtricitabine" is used herein to refer to the molecule illustrated below, and also includes pharmaceutically acceptable salts, solvates and derivatives thereof, prodrugs thereof, as well as any polymorphic or amorphous forms thereof.

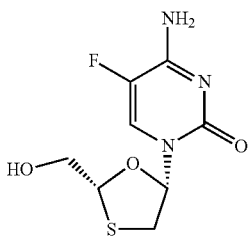 [SMILES: Nc1nc(=O)n([C@@H]2CS[C@H](CO)O2)cc1F]

Unless otherwise stated, the weight percentages ("wt %") discussed herein relate to the % by weight of a particular constituent (e.g. prodrug compound) as a proportion of the total weight of the composition (prodrug nanoparticle composition).

Preferably, the prodrug compound is present in an amount of at least 15 wt %, further preferably at least 20 wt %, yet further preferably at least 25 wt %, yet further preferably at least 30 wt %, yet further preferably at least 40 wt %, yet further preferably at least 50 wt %, yet further preferably at least 60 wt %, yet further preferably 70 wt %, and most preferably at least 80 wt %.

Preferably, the one or more carrier materials may provide hydrophilic polymeric and surfactant activity, and further preferably may be selected from the group consisting of: Pluronics® F-68, Pluronics® F-127, polyvinyl alcohol (PVA), Kollicoat™, polyethylene glycol (PEG) k1 (Mw 1,000), hydroxylpropyl methyl cellulose (HPMC), polyvinylpyrrolidone k30 ('PVP k30'), Vitamin-E-polyethylene glycol-succinate (TPGS), sodium deoxycholate (NDC), polyoxyethylene (20) sorbitan monolaurate (Tween™ 20), polyoxyethylene (20) sorbitan monooleate (Tween™ 80), dioctyl sulfosuccinate sodium salt (AOT) and polyethylene glycol (15)-hydroxystearate (Solutol™ HS).

References herein to a carrier material being "(substantially) immiscible" with another carrier material means that a mixture comprising the two carrier materials is unable to form a single phase.

Throughout this specification, it is described that "the one or more carrier materials may provide hydrophilic polymeric and surfactant activity", by which it is meant that there may be a single carrier material providing both hydrophilic polymeric activity and surfactant activity, or there may be a plurality of carrier materials, in which case one (or more) carrier material(s) in the plurality may provide hydrophilic polymeric activity, while another carrier material (or carrier materials) in the plurality may provide surfactant activity. In the latter case, the one or more carrier materials may be referred to simply as "(hydrophilic) polymers" or "surfactants", for carrier materials providing hydrophilic polymeric activity and surfactant activity respectively, for simplicity.

Hydrophilic Polymer

Preferably, the following hydrophilic polymers are suitable for use in the present invention:
 ethylene oxide-propylene oxide block copolymers (available under the trade name Pluronics® F-68 or Pluronics® F-127);
 polyvinyl alcohol (PVA);
 polyvinyl alcohol-polyethylene glycol graft copolymer (available under the trade name Kollicoat™);
 polyethylene glycol (PEG) k1 (Mw 1,000);
 hydroxylpropyl methyl cellulose (HPMC); and
 polyvinylpyrrolidone k30 ('PVP k30').

Surfactant

Preferably, the following surfactants are suitable for use in the present invention:
 vitamin-E-polyethylene glycol-succinate (Vit-E-PEG-succinate, TPGS or D-α-tocopherol polyethylene glycol 1000 succinate);
 sodium deoxycholate (NDC);
 polyoxyethylene (20) sorbitan monolaurate (also known as polysorbate 20 and available under the trade name Tween™ 20);
 polyoxyethylene (20) sorbitan monooleate (also known as polysorbate 80 and available under the trade name Tween™ 80);
 dioctyl sulfosuccinate sodium salt (AOT); and
 polyethylene glycol (15)-hydroxystearate (available under the trade name Solutol™ HS).

In the present invention, the carrier material having surfactant activity is suitably selected from those surfactants that are capable of stabilising nanoparticles of prodrugs of the present invention together with the carrier material having hydrophilic polymeric activity as defined herein, and which are also approved for pharmaceutical use as excipients (e.g. they are approved for use by the US Food and Drug Administration centre for drug evaluation and research (CDER)).

Particular Combinations of Hydrophilic Polymer and Surfactant

Of course, any one or more of the aforementioned hydrophilic polymers may be combined with any one or more of the aforementioned surfactants for use in the present invention.

Accordingly, the one or more solid carrier materials may be provided in any one or more of the following combinations:

Pluronics® F-68 AND vitamin-E-polyethylene glycol-succinate;
Pluronics® F-68 AND sodium deoxycholate;
Pluronics® F-68 AND polyoxyethylene (20) sorbitan monolaurate;
Pluronics® F-68 AND polyoxyethylene (20) sorbitan monooleate;
Pluronics® F-68 AND dioctyl sulfosuccinate sodium salt;
Pluronics® F-68 AND polyethylene glycol (15)-hydroxystearate;
Pluronics® F-127 AND vitamin-E-polyethylene glycol-succinate;
Pluronics® F-127 AND sodium deoxycholate;
Pluronics® F-127 AND polyoxyethylene (20) sorbitan monolaurate;
Pluronics® F-127 AND polyoxyethylene (20) sorbitan monooleate;
Pluronics® F-127 AND dioctyl sulfosuccinate sodium salt;
Pluronics® F-127 AND polyethylene glycol (15)-hydroxystearate;
polyvinyl alcohol AND vitamin-E-polyethylene glycol-succinate;
polyvinyl alcohol AND sodium deoxycholate;
polyvinyl alcohol AND polyoxyethylene (20) sorbitan monolaurate;
polyvinyl alcohol AND polyoxyethylene (20) sorbitan monooleate;
polyvinyl alcohol AND dioctyl sulfosuccinate sodium salt;
polyvinyl alcohol-polyethylene glycol graft copolymer AND vitamin-E-polyethylene glycol-succinate;
polyvinyl alcohol-polyethylene glycol graft copolymer AND sodium deoxycholate;
polyvinyl alcohol-polyethylene glycol graft copolymer AND polyoxyethylene (20) sorbitan monolaurate;
polyvinyl alcohol-polyethylene glycol graft copolymer AND dioctyl sulfosuccinate sodium salt;
polyethylene glycol k1 AND sodium deoxycholate;
polyethylene glycol k1 AND polyoxyethylene (20) sorbitan monolaurate;
polyethylene glycol k1 AND polyoxyethylene (20) sorbitan monooleate;
polyethylene glycol k1 AND dioctyl sulfosuccinate sodium salt;
polyethylene glycol k1 AND polyethylene glycol (15)-hydroxystearate;
hydroxylpropyl methyl cellulose AND vitamin-E-polyethylene glycol-succinate;
hydroxylpropyl methyl cellulose AND sodium deoxycholate;
hydroxylpropyl methyl cellulose AND polyoxyethylene (20) sorbitan monolaurate;
hydroxylpropyl methyl cellulose AND polyoxyethylene (20) sorbitan monooleate;
hydroxylpropyl methyl cellulose AND dioctyl sulfosuccinate sodium salt;
hydroxylpropyl methyl cellulose AND polyethylene glycol (15)-hydroxystearate;
polyvinylpyrrolidone k30 AND vitamin-E-polyethylene glycol-succinate;
polyvinylpyrrolidone k30 AND sodium deoxycholate;
polyvinylpyrrolidone k30 AND polyoxyethylene (20) sorbitan monolaurate;
polyvinylpyrrolidone k30 AND polyoxyethylene (20) sorbitan monooleate;
polyvinylpyrrolidone k30 AND dioctyl sulfosuccinate sodium salt; or
polyvinylpyrrolidone k30 AND polyethylene glycol (15)-hydroxystearate.

However, the following combinations of hydrophilic polymer(s) and surfactant(s) are particularly preferred for use in the present invention:

polyvinyl alcohol AND polyoxyethylene (20) sorbitan monolaurate;
Pluronics® F-127 AND vitamin-E-polyethylene glycol-succinate;
hydroxylpropyl methyl cellulose AND N alkyldimethylbenzylammonium chloride; or
hydroxylpropyl methyl cellulose AND dioctyl sulfosuccinate sodium salt.

The one or more solid carrier materials are preferably water-soluble. In the context of the present invention, "water-soluble" as applied to the carrier material(s) means that its solubility in water at ambient temperature and pressure is at least 10 g/L.

Preferably, individual nanoparticles of the prodrug compounds as described herein consist essentially of the prodrug compound.

The composition of the present invention may be administered as it is to a patient, or further formulated to provide a pharmaceutical composition in the form of, for example, an injectable formulation, such as an intramuscular depot injection or a subcutaneous depot injection.

The nanoparticles of a prodrug compound according to the present invention have a Z-average particle diameter of less than or equal to 1000 nm. In some embodiments, the nanoparticles of a prodrug compound according to the present invention may have a Z-average particle diameter of from about 100 to about 1000 nm. In further embodiments, the Z-average particle diameter may be from about 200 to about 800 nm. Further still, the Z-average particle diameter may be from about 200 to about 400 nm. In other embodiments, the Z-average particle diameter may be from about 300 to about 500 nm, from about 350 nm to about 450 nm, from about 250 nm to about 350 nm, from about 100 to about 200 nm, from about 150 to about 250 nm or from about 100 to about 300 nm. Preferably, the Z-average particle diameter may be from about 100 to about 400 nm.

The Z-average particle diameters may be assessed by any suitable technique known in the art. Z-average particle diameters herein have been determining the particle size by dynamic light scattering with a Zetasizer Nano S (Malvern Instruments Ltd).

Unless otherwise stated, the terms "particle size", "hydrodynamic size", "particle diameter" and "hydrodynamic diameter" are used interchangeable herein and refer to the Z-average particle diameter (also known as Dz).

The polydispersity of the nanoparticles of a prodrug compound according to the present invention may be less than or equal to 0.8, preferably less than or equal to 0.6, and more preferably less than or equal to 0.5. The polydispersity relates to the size of the nanoparticles of a prodrug compound and may be determined by suitable techniques known in the art (e.g. laser diffraction, laser scattering, electron microscopy). Polydispersity of particle sizes and Z-average particle diameters of the nanoparticles of a prodrug compound herein have been assessed with a Malvern Zetasizer Nano S (Malvern Instruments Ltd).

The composition may comprise particles or granules of larger size, for example, 5 to 30 microns (μm) in size, wherein each particle or granule contains a plurality of nanoparticles of a prodrug compound dispersed within the one or more solid carrier materials. These larger particles or granules disperse when the composition is mixed with an aqueous medium to form discrete nanoparticles of nanoparticles of the prodrug compound.

Formulation of the Composition Comprising Nanoparticles of a Prodrug Compound

In a particular embodiment, the composition as defined herein may comprise 10 to 99 wt % of a prodrug compound of the present invention. Preferably, or in another embodiment, the composition may comprise 15 to 95 wt % of a prodrug compound of the present invention. In another embodiment, the composition may comprise at least 20 wt %, more preferably or alternatively at least 40 wt %, yet further preferably or alternatively at least 60 wt %, and alternatively at least 80 wt % of a prodrug compound of the present invention. Preferably, the composition may comprise from about 40 to about 60 wt % of prodrug compound, from about 50 to about 70 wt % of prodrug compound or from about 30 to about 50 wt % of prodrug compound. Even more preferably, the composition may from at least 70% of prodrug compound.

The prodrug compound of the present invention is present in any amount of at least 10 wt %, such as in the range of from 10-99 wt %, or from 10-95 wt %, or from 10-90 wt %.

Alternatively, the prodrug compound of the present invention may be present in an amount of at least 15 wt %, such as in the range of from 15-99 wt %, or from 15-95 wt %, or from 15-90 wt %.

Further alternatively, the prodrug compound of the present invention may be present in an amount of at least 20 wt %, such as in the range of from 20-99 wt %, or from 20-95 wt %, or from 20-90 wt %.

Yet further alternatively, the prodrug compound of the present invention may be present in an amount of at least 25 wt %, such as in the range of from 25-99 wt %, or from 25-95 wt %, or from 25-90 wt %.

Still further alternatively, the prodrug compound of the present invention may be present in an amount of at least 30 wt %, such as in the range of from 30-99 wt %, or from 30-95 wt %, or from 30-90 wt %.

Still further alternatively, the prodrug compound of the present invention may be present in an amount of at least 40 wt %, such as in the range of from 40-99 wt %, or from 40-95 wt %, or from 40-90 wt %.

Still further alternatively, the prodrug compound of the present invention may be present in an amount of at least 50 wt %, such as in the range of from 50-99 wt %, or from 50-95 wt %, or from 50-90 wt %.

Still further alternatively, the prodrug compound of the present invention may be present in an amount of at least 60 wt %, such as in the range of from 60-99 wt %, or from 60-95 wt %, or from 60-90 wt %.

Still further alternatively, the prodrug compound of the present invention may be present in an amount of at least 70 wt %, such as in the range of from 70-99 wt %, or from 70-95 wt %, or from 70-90 wt %.

Still further alternatively, the prodrug compound of the present invention may be present in an amount of at least 80 wt %, such as in the range of from 80-99 wt %, or from 80-95 wt %, or from 80-90 wt %.

The compositions of the present invention therefore permit high drug loadings, which keeps the potentially toxic excipients (e.g. surfactants) to a minimum.

The composition may comprise 1 to 90 wt % of the one or more selected carrier materials. Preferably, or in one embodiment, the composition may comprise 5 to 85 wt % of the one or more carrier materials. Further preferably, or in another embodiment, the composition may comprise 10 to 80 wt % of the one or more carrier materials. In a particular embodiment, the composition may comprise 20 to 60 wt % of the one or more selected carrier materials. For the avoidance of doubt, the percentage amount of the selected carrier materials refers to the total weight amount of all said selected carrier materials in that composition.

In a particular embodiment, the composition may comprise 1 to 90 wt % of hydrophilic polymer. Preferably, or in another embodiment, the composition may comprise 8 to 70 wt % of hydrophilic polymer. Further preferably, or in another embodiment, the composition may comprise 10 to 60 wt % of hydrophilic polymer. Yet further preferably, or in a particular embodiment, the composition may comprise 10 to 50 wt % of hydrophilic polymer.

In a particular embodiment, the composition may comprise 1 to 70 wt % of surfactant. Preferably, or in another embodiment, the composition may comprise 2 to 50 wt % of surfactant. Further preferably, or in another embodiment, the composition may comprise 3 to 30 wt % of surfactant.

In an embodiment, the composition may comprise the carrier material providing hydrophilic polymeric activity and the carrier material providing surfactant activity in a respective ratio of between 30:1 and 1:10. Preferably, or in a particular embodiment, the composition may comprise the carrier material providing hydrophilic polymeric activity and the carrier material providing surfactant activity in a respective ratio of between 15:1 and 1:2. Further preferably, or in another embodiment, the composition may comprise the carrier material providing hydrophilic polymeric activity and the carrier material providing surfactant activity in a respective ratio of between 10:1 and 2:1. Yet further preferably, or in a particular embodiment, the composition may comprise the carrier material providing hydrophilic polymeric activity and the carrier material providing surfactant activity in a respective ratio of between 6:1 and 3:1.

In a particularly preferred embodiment, the composition comprises:
- 40 to 90 wt % of a prodrug compound of the present invention;
- 8 to 40 wt % of a carrier material providing hydrophilic polymeric activity; and
- 2 to 20 wt % of a carrier material providing surfactant activity.

The composition may comprise one or more additional excipients, for instance, to further facilitate dispersion or stabilisation of dispersions of the nanoparticles either in a pharmaceutically acceptable diluent or in vivo.

Processes for Preparing the Prodrug Nanoparticle Compositions

Compositions of the present invention may be prepared by a number of methods well known in the art. Suitable techniques for forming such compositions are described in general terms in Horn and Rieger, *Angew. Chem. Int. Ed.*, 2001, 40, 4330-4361.

For example, the composition may be prepared by milling the prodrug compounds of the present invention. The milling may occur in the presence of the one or more carrier materials, e.g. the hydrophilic polymer and surfactant, or, alternatively, they may be mixed with the milled prodrugs compounds after the milling step.

However, it is generally preferred that the compositions of the present invention are prepared by an oil-in-water (o/w) emulsion technique whereby a prodrug of the present invention is dissolved in the oil phase and the carrier material(s), e.g. providing hydrophilic polymeric and surfactant activity, are present in the water phase. The oil and water solvents are then removed by freeze-drying, spray-drying or spray-granulation to provide a composition according to the invention.

Thus, in accordance with one aspect of the present invention, there is provided a process for preparing a composition as defined herein, the process comprising:
(a) preparing an oil-in-water emulsion comprising:
   an oil phase comprising a prodrug of the present invention; and
   an aqueous phase comprising one or more selected carrier materials as defined herein; and
(b) removing the oil and water from the oil-in-water emulsion to form the solid composition.

An advantage of the oil-in-water (o/w) emulsion processes of the present invention is that the emulsions formed in the initial steps are sufficiently homogenous and stable to allow for effective and uniform drying upon removal of the oil and water. Furthermore, the nanoparticles formed are substantially uniform in their physical form (size, shape etc.). A further advantage of the processes of the present invention is that prodrug compounds possessing low melting points and often semi-solid (as described herein) may be successfully processed to provide solid nanoparticles with desirable properties. This is not possible with conventional milling techniques.

The oil-in-water emulsion formation steps may be performed by methods well-known in the art. Any suitable method for forming the oil-in-water emulsions may therefore be used. In particular, mixing of the oil and water phases to form the oil-in-water emulsion may be performed by methods well known in the art. For example, the mixing may involve stirring, sonication, homogenisation, or a combination thereof. In a particular embodiment, the mixing is facilitated by sonication and/or homogenisation.

The oil-in-water emulsion formation steps may be performed, for example, by using the methods described in WO 2004/011537 A1 (COOPER et al), which is hereby duly incorporated by reference.

In a particular embodiment, oil-in-water emulsion formation comprises:
(i) providing an oil phase comprising a prodrug of the present invention;
(ii) providing an aqueous phase comprising the one or more selected carrier materials; and
(iii) mixing the oil phase and aqueous phase to produce the oil-in-water emulsion.

Suitably, the oil phase is provided by dissolving a prodrug of the present invention in a suitable organic solvent. Suitably, the aqueous phase is provided by dissolving the one or more selected carrier materials in an aqueous medium, preferably in water. In embodiments where more than one said selected carrier material is used, the aqueous phase may be provided by mixing a corresponding number of separately prepared aqueous solutions of each selected carrier material.

In a particular embodiment, further aqueous medium (e.g. water) or organic solvent is added before or during mixing step (iii).

The concentration of the prodrug in the oil-in-water emulsion is suitably as concentrated as possible to facilitate effective scale-up of the process. For example, the concentration of prodrug(s) in the oil phase is suitably 10 mg/mL or higher, more suitably 15 mg/mL or higher, even more suitably greater than 20 mg/mL or higher.

The concentration of the carrier material providing hydrophilic polymeric activity in the aqueous/water phase is suitably from about 0.5 to about 50 mg/mL. Preferably, the concentration of the carrier material providing hydrophilic polymeric activity in the aqueous/water phase is suitably from about 15 to about 30 mg/mL.

The concentration of the carrier material providing surfactant activity in the aqueous/water phase emulsion is suitably from about 0.5 to about 50 mg/mL.

Preferably, the concentration of the carrier material providing surfactant activity in the aqueous/water phase emulsion is from about 15 to about 30 mg/mL.

The organic solvent forming the oil phase is (substantially) immiscible with water. Suitably the organic solvent is aprotic. Suitably the organic solvent has a boiling point less than 120° C., suitably less than 10° C., more suitably less than 90° C.

In a particular embodiment, the organic solvent is a selected from the Class 2 or 3 solvents listed in the International Conference on Harmonization (ICH) guidelines relating to residual solvents.

In a particular embodiment, the organic solvent is selected from chloroform, dichloromethane, dichloroethane, tetrachloroethane, cyclohexane, hexane(s), isooctane, dodecane, decane, methylbutyl ketone (MBK), methylcyclohexane, tetrahydrofuran, toluene, xylene, butyl acetate, mineral oil, tert-butylmethyl ether, heptanes(s), isobutyl acetate, isopropyl acetate, methyl acetate, methylethyl ketone (MEK), ethyl acetate, ethyl ether, pentane, and propyl acetate, or any suitably combination thereof.

In a particular embodiment, the organic solvent is selected from chloroform, dichloromethane, methylethylketone, methylbutylketone, and ethyl acetate.

The volume ratio of aqueous phase to oil phase in mixing step (iii) is suitably between 20:1 and 1:1, more suitably between 10:1 and 1:1, and most suitably between 6:1 and 2:1.

Mixing step (iii) suitably produces a substantially uniform oil-in-water emulsion. As previously indicated, mixing may be performed using methods well known in the art.

Suitably, mixing step (iii) involves stirring, sonication, homogenisation, or a combination thereof. In a particular embodiment, mixing step (iii) involves sonication and/or homogenisation.

Removing the oil and water may be performed using methods well known in the art. Suitably removing the oil and water involves freeze-drying, spray-drying or spray-granulation.

Removing the oil and water may be performed using methods described in WO 2004/011537 A1 (COOPER et al), the entire contents of which are hereby incorporated by reference.

In a particular embodiment, removing the oil and water involves freeze drying the oil-in-water emulsion. Removing the oil and water may suitably comprise freezing the oil-in-water emulsion and then removing the solvents under vacuum.

Preferably, freezing of the oil-in-water emulsion may be performed by externally cooling the oil-in-water emulsion. For example, a vessel containing the oil-in-water emulsion may be externally cooled, by submerging the vessel in a cooling medium, such as liquid nitrogen. Alternative media for use for freezing purposes will be well known to those of skill in the art.

Alternatively the vessel containing the oil-in-water emulsion may be provided with an external "jacket" through which coolant is circulated to freeze the oil-in-water emulsion.

Alternatively the vessel may comprise an internal element through which coolant is circulated in order to freeze the oil-in-water emulsion.

In a further alternative, the oil-in-water emulsion is frozen by being contacted directly with a cooling medium at a temperature effective for freezing the emulsion. The "temperature effective for freezing the emulsion" will be well understood by those of skill in the art based on the freezing temperature of the emulsion for freezing. It will be appreciated that the skilled person could readily determine what temperature would be so effective based on the freezing point of the emulsion and carrier materials thereof.

In cases where the emulsion is frozen by contact with a cooling medium, the cooling medium (e.g. liquid nitrogen) may be added to the oil-in-water emulsion, or the oil-in-water emulsion may be added to the cooling medium.

In a particular embodiment, the oil-in-water emulsion is added to the fluid medium (e.g. liquid nitrogen), suitably in a dropwise manner, whereby frozen droplets of the oil-in-water emulsion may suitably form. This order of addition provides higher purities of final products. Frozen droplets may suitably be isolated (e.g. under vacuum to remove the fluid medium/liquid nitrogen). The solvent is then suitably removed from the frozen droplets under vacuum. The resulting composition is then isolated.

In an alternative aspect, the present invention provides a process for preparing a composition as defined herein, the process comprising:
    preparing a single phase solution comprising a prodrug of the present invention, and one or more selected carrier materials, in one or more solvents; and
    removing the one or more solvents to form the solid composition.

In this aspect of the invention, the single phase solution comprising the prodrug and one or more selected carrier materials are all dissolved in one solvent or two or more miscible solvents. Such processes are well described in WO2008/006712, the entire contents of which are duly incorporated herein by reference. WO2008/006712 also lists suitable solvents and combinations thereof for forming the single phase solution.

In an embodiment, the single phase solution comprises two or more solvents (e.g. ethanol and water) which together solubilise prodrug and the one or more selected carrier materials. In another embodiment, the single phase comprises a single solvent, for example ethanol or water.

Removing the one or more solvents may be performed using methods well known in the art. Suitably removing the one or more solvents involves freeze-drying, spray-drying or spray-granulation.

In a particular embodiment, removing the one or more solvents involves freeze drying the single phase solution.

Removing the one or more solvents may suitably comprise freezing the single phase solution and then removing the solvents under vacuum.

The present invention also provides a composition obtainable by, obtained by, or directly obtained by any of the processes described herein.

Aqueous or Oily Dispersion of Prodrug Nanoparticles

The present invention provides an aqueous dispersion, comprising a plurality of nanoparticles of a prodrug of the present invention dispersed in an aqueous medium, each nanoparticle of the prodrug of the present invention being a core around at least some of which an outer layer composed of one or more carrier materials may be provided, wherein the prodrug of the present invention is present in a concentration of at least 10 mg/mL.

The present invention also provides an oily dispersion, comprising a plurality of nanoparticles of a prodrug of the present invention and one or more carrier materials dispersed in an oily medium, wherein the prodrug of the present invention is present in a concentration of at least 10 mg/mL.

Preferably, or in one embodiment, the prodrug of the present invention is present in the dispersion in a concentration of at least 15 mg/mL. Further preferably, or an in alternative embodiment, the prodrug of the present invention is present in the dispersion in a concentration of at least 18 mg/mL. Yet further preferably, or in an alternative embodiment, the prodrug of the present invention is present in the dispersion in a concentration of at least 20 mg/mL or even at least 25 mg/mL.

Preferably, the one or more carrier materials may provide hydrophilic polymeric and surfactant activity, and further preferably may be selected from the group consisting of: Pluronics® F-68, Pluronics® F-127, polyvinyl alcohol (PVA), Kollicoat™, polyethylene glycol k1, hydroxylpropyl methyl cellulose (HPMC), polyvinylpyrrolidone k30 ('PVP k30'), Vitamin-E-polyethylene glycol-succinate (TPGS), sodium deoxycholate (NDC), polyoxyethylene (20) sorbitan monolaurate (Tween™ 20), polyoxyethylene (20) sorbitan monooleate (Tween™ 80), dioctyl sulfosuccinate sodium salt (AOT) and polyethylene glycol (15)-hydroxystearate (Solutol™ HS).

Accordingly, the one or more solid carrier material may be provided in any one or more of the following combinations:
    Pluronics® F-68 AND vitamin-E-polyethylene glycol-succinate;
    Pluronics® F-68 AND sodium deoxycholate;
    Pluronics® F-68 AND polyoxyethylene (20) sorbitan monolaurate;
    Pluronics® F-68 AND polyoxyethylene (20) sorbitan monooleate;
    Pluronics® F-68 AND dioctyl sulfosuccinate sodium salt;
    Pluronics® F-68 AND polyethylene glycol (15)-hydroxystearate;
    Pluronics® F-127 AND vitamin-E-polyethylene glycol-succinate;
    Pluronics® F-127 AND sodium deoxycholate;
    Pluronics® F-127 AND polyoxyethylene (20) sorbitan monolaurate;
    Pluronics® F-127 AND polyoxyethylene (20) sorbitan monooleate;
    Pluronics® F-127 AND dioctyl sulfosuccinate sodium salt;
    Pluronics® F-127 AND polyethylene glycol (15)-hydroxystearate;
    polyvinyl alcohol AND vitamin-E-polyethylene glycol-succinate;

polyvinyl alcohol AND sodium deoxycholate;
polyvinyl alcohol AND polyoxyethylene (20) sorbitan monolaurate;
polyvinyl alcohol AND polyoxyethylene (20) sorbitan monooleate;
polyvinyl alcohol AND dioctyl sulfosuccinate sodium salt;
polyvinyl alcohol-polyethylene glycol graft copolymer AND vitamin-E-polyethylene glycol-succinate;
polyvinyl alcohol-polyethylene glycol graft copolymer AND sodium deoxycholate;
polyvinyl alcohol-polyethylene glycol graft copolymer AND polyoxyethylene (20) sorbitan monolaurate;
polyvinyl alcohol-polyethylene glycol graft copolymer AND dioctyl sulfosuccinate sodium salt;
polyethylene glycol k1 AND sodium deoxycholate;
polyethylene glycol k1 AND polyoxyethylene (20) sorbitan monolaurate;
polyethylene glycol k1 AND polyoxyethylene (20) sorbitan monooleate;
polyethylene glycol k1 AND dioctyl sulfosuccinate sodium salt;
polyethylene glycol k1 AND polyethylene glycol (15)-hydroxystearate;
hydroxylpropyl methyl cellulose AND vitamin-E-polyethylene glycol-succinate;
hydroxylpropyl methyl cellulose AND sodium deoxycholate;
hydroxylpropyl methyl cellulose AND polyoxyethylene (20) sorbitan monolaurate;
hydroxylpropyl methyl cellulose AND polyoxyethylene (20) sorbitan monooleate;
hydroxylpropyl methyl cellulose AND dioctyl sulfosuccinate sodium salt;
hydroxylpropyl methyl cellulose AND polyethylene glycol (15)-hydroxystearate;
polyvinylpyrrolidone k30 AND vitamin-E-polyethylene glycol-succinate;
polyvinylpyrrolidone k30 AND sodium deoxycholate;
polyvinylpyrrolidone k30 AND polyoxyethylene (20) sorbitan monolaurate;
polyvinylpyrrolidone k30 AND polyoxyethylene (20) sorbitan monooleate;
polyvinylpyrrolidone k30 AND dioctyl sulfosuccinate sodium salt; or
polyvinylpyrrolidone k30 AND polyethylene glycol (15)-hydroxystearate.

However, the following combinations of hydrophilic polymer(s) and surfactant(s) are particularly preferred for use in the present invention:
polyvinyl alcohol AND polyoxyethylene (20) sorbitan monolaurate;
Pluronics® F-127 AND vitamin-E-polyethylene glycol-succinate; hydroxylpropyl methyl cellulose AND N alkyldimethylbenzylammonium chloride; or
hydroxylpropyl methyl cellulose AND dioctyl sulfosuccinate sodium salt.

The one or more carrier materials are preferably water-soluble, such that they are dissolved and/or dispersed in an aqueous medium, and are able to form the outer layer around the individual cores of the prodrug of the present invention, i.e. around each nanoparticle of the prodrug of the present invention in the aqueous dispersions according to the invention. The aqueous medium may be, for example, sterile water.

The present invention also provides an aqueous dispersion, obtainable by, obtained by, or directly obtained by dispersing the solid composition as defined herein in an aqueous medium. Suitably, an aqueous dispersion is prepared immediately prior to use.

The present invention also provides an oily dispersion, obtainable by, obtained by, or directly obtained by dispersing the solid composition as defined herein in an oily medium. Suitably, an oily dispersion is prepared immediately prior to use.

When the composition is dispersed in the aqueous medium, the one or more carrier materials, e.g. providing the hydrophilic polymeric and surfactant activity, is/are dissolved within the aqueous medium to release the nanoparticles of the prodrug of the present invention in a dispersed form. The nanoparticles of the prodrug of the present invention, which were formerly dispersed within a mixture of the one or more selected carrier materials, then become dispersed within the aqueous medium in a form having an outer layer provided, whereby at least some of the cores of the prodrug of the present invention are each individually "coated" with the one or more selected carrier materials. Such an outer layer is thought to impart stability to the nanoparticles, thereby preventing premature coagulation and aggregation.

When the composition is dispersed in the oily medium, the one or more carrier materials, e.g. providing the hydrophilic polymeric and surfactant activity, may be dissolved within the oily medium to release the nanoparticles of the prodrug of the present invention in a dispersed form. The nanoparticles of the prodrug of the present invention, which were formerly dispersed within a solid mixture of the one or more selected carrier materials, then become dispersed within the oily medium. Such a physical form may form one end of a continuum within which the physical form of the oily dispersion falls; the other end of the continuum being that the composition is comminuted, e.g. by grinding, to form smaller particles of the composition (of the one or more carrier materials having nanoparticles of the prodrug of the present invention dispersed therein) which are dispersed in the oily medium such that the nanoparticles of the prodrug of the present invention remain trapped in the matrix, i.e. the matrix per se does not dissolve.

Suitably the relative amounts (including ratios) of the prodrug of the present invention, the carrier material(s) providing hydrophilic polymeric activity, and the carrier material(s) providing surfactant activity are the same as defined in relation to the composition. However, their respective wt % values in the dispersion as a whole must be adjusted to take account of the aqueous/oily medium. In a particular embodiment, the aqueous/oily medium comprises 20 to 99.5 wt % of the total dispersion. Preferably, or in a particular embodiment, the aqueous/oily medium may comprise 50 to 98 wt % of the total dispersion. Further preferably, or in a particular embodiment, the aqueous/oily medium may comprise 70 to 95 wt % of the total dispersion. Suitably, the remaining proportion of the dispersion consists essentially of the prodrug of the present invention and the one or more selected carrier materials, whose proportions within the dispersion as a whole are accordingly calculated (and scaled) by reference to the proportions recited in relation to the solid composition.

In a particular embodiment, the aqueous medium is water, preferably sterile water. In an alternative embodiment, the aqueous medium comprises water and one or more additional pharmaceutically acceptable diluents or excipients.

In a particular embodiment, the oily medium is a non-aqueous medium, selected from the group including: squalene; natural oils, such as triglycerides; mineral oils;

synthetic oils; vegetable oils, preferably avocado oil; rice bran oil; jojoba oil; Babassu oil; safflower seed oil; soybean oil; vitamin E; vitamin E acetate; non-vegetable oils such as silicone oils and paraffin oils; as well as waxes including carnauba wax, candelilla wax and lecithin. Mixtures of oils can be used. In an alternative embodiment, the oily medium is provided alongside one or more additional pharmaceutically acceptable diluents or excipients. In one particularly preferred embodiment, the oily medium is soybean oil.

Dispersions of the present invention are advantageously stable for prolonged periods, both in terms of chemical stability and the stability of the particles themselves (i.e. with respect to aggregation, coagulation, etc.).

Dispersions of the present invention may be considered as pharmaceutical compositions of the present invention. Thus, the dispersions of the present invention may be administered as is or further formulated with one or more additional excipients to provide a dispersion that is suitable for parenteral administration (for example, a sterile dispersion for intravenous, subcutaneous, intramuscular, or intraperitoneal dosing).

Dispersions of the present invention allow a measured aliquot to be taken therefrom for accurate dosing in a personalised medicine regime.

The particle size, polydispersity and zeta potential of the nanoparticles of the prodrug of the present invention in the dispersions is as defined hereinbefore in relation to the composition. It will of course be appreciated that the particle size, polydispersity and zeta potential nanoparticles of a prodrug, as described herein, present in the composition are measured by dispersing the composition in an aqueous medium to thereby form an aqueous dispersion of the present invention.

Process for Preparing an Aqueous Dispersion or an Oily Dispersion

The dispersion may be formed by methods well known in the art. For example, the prodrug of the present invention may be milled in the presence of an aqueous/oily mixture of the one or more selected carrier materials.

In a particular aspect of the invention, however, there is provided a process for preparing an aqueous dispersion, comprising dispersing a composition as defined herein in an aqueous medium.

In a particular embodiment, the aqueous medium is water. In an alternative embodiment, the aqueous medium comprises water and one or more additional excipients.

In a particular aspect of the invention, however, there is provided a process for preparing an oily dispersion, comprising dispersing a composition as defined herein in an oily medium.

Dispersing the solid composition in the aqueous/oily medium may comprise adding the solid composition to an aqueous/oily medium and suitably agitating the resulting mixture (e.g. by shaking, homogenisation, sonication, stirring, etc.).

Injectable Formulation of Prodrug Nanoparticles

The present invention also provides an intramuscularly-injectable formulation of nanoparticles of a prodrug of the present invention.

The present invention also provides a subcutaneously-injectable formulation of nanoparticles of a prodrug of the present invention.

Said formulations may be in solid form (or substantially solid form, e.g. a paste) or liquid form or semi-solid form, in which the prodrug is present in the form of nanoparticles. The nanoparticles of the prodrug may be dispersed within one or more carrier materials. When in liquid form, each nanoparticle of a prodrug of the present invention may be provided as a core around which an outer layer composed of the one or more carrier materials is provided.

Preferably, the one or more carrier materials may provide hydrophilic polymeric and surfactant activity, and further preferably may be selected from the group consisting of: Pluronics® F-68, Pluronics® F-127, polyvinyl alcohol (PVA), Kollicoat™, polyethylene glycol (PEG) k1 (Mw 1,000), hydroxylpropyl methyl cellulose (HPMC), polyvinylpyrrolidone k30 ('PVP k30'), Vitamin-E-polyethylene glycol-succinate (TPGS), sodium deoxycholate (NDC), polyoxyethylene (20) sorbitan monolaurate (Tween™ 20), polyoxyethylene (20) sorbitan monooleate (Tween™ 80), dioctyl sulfosuccinate sodium salt (AOT) and polyethylene glycol (15)-hydroxystearate (Solutol™ HS).

Accordingly, the one or more solid carrier material may be provided in any one or more of the following combinations:

Pluronics® F-68 AND vitamin-E-polyethylene glycol-succinate;
Pluronics® F-68 AND sodium deoxycholate;
Pluronics® F-68 AND polyoxyethylene (20) sorbitan monolaurate;
Pluronics® F-68 AND polyoxyethylene (20) sorbitan monooleate;
Pluronics® F-68 AND dioctyl sulfosuccinate sodium salt;
Pluronics® F-68 AND polyethylene glycol (15)-hydroxystearate;
Pluronics® F-127 AND vitamin-E-polyethylene glycol-succinate;
Pluronics® F-127 AND sodium deoxycholate;
Pluronics® F-127 AND polyoxyethylene (20) sorbitan monolaurate;
Pluronics® F-127 AND polyoxyethylene (20) sorbitan monooleate;
Pluronics® F-127 AND dioctyl sulfosuccinate sodium salt;
Pluronics® F-127 AND polyethylene glycol (15)-hydroxystearate;
polyvinyl alcohol AND vitamin-E-polyethylene glycol-succinate;
polyvinyl alcohol AND sodium deoxycholate;
polyvinyl alcohol AND polyoxyethylene (20) sorbitan monolaurate;
polyvinyl alcohol AND polyoxyethylene (20) sorbitan monooleate;
polyvinyl alcohol AND dioctyl sulfosuccinate sodium salt;
polyvinyl alcohol-polyethylene glycol graft copolymer AND vitamin-E-polyethylene glycol-succinate;
polyvinyl alcohol-polyethylene glycol graft copolymer AND sodium deoxycholate;
polyvinyl alcohol-polyethylene glycol graft copolymer AND polyoxyethylene (20) sorbitan monolaurate;
polyvinyl alcohol-polyethylene glycol graft copolymer AND dioctyl sulfosuccinate sodium salt;
polyethylene glycol k1 AND sodium deoxycholate;
polyethylene glycol k1 AND polyoxyethylene (20) sorbitan monolaurate;
polyethylene glycol k1 AND polyoxyethylene (20) sorbitan monooleate;
polyethylene glycol k1 AND dioctyl sulfosuccinate sodium salt;
polyethylene glycol k1 AND polyethylene glycol (15)-hydroxystearate;
hydroxylpropyl methyl cellulose AND vitamin-E-polyethylene glycol-succinate;

hydroxylpropyl methyl cellulose AND sodium deoxycholate;
hydroxylpropyl methyl cellulose AND polyoxyethylene (20) sorbitan monolaurate;
hydroxylpropyl methyl cellulose AND polyoxyethylene (20) sorbitan monooleate;
hydroxylpropyl methyl cellulose AND dioctyl sulfosuccinate sodium salt;
hydroxylpropyl methyl cellulose AND polyethylene glycol (15)-hydroxystearate;
polyvinylpyrrolidone k30 AND vitamin-E-polyethylene glycol-succinate;
polyvinylpyrrolidone k30 AND sodium deoxycholate;
polyvinylpyrrolidone k30 AND polyoxyethylene (20) sorbitan monolaurate;
polyvinylpyrrolidone k30 AND polyoxyethylene (20) sorbitan monooleate;
polyvinylpyrrolidone k30 AND dioctyl sulfosuccinate sodium salt; or
polyvinylpyrrolidone k30 AND polyethylene glycol (15)-hydroxystearate.

However, the following combinations of hydrophilic polymer(s) and surfactant(s) are particularly preferred for use in the present invention:
polyvinyl alcohol AND polyoxyethylene (20) sorbitan monolaurate;
Pluronics® F-127 AND vitamin-E-polyethylene glycol-succinate;
hydroxylpropyl methyl cellulose AND N alkyldimethylbenzylammonium chloride; or
hydroxylpropyl methyl cellulose AND dioctyl sulfosuccinate sodium salt.

The injectable formulations of nanoparticles of a prodrug of the present invention are advantageously designed for administration as a depot injection, so as to overcome the aforementioned problems associated with poor-adherence to prophylaxis and/or treatment, especially in respect of HIV or cancer, and the consequences that ensue. Furthermore, a depot injection is beneficial is that it may be easier to administer than conventional preparations and allows for simpler follow-up/on-going care.

Preferably, the injectable formulation of nanoparticles of a prodrug of the present invention provide a controlled release bolus formulation of the prodrug, which, when administered to a patient (via intramuscular or subcutaneous injection), releases the prodrug into the bloodstream of the patient over a period of at least about two weeks from the date of administration. Further preferably the period of release is at least about three weeks, yet further preferably at least about one month, more preferably at least about three months, and most preferably at least about six months, from the date of administration of the injection.

The prodrug compounds of the present invention may be in solid form (or substantially solid form, e.g. a paste) or liquid form or semi-solid form. Preferably, the prodrug compounds of the present invention may be semi-solid. For the avoidance of any doubt, throughout this specification by "semi-solid" and like terms it is meant that the state of matter in which the substance in question (i.e. prodrug compound) exhibits gel or wax like characteristics at a temperature above its solidification temperature but at or below of 40° C.

The prodrug compounds of the present invention may have a log P value of at least about 1. In other embodiments of the present invention, the prodrug compounds may have a log P value of at least about 2 or of at least about 3. In further embodiments, the prodrug compounds of the present invention may have a log P value of from about 1 to about 10, from about 3 to about 8, from about 5 to about 8, from about 6 to about 8, from about 4 to about 7, from about 4 to about 6, from about 3 to about 6 or from about 3 to about 5. Preferably, the prodrug compounds of the present invention may have a log P value of at least about 1 to about 3, more preferably of at least about 1 to about 2 or at least about 2 to about 3.

The prodrug compounds of the present invention may have a log P value of at least 1 greater than the log P value of the pharmaceutically active agent. In another embodiment, the prodrug compounds of the present invention may have a log P value of at least from about 2 to 10 greater than the pharmaceutically active agent. In a further embodiment, the prodrug compounds of the present invention may have a log P value of at least from about 4 to 8 greater than the log P of the pharmaceutically active agent.

Prodrug Compounds

In the present invention, the prodrug compounds may be defined according to formula (I) and pharmaceutically acceptable derivatives thereof.

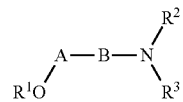

(I)

Wherein the respective substituent groups (A, B, $R^1$, $R^2$ and $R^3$) may be as defined in any of the aspects and embodiments described herein.

Various embodiments of the prodrug compounds of formula (I) are described in this application. It should also be understood below that where an embodiment of a compound of any of this formula is further defined (i.e. by reference to the respective substituent groups), the definition also applies to pharmaceutically acceptable derivatives of the respective compounds. It is intended that features specified in each of these embodiments may be combined with other features specified in other embodiments to provide further embodiments of the invention. The skilled person will also appreciate that any chemically impossible compounds that would result from combining one of more of the embodiments below are not intended to be encompassed within the context of this invention.

A Group

In the present invention A may be a linker with a chain length having an integer of from 1 to 10 atoms. In embodiments, the linker may be a optionally substituted —$C_{1-10}$alkyl linker, optionally substituted —$C_{2-10}$heteroalkyl linker, optionally substituted —$C_{3-6}$cycloalkyl linker, optionally substituted —$C_{3-6}$heterocycloalkyl linker, optionally substituted —$C_{2-6}$alkenyl linker, optionally substituted —$C_{2-6}$heteroalkenyl linker, optionally substituted —$C_{3-6}$cycloalkenyl linker, optionally substituted —$C_{3-6}$heterocycloalkenyl linker, optionally substituted —$C_{2-6}$alkynyl linker, optionally substituted —$C_{2-6}$heteroalkynyl linker, optionally substituted —$C_{6-14}$aryl linker or optionally substituted —$C_{5-14}$heteroaryl linker.

In other embodiments, A may be a linker according to formula (II):

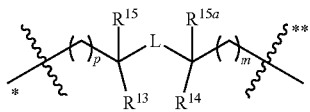

The symbol (*) may denote the point of attachment to R¹O and () may denote the point of attachment to B. In alternative embodiments, the symbol () may denote the point of attachment to R¹O and (*) may denote the point of attachment to B In the present invention, L may be —O, —NR$^{L1}$, —S or —CR$^{L2}$R$^{L3}$. Preferably, L may be —O, —S or —CH$_2$. Even more preferably, L may be —O or —CH$_2$.

In further embodiments, A may be an optionally substituted —C$_{3-6}$cycloalkyl linker, optionally substituted —C$_{3-6}$heterocycloalkyl linker, optionally substituted —C$_{1-6}$cycloalkenyl linker or optionally substituted —C$_{3-6}$ heterocycloalkenyl linker. Typically, A may be an optionally substituted

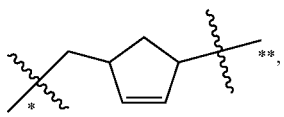 [SMILES: *CC1C=CC(*)C1]

optionally substituted

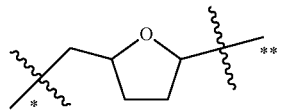 [SMILES: *CC1CCC(*)O1]

or optionally substituted

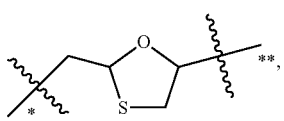 [SMILES: *CC1OC(*)CS1]

wherein (*) denotes the point of attachment to R¹O and (**) denotes the point of attachment to B.

Groups R$^{13}$, R$^{14}$, R$^{15}$ and R$^{15a}$

In the compounds of the present invention, R$^{13}$, R$^{14}$, R$^{15}$ and R$^{15a}$ may be each independently selected from —H, optionally substituted —C$_{1-6}$alkyl, optionally substituted —C$_{2-6}$heteroalkyl, optionally substituted —C$_{3-6}$cycloalkyl, optionally substituted —C$_{3-6}$heterocycloalkyl, optionally substituted —C$_{2-6}$alkenyl, optionally substituted —C$_{2-6}$heteroalkenyl, optionally substituted —C$_{3-6}$cycloalkenyl, optionally substituted —C$_{3-6}$heterocycloalkenyl, optionally substituted —C$_{2-6}$alkynyl, optionally substituted —C$_{2-6}$heteroalkynyl, optionally substituted —C$_{6-14}$aryl or optionally substituted —C$_{5-14}$heteroaryl.

In embodiments, R$^{13}$ and R$^{14}$ may be taken together with the carbons to which they are attached to form an optionally substituted —C$_{3-10}$cycloalkyl, optionally substituted —C$_{3-10}$heterocycloalkyl, optionally substituted —C$_{3-10}$cycloalkenyl, optionally substituted —C$_{3-10}$heterocycloalkenyl, substituted —C$_{6-14}$aryl or optionally substituted —C$_{5-14}$heteroaryl. Typically, R$^{13}$ and R$^{14}$ may be taken together with the carbons to which they are attached to form an optionally substituted —C$_{3-10}$cycloalkyl, optionally substituted —C$_{3-10}$heterocycloalkyl or optionally substituted —C$_{3-10}$cycloalkenyl.

In embodiments, R$^{15}$ and R$^{15a}$ may be each independently selected from —H, optionally substituted —C$_{1-6}$alkyl, optionally substituted —C$_{2-6}$heteroalkyl, optionally substituted —C$_{2-6}$alkenyl, optionally substituted —C$_{2-6}$heteroalkenyl, optionally substituted —C$_{2-6}$alkynyl or optionally substituted —C$_{2-6}$heteroalkynyl. Typically, R$^{15}$ and R$^{15a}$ may be —H, optionally substituted —C$_{1-6}$alkyl or optionally substituted —C$_{2-6}$alkynyl. Preferably, R$^{15a}$ may be —H.

Groups R$^{L1}$, R$^{L2}$ and R$^{L3}$

In compounds of the present invention R$^{L1}$, R$^{L2}$ and R$^{L3}$ may be each independently selected from —H, optionally substituted —C$_{1-6}$alkyl, optionally substituted —C$_{2-6}$heteroalkyl, optionally substituted —C$_{3-6}$cycloalkyl, optionally substituted —C$_{3-6}$heterocycloalkyl, optionally substituted —C$_{2-6}$alkenyl, optionally substituted —C$_{2-6}$heteroalkenyl, optionally substituted —C$_{3-6}$cycloalkenyl, optionally substituted —C$_{3-6}$heterocycloalkenyl, optionally substituted —C$_{2-6}$alkynyl, optionally substituted —C$_{2-6}$heteroalkynyl, optionally substituted —C$_{6-14}$aryl or optionally substituted —C$_{5-14}$heteroaryl. In typical embodiments, R$^{L1}$, R$^{L2}$ and R$^{L3}$ may be —H or optionally substituted —C$_{1-6}$alkyl. In other embodiments R$^{L1}$, R$^{L2}$ and R$^{L3}$ may be —CH$_3$.

m and p Groups

In the present invention, group m and p may be each independently selected as integers from 0, 1, 2, 3, 4 or 5. Typically, m may be 0 and p may be 1. In other embodiments, m may be 1 and p may be 0. In yet further embodiments, m may be 0 and p may be 1, 2 or 3.

B Group

In compounds of the present invention, B may be an optionally substituted —C$_{5-14}$heteroaryl. In embodiments, B may be purine analogue according to the formula (III) or pyrimidine analogue according to the formula (IV):

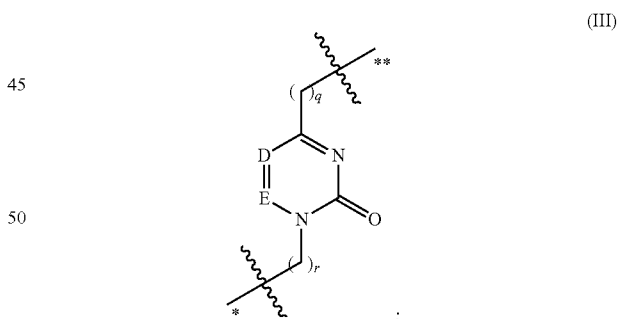

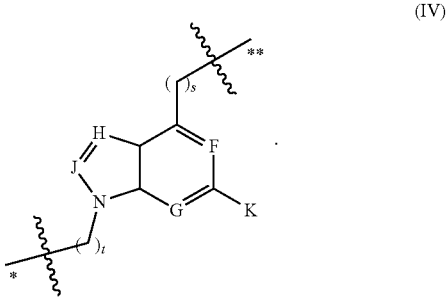

In embodiments, symbol (*) may denote the point of attachment to A and (**) may denotes the point of attachment to NR²R³. In alternative embodiments, symbol (*) may denote the point of attachment to NR²R³ and (**) may denotes the point of attachment to A.

D, E, F, G, H and J Groups

In compounds of the present invention D, E, F, G, H and J may be each independently selected from —CH, —N, —CF, —CCl, —CBr, —CR$^{16}$, —CNR$^{16a}$R$^{16b}$, —COR$^{16c}$ or —CSR$^{16d}$. In embodiments, D, E, F, G, H and J may be each independently selected from —CH, —N or —CF. Preferably, where D is —CF, E may be —CH. In other embodiments, where F, G and H are —N, J may be —CH.

K Group

In compounds of the present invention K may be —H, halogen, optionally substituted —C$_{1-6}$haloalkyl, —OR$^{17}$, —NR$^{17a}$R$^{17b}$, —NO$_2$, —CN, optionally substituted —C$_{1-6}$alkyl, optionally substituted —C$_{2-6}$heteroalkyl, optionally substituted —C$_{3-6}$cycloalkyl, optionally substituted —C$_{3-6}$heterocycloalkyl, optionally substituted —C$_{2-6}$alkenyl, optionally substituted —C$_{2-6}$heteroalkenyl, optionally substituted —C$_{3-6}$cycloalkenyl, optionally substituted —C$_{3-6}$heterocycloalkenyl, optionally substituted —C$_{2-6}$alkynyl, optionally substituted —C$_{2-6}$heteroalkynyl, optionally substituted —C$_{6-14}$aryl or optionally substituted —C$_{5-14}$heteroaryl. Typically, K may be —H or NH$_2$.

Groups R$^{16}$, R$^{16a}$, R$^{16b}$, R$^{16c}$, R$^{16d}$, R$^{17}$, R$^{17a}$ and R$^{17b}$ In compounds of the present invention R$^{16}$, R$^{16a}$, R$^{16b}$, R$^{16c}$, R$^{16d}$, R$^{17}$, R$^{17a}$ and R$^{17b}$ may be each independently selected from —H, optionally substituted —C$_{1-6}$alkyl, optionally substituted —C$_{2-6}$heteroalkyl, optionally substituted —C$_{3-6}$cycloalkyl, optionally substituted —C$_{3-6}$heterocycloalkyl, optionally substituted —C$_{2-6}$alkenyl, optionally substituted —C$_{2-6}$heteroalkenyl, optionally substituted —C$_{3-6}$cycloalkenyl, optionally substituted —C$_{3-6}$heterocycloalkenyl, optionally substituted —C$_{2-6}$alkynyl, optionally substituted —C$_{2-6}$heteroalkynyl, optionally substituted —C$_{6-14}$aryl or optionally substituted —C$_{5-14}$heteroaryl. In embodiments R$^{16}$, R$^{16a}$, R$^{16b}$, R$^{16c}$, R$^{16d}$, R$^{17}$, R$^{17a}$ and R$^{17b}$ may be each independently selected from —H, optionally substituted —C$_{1-6}$alkyl, optionally substituted —C$_{2-6}$heteroalkyl. Preferably, R$^{16}$, R$^{16a}$, R$^{16b}$, R$^{16c}$, R$^{16d}$, R$^{17}$, R$^{17a}$ and R$^{17b}$ may be may be each independently selected from —H or optionally substituted —C$_{1-6}$alkyl.

q, r, s and t Groups

In compounds of the present invention q, r, s and t may be each independently selected as integers from 0, 1, 2, 3, 4 or 5. Typically, q, r, s and t may be 0 or 1. Preferably, q, r, s and t may be 0.

Group R$^1$

In compounds of the present invention R$^1$ may be —H, optionally substituted —C$_{1-6}$alkyl, optionally substituted —C$_{2-6}$heteroalkyl, optionally substituted —C$_{3-6}$cycloalkyl, optionally substituted —C$_{3-6}$heterocycloalkyl, optionally substituted —C$_{2-6}$alkenyl, optionally substituted —C$_{2-6}$heteroalkenyl, optionally substituted —C$_{3-6}$cycloalkenyl, optionally substituted —C$_{3-6}$heterocycloalkenyl, optionally substituted —C$_{2-6}$alkynyl, optionally substituted —C$_{2-6}$heteroalkynyl, optionally substituted —C$_{6-14}$aryl or optionally substituted —C$_{5-14}$heteroaryl, optionally substituted —C(=O)C$_{1-20}$alkyl, optionally substituted —CO$_2$C$_{1-20}$alkyl, optionally substituted —C(=O)NHC$_{1-20}$alkyl, optionally substituted —C(=O)N(C$_{1-20}$alkyl)$_2$; optionally substituted —P(=O)OR$^4$OR$^5$, optionally substituted P(=O)OR$^6$R$^7$, optionally substituted —(CH$_2$)$_n$P(=O)OR$^8$OR$^9$, optionally substituted —(CH)$_n$P(=O)OR$^{10}$NHR$^{11}$, optionally substituted —SiR$^{Si1}$R$^{Si2}$R$^{Si3}$, optionally substituted

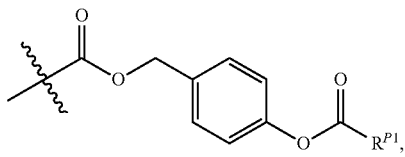

optionally substituted

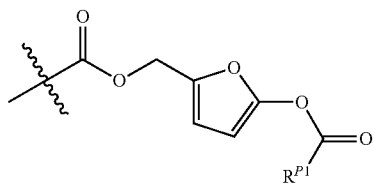

or optionally substituted

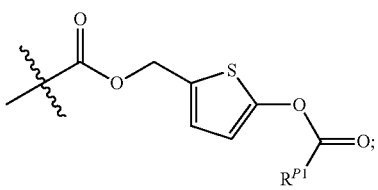

In some embodiments, R$^1$ may be optionally substituted —C(=O)C$_{1-20}$alkyl, optionally substituted —CO$_2$C$_{1-20}$alkyl, optionally substituted —C(=O)NHC$_{1-20}$alkyl, optionally substituted —C(=O)N(C$_{1-20}$alkyl)$_2$; optionally substituted —P(=O)OR$^4$OR$^5$, optionally substituted —P(=O)OR$^6$R$^7$, optionally substituted —(CH$_2$)$_n$P(=O)OR$^8$OR$^9$ or optionally substituted —(CH)$_n$P(=O)OR$^{10}$NHR$^{11}$ or optionally substituted —SiR$^{Si1}$R$^{Si2}$R$^{Si3}$. In other embodiments, R$^1$ may be optionally substituted —C(=O)C$_{1-20}$alkyl, optionally substituted —CO$_2$C$_{1-20}$alkyl, optionally substituted —C(=O)NHC$_{1-20}$alkyl or optionally substituted —C(=O)N(C$_{1-20}$alkyl)$_2$. Preferably, R$^1$ may be —H, optionally substituted —C(=O)C$_{1-8}$alkyl, optionally substituted —CO$_2$C$_{1-8}$alkyl; optionally substituted —(CH$_2$)$_n$P(=O)OR$^8$OR$^9$ or optionally substituted —(CH)$_n$P(=O)OR$^{10}$NHR$^{11}$. In other embodiments, R$^1$ may be —H, optionally substituted —C(=O)C$_{4-8}$alkyl or optionally substituted —CO$_2$C$_{4-8}$alkyl. In further embodiments, R$^1$ may be —H, optionally substituted —C(=O)C$_{1-4}$alkyl or optionally substituted —CO$_2$C$_{1-4}$alkyl.

In some embodiments R$^1$ may be

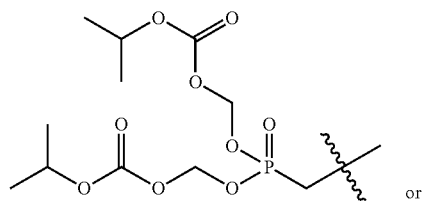

or

-continued

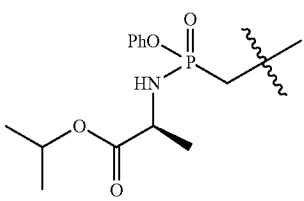

Groups $R^4$ to $R^{11}$ and $R^{Si1}$ to $R^{Si3}$

In compounds of the present invention $R^4$ to $R^{11}$ and $R^{Si1}$ to $R^{Si3}$ may be each independently selected from —H, optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl.

Group $R^{P1}$

In compounds of the present invention $R^{P1}$ may be selected from optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl.

n Group

In compounds of the present invention n may be an integer selected from 1, 2, 3, 4 or 5. Typically n may be 0, 1 or 2. Preferably, n may be 1.

Groups $R^2$ and $R^3$

In compounds of the present invention $R^2$ and $R^3$ are each independently selected from —H, optionally substituted —C(=O)$C_{1-20}$alkyl, optionally substituted —C(=O)$C_{6-14}$aryl, optionally substituted —C(=O)$C_{5-14}$heteroaryl, optionally substituted —$CO_2C_{1-20}$alkyl, optionally substituted —$CO_2C_{6-14}$aryl, optionally substituted —$CO_2C_{5-14}$heteroaryl, optionally substituted —C(=O)NH$C_{1-20}$alkyl, optionally substituted —C(=O)NH$C_{6-14}$aryl, optionally substituted —C(=O)NH$C_{5-14}$heteroaryl, optionally substituted =$CR^{12}NR^{12a}R^{12b}$ an optionally substituted trimethyl lock analogue,

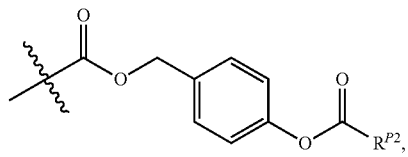

optionally substituted

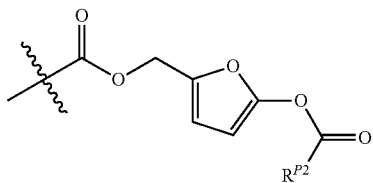

or optionally substituted

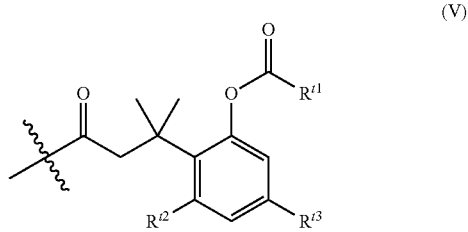

wherein at least one of $R^2$ or $R^3$ is not —H.

In embodiments, $R^2$ may be —H, optionally substituted —C(=O)$C_{1-8}$alkyl, optionally substituted —$CO_2C_{1-8}$alkyl or optionally substituted —C(=O)NH$C_{1-8}$alkyl. In other embodiments, $R^2$ may be —H, optionally substituted —C(=O)$C_{4-8}$alkyl, optionally substituted —$CO_2C_{4-8}$alkyl or optionally substituted —C(=O)NH$C_{4-8}$alkyl.

In other embodiments, $R^3$ may be —H, optionally substituted —C(=O)$C_{1-8}$alkyl, optionally substituted —$CO_2C_{1-8}$alkyl or optionally substituted —C(=O)NH$C_{1-8}$ alkyl. In other embodiments, $R^3$ may be —H, optionally substituted —C(=O)$C_{4-8}$alkyl, optionally substituted —$CO_2C_{4-8}$alkyl or optionally substituted —C(=O)NH$C_{4-8}$ alkyl.

In further embodiments, when $R^2$ is optionally substituted —C(=O)$C_{1-20}$alkyl, optionally substituted —$CO_2C_{1-20}$alkyl, optionally substituted —C(=O)NH$C_{1-20}$alkyl, optionally substituted =$CR^{12}NR^{12a}R^{12b}$ or an optionally substituted trimethyl lock analogue, $R^3$ may be —H.

In some embodiments, the optionally substituted trimethyl lock analogue may be according to the formula (V):

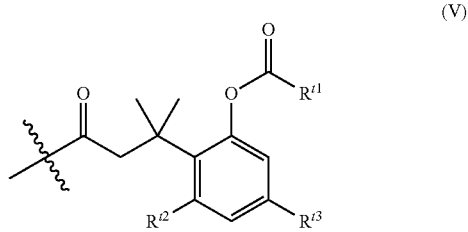

(V)

In still further embodiments, when $R^2$ is optionally substituted —C(=O)$C_{1-8}$alkyl, optionally substituted —$CO_2C_{1-8}$alkyl or optionally substituted —C(=O)NH$C_{1-8}$ alkyl, $R^3$ may be H. In yet further embodiments, when $R^2$ is optionally substituted —C(=O)$C_{4-8}$alkyl, optionally substituted —$CO_2C_{4-8}$alkyl or optionally substituted —C(=O) NH$C_{4-8}$alkyl, $R^3$ may be H.

In embodiments, when $R^2$ is a trimethyl lock analogue, $R^3$ may be H. In other embodiments, when $R^2$ is

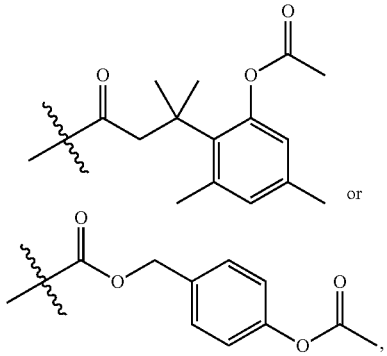

$R^3$ may be H.

$R^{12}$, $R^{12a}$ and $R^{12b}$ Groups

In compounds of the present invention $R^{12}$, $R^{12a}$ and $R^{12b}$ may be each independently selected from —H, optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl. In embodiments, when $R^{12}$ is —H or optionally substituted —$C_{1-6}$alkyl, $R^{12a}$ and $R^{12b}$ may optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl. Preferably, when $R^{12}$ is —H, $R^{12a}$ and $R^{12b}$ may be optionally substituted —$C_{1-6}$alkyl.

Group $R^{P2}$

In compounds of the present invention $R^{P2}$ may be selected from optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl.

$R^{t1}$, $R^{t2}$ and $R^{t3}$ Groups

In compounds of the present invention $R^{t1}$, $R^{t2}$ and $R^{t3}$ may be each independently selected from —H, optionally substituted —$C_{1-6}$alkyl, optionally substituted —$C_{2-6}$heteroalkyl, optionally substituted —$C_{3-6}$cycloalkyl, optionally substituted —$C_{3-6}$heterocycloalkyl, optionally substituted —$C_{2-6}$alkenyl, optionally substituted —$C_{2-6}$heteroalkenyl, optionally substituted —$C_{3-6}$cycloalkenyl, optionally substituted —$C_{3-6}$heterocycloalkenyl, optionally substituted —$C_{2-6}$alkynyl, optionally substituted —$C_{2-6}$heteroalkynyl, optionally substituted —$C_{6-14}$aryl or optionally substituted —$C_{5-14}$heteroaryl.

Stereochemistry

In some embodiments, when A is a linker according to formula (II) and where $R^{13}$ and $R^{14}$ may be taken together with the carbons to which they are attached to form an optionally substituted —$C_{3-10}$cycloalkyl, optionally substituted —$C_{3-10}$heterocycloalkyl, optionally substituted —$C_{3-10}$cycloalkenyl, optionally substituted —$C_{3-10}$heterocycloalkenyl, the stereochemistry of the centre to which $R^{13}$ and $R^{14}$ are bonded to may be S or R. In embodiments the stereochemistry of the centre to which $R^{13}$ is bonded may be R. In other embodiments, the stereochemistry of the centre to which $R^{14}$ is bonded may be S. In further embodiments, the stereochemistry of the centre to which $R^{13}$ and $R^{14}$ are bonded to may both be S. In yet further embodiments, the stereochemistry of the centre to which $R^{13}$ and $R^{14}$ are bonded to may both be R. Preferably, the stereochemistry of the centre to which $R^{13}$ is bonded may be R and the stereochemistry of the centre to which $R^{14}$ may be S. All enantiomeric and diastereomeric embodiments are intended to be encompassed by the present invention. Individual enantiomeric/diastereoisomers are included within the scope of the invention. Mixtures of isomers, e.g. racemic mixtures and/or diastereomeric mixtures may also be provided.

Substituents

Optionally substituted groups of the compounds of the invention (e.g. alkyl, cycloalkyl, alkoxy, alkenyl, cycloalkenyl, alkynyl, alkylene, alkenylene, heteroalkyl, heterocycloalkyl, heteroalkenyl, heterocycloalkenyl, heteroalkynyl, heteroalkylene, heteroalkenylene, aryl, arylalkyl, arylheteroalkyl, heteroaryl, heteroarylalkyl or heteroarylheteroalkyl groups, etc.) may be substituted or unsubstituted, for instance unsubstituted. Typically, substitution involves the notional replacement of a hydrogen atom with a substituent group, or two hydrogen atoms in the case of substitution by =O.

Where substituents are present, there may, for instance, be from 1 to 6 substituents, depending on the available substituent positions of the group. Typically there will be from 1 to 3 substituents, in embodiments 1 or 2 substituents, such as only 1 substituent.

In such embodiments, the optional substituent(s) is/are independently halogen, $C_{1-6}$haloalkyl (e.g. trihalomethyl, trihaloethyl), —OH, —$NH_2$, —$NO_2$, —CN, —$N^+(C_{1-6}$alkyl$)_2O^-$, —$CO_2H$, —$CO_2C_{1-6}$alkyl, —$SO_3H$, —$OSO_3H$, —$OSO_3C_{1-6}$alkyl, —$NHSO_3H$, —$NHSO_3C_{1-6}$alkyl, —$N(C_{1-6}$alkyl$)SO_3H$, —$N(C_{1-6}$alkyl$)SO_3C_{1-6}$alkyl, —$SOC_{1-6}$alkyl, —$SO_2C_{1-6}$alkyl, —$SO_3C_{1-6}$alkyl, —OC(=O)O$C_{1-6}$alkyl, —C(=O)H, —C(=O)$C_{1-6}$alkyl, —OC(=O)$C_{1-6}$alkyl, =O, —N($C_{1-6}$alkyl$)_2$, —C(=O)$NH_2$, —C(=O)N($C_{1-6}$alkyl$)_2$, —N($C_{1-6}$alkyl)C(=O)O($C_{1-6}$alkyl), —N($C_{1-6}$alkyl)C(=O)N($C_{1-6}$alkyl$)_2$, —OC(=O)N($C_{1-6}$alkyl$)_2$, —N($C_{1-6}$alkyl)C(=O)$C_{1-6}$alkyl, —C(=S)N($C_{1-6}$alkyl$)_2$, —N($C_{1-6}$alkyl)C(=S)$C_{1-6}$alkyl, —$SO_2$N($C_{1-6}$alkyl$)_2$, —N($C_{1-6}$alkyl)$SO_2C_{1-6}$alkyl, —N($C_{1-6}$alkyl)C(=S)N($C_{1-6}$alkyl$)_2$, —N($C_{1-6}$alkyl)$SO_2$N($C_{1-6}$alkyl$)_2$, —$C_{1-6}$alkyl, —$C_{2-6}$heteroalkyl, —$C_{3-6}$cycloalkyl, —$C_{3-6}$heterocycloalkyl, —$C_{2-6}$alkenyl, —$C_{2-6}$heteroalkenyl, —$C_{3-6}$cycloalkenyl, —$C_{3-6}$heterocycloalkenyl, —$C_{2-6}$alkynyl, —$C_{2-6}$heteroalkynyl, —$Z^u$—$C_{1-6}$alkyl, —$Z^u$—$C_{3-6}$cycloalkyl, —$Z^u$—$C_{2-6}$alkenyl, —$Z^u$—$C_{3-6}$cycloalkenyl or —$Z^u$—$C_{2-6}$alkynyl, wherein $Z^u$ is independently O, S, NH or N($C_{1-6}$alkyl).

In another embodiment, the optional substituent(s) is/are independently halogen, trihalomethyl, trihaloethyl, —$OSO_3H$, —$OSO_3C_{1-6}$alkyl, —$NHSO_3H$, —$NHSO_3C_{1-6}$alkyl, —$N(C_{1-6}$alkyl$)SO_3H$, —$N(C_{1-6}$alkyl$)SO_3C_{1-6}$alkyl, —OH, —$NH_2$, —$NO_2$, —CN, —$N^+(C_{1-6}$alkyl$)_2O^-$, —CO$_2$H, —SOC$_{1-6}$alkyl, —SO$_2$C$_{1-6}$alkyl, —C(=O)C$_{1-6}$alkyl, =O, —N(C$_{1-6}$alkyl)$_2$, —C(=O)NH$_2$, —C$_{1-6}$alkyl, —C$_{3-6}$cycloalkyl, —C$_{3-6}$heterocycloalkyl, —Z$^u$C$_{1-6}$alkyl or —Z$^u$—C$_{3-6}$cycloalkyl, wherein Z$^u$ is defined above.

Preferably, the optional substituent(s) is/are independently halogen, trihalomethyl, —OH, —CO$_2$H, —SO$_3$H, —OSO$_3$H, —NHSO$_3$C$_{1-6}$alkyl, —SOC$_{1-6}$alkyl, —SO$_2$C$_{1-6}$alkyl, —C(=O)C$_{1-6}$alkyl, =O, —C$_{1-6}$alkyl, —C$_{3-6}$cycloalkyl, —C$_{3-6}$heterocycloalkyl, —Z$^u$C$_{1-6}$alkyl or —Z$^u$—C$_{3-6}$cycloalkyl, wherein Z$^u$ is defined above.

Specific Compounds

The invention provides the following specific compounds:

methyl (5-fluoro-1-((2R,5S)-2-(((methoxycarbonyl)oxy)methyl)-1,3-oxathiolan-5-yl)-2-oxo-1,2-dihydropyrimidin-4-yl)carbamate;

ethyl (1-((2R,5S)-2-(((ethoxycarbonyl)oxy)methyl)-1,3-oxathiolan-5-yl)-5-fluoro-2-oxo-1,2-dihydropyrimidin-4-yl)carbamate;

propyl (5-fluoro-2-oxo-1-((2R,5S)-2-(((propoxycarbonyl)oxy)methyl)-1,3-oxathiolan-5-yl)-1,2-dihydropyrimidin-4-yl)carbamate;

butyl (1-((2R,5S)-2-(((butoxycarbonyl)oxy)methyl)-1,3-oxathiolan-5-yl)-5-fluoro-2-oxo-1,2-dihydropyrimidin-4-yl)carbamate;

pentyl (5-fluoro-2-oxo-1-((2R,5S)-2-((((pentyloxy)carbonyl)oxy)methyl)-1,3-oxathiolan-5-yl)-1,2-dihydropyrimidin-4-yl)carbamate;

hexyl (5-fluoro-1-((2R,5S)-2-((((hexyloxy)carbonyl)oxy)methyl)-1,3-oxathiolan-5-yl)-2-oxo-1,2-dihydropyrimidin-4-yl)carbamate;

heptyl (5-fluoro-1-((2R,5S)-2-((((heptyloxy)carbonyl)oxy)methyl)-1,3-oxathiolan-5-yl)-2-oxo-1,2-dihydropyrimidin-4-yl)carbamate;

octyl (5-fluoro-1-((2R,5S)-2-((((octyloxy)carbonyl)oxy)methyl)-1,3-oxathiolan-5-yl)-2-oxo-1,2-dihydropyrimidin-4-yl)carbamate;

methyl (5-fluoro-1-((2R,5S)-2-(hydroxymethyl)-1,3-oxathiolan-5-yl)-2-oxo-1,2-dihydropyrimidin-4-yl)carbamate;

ethyl (5-fluoro-1-((2R,5S)-2-(hydroxymethyl)-1,3-oxathiolan-5-yl)-2-oxo-1,2-dihydropyrimidin-4-yl)carbamate;

propyl (5-fluoro-1-((2R,5S)-2-(hydroxymethyl)-1,3-oxathiolan-5-yl)-2-oxo-1,2-dihydropyrimidin-4-yl)carbamate;

butyl (5-fluoro-1-((2R,5S)-2-(hydroxymethyl)-1,3-oxathiolan-5-yl)-2-oxo-1,2-dihydropyrimidin-4-yl)carbamate;

pentyl (5-fluoro-1-((2R,5S)-2-(hydroxymethyl)-1,3-oxathiolan-5-yl)-2-oxo-1,2-dihydropyrimidin-4-yl)carbamate;

hexyl (5-fluoro-1-((2R,5S)-2-(hydroxymethyl)-1,3-oxathiolan-5-yl)-2-oxo-1,2-dihydropyrimidin-4-yl)carbamate;

heptyl (5-fluoro-1-((2R,5S)-2-(hydroxymethyl)-1,3-oxathiolan-5-yl)-2-oxo-1,2-dihydropyrimidin-4-yl)carbamate;

octyl (5-fluoro-1-((2R,5S)-2-(hydroxymethyl)-1,3-oxathiolan-5-yl)-2-oxo-1,2-dihydropyrimidin-4-yl)carbamate;

((2R,5S)-5-(5-fluoro-2-oxo-4-(((pentyloxy)carbonyl)amino)pyrimidin-1(2H)-yl)-1,3-oxathiolan-2-yl)methyl acetate;

((2R,5S)-5-(5-fluoro-4-(((hexyloxy)carbonyl)amino)-2-oxopyrimidin-1(2H)-yl)-1,3-oxathiolan-2-yl)methyl acetate;

((2R,5S)-5-(5-fluoro-4-(((heptyloxy)carbonyl)amino)-2-oxopyrimidin-1(2H)-yl)-1,3-oxathiolan-2-yl)methyl acetate;

((2R,5S)-5-(5-fluoro-4-(((octyloxy)carbonyl)amino)-2-oxopyrimidin-1(2H)-yl)-1,3-oxathiolan-2-yl)methyl acetate;

((2R,5S)-5-(5-fluoro-4-(((octyloxy)carbonyl)amino)-2-oxopyrimidin-1(2H)-yl)-1,3-oxathiolan-2-yl)methyl isobutyrate;

((2R,5S)-5-(5-fluoro-2-oxo-4-(((pentyloxy)carbonyl)amino)pyrimidin-1(2H)-yl)-1,3-oxathiolan-2-yl)methyl butyrate;

(Z)—N'-(5-fluoro-1-((2R,5S)-2-(hydroxymethyl)-1,3-oxathiolan-5-yl)-2-oxo-1,2-dihydropyrimidin-4-yl)-N,N-dimethylformimidamide;

2-(4-((1-((2R,5S)-2-(((tert-butyldimethylsilyl)oxy)methyl)-1,3-oxathiolan-5-yl)-5-fluoro-2-oxo-1,2-dihydropyrimidin-4-yl)amino)-2-methyl-4-oxobutan-2-yl)-3,5-dimethylphenyl acetate;

2-(4-((5-fluoro-1-((2R,5S)-2-(hydroxymethyl)-1,3-oxathiolan-5-yl)-2-oxo-1,2-dihydropyrimidin-4-yl)amino)-2-methyl-4-oxobutan-2-yl)-3,5-dimethylphenyl acetate;

(2S)-isopropyl (((((R)-1-(6-(3-(2-acetoxy-4,6-dimethylphenyl)-3-methylbutanamido)-9H-purin-9-yl)propan-2-yl)oxy)methyl)(phenoxy)phosphoryl)-L-alaninate;

4-(((((2R,5S)-5-(4-((((4-acetoxybenzyl)oxy)carbonyl)amino)-5-fluoro-2-oxopyrimidin-1(2H)-yl)-1,3-oxathiolan-2-yl)methoxy)carbonyl)oxy)methyl)phenyl acetate and pharmaceutically acceptable derivatives thereof.

Chemical Groups

Halo

The term "halogen" (or "halo") includes fluorine, chlorine, bromine and iodine.

Alkyl, Alkylene, Alkenyl, Alkynyl, Cycloalkyl Etc.

The terms "alkyl", "alkylene", "alkenyl" or "alkynyl" are used herein to refer to both straight and branched chain acyclic forms. Cyclic analogues thereof are referred to as cycloalkyl, etc.

The term "alkyl" includes monovalent, straight or branched, saturated, acyclic hydrocarbyl groups. In embodiments, alkyl is C$_{1-10}$alkyl, in another embodiment C$_{1-6}$alkyl, in another embodiment C$_{1-4}$alkyl, such as methyl, ethyl, n-propyl, i-propyl or t-butyl groups.

The term "cycloalkyl" includes monovalent, saturated, cyclic hydrocarbyl groups. In one embodiment cycloalkyl is C$_{3-10}$cycloalkyl, in another embodiment C$_{3-6}$cycloalkyl such as cyclopentyl and cyclohexyl.

The term "alkoxy" means alkyl-O—.

The term "alkylamino" means alkyl-NH—.

The term "alkylthio" means alkyl-S(O)$_w$—, wherein t is defined below.

The term "haloalkyl" refers to an alkyl group wherein at least one H is replaced by a halo group. In embodiments, haloalkyl refers to substitution by from 1-3 halo groups, e.g. 1. Examples include trihalomethyl, trihaloethyl, e.g. trifluoromethyl, etc.

The term "alkenyl" includes monovalent, straight or branched, unsaturated, acyclic hydrocarbyl groups having at least one carbon-carbon double bond and, in one embodiment, no carbon-carbon triple bonds. In one embodiment alkenyl is C$_{2-10}$alkenyl, in another embodiment C$_{2-6}$alkenyl, in another embodiment C$_{2-4}$alkenyl.

The term "cycloalkenyl" includes monovalent, partially unsaturated, cyclic hydrocarbyl groups having at least one carbon-carbon double bond and, in one embodiment, no carbon-carbon triple bonds. In embodiments, cycloalkenyl is C$_{3-10}$cycloalkenyl, in another embodiment C$_{5-10}$cycloalkenyl, e.g. cyclohexenyl or benzocyclohexyl.

The term "alkynyl" includes monovalent, straight or branched, unsaturated, acyclic hydrocarbyl groups having at least one carbon-carbon triple bond and, in one embodiment, no carbon-carbon double bonds. In one embodiment, alkynyl is $C_{2-10}$alkynyl, in another embodiment $C_{2-6}$alkynyl, in another embodiment $C_{2-4}$alkynyl.

The term "alkylene" includes divalent, straight or branched, saturated, acyclic hydrocarbyl groups. In one embodiment alkylene is $C_{1-10}$alkylene, in another embodiment $C_{1-6}$alkylene, in another embodiment $C_{1-4}$alkylene, such as methylene, ethylene, n-propylene, i-propylene or t-butylene groups.

The term "alkenylene" includes divalent, straight or branched, unsaturated, acyclic hydrocarbyl groups having at least one carbon-carbon double bond and, in one embodiment, no carbon-carbon triple bonds. In one embodiment alkenylene is $C_{2-10}$alkenylene, in another embodiment $C_{2-6}$alkenylene, in another embodiment $C_{2-4}$alkenylene.

Heteroalkyl, Etc.

The term "heteroalkyl" includes alkyl groups in which up to three carbon atoms, in one embodiment up to two carbon atoms, in another embodiment one carbon atom, are each replaced independently by O, $S(O)_w$ or N, provided at least one of the alkyl carbon atoms remains. The heteroalkyl group may be C-linked or hetero-linked, i.e. it may be linked to the remainder of the molecule through a carbon atom or through O, $S(O)_w$ or N, wherein t is defined below.

The term "heterocycloalkyl" includes cycloalkyl groups in which up to three carbon atoms, in one embodiment up to two carbon atoms, in another embodiment one carbon atom, are each replaced independently by O, $S(O)_w$ or N, provided at least one of the cycloalkyl carbon atoms remains. Examples of heterocycloalkyl groups include oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl and 1,4-diazepanyl. The heterocycloalkyl group may be C-linked or N-linked, i.e. it may be linked to the remainder of the molecule through a carbon atom or through a nitrogen atom.

The term "heteroalkenyl" includes alkenyl groups in which up to three carbon atoms, in one embodiment up to two carbon atoms, in another embodiment one carbon atom, are each replaced independently by O, $S(O)_w$ or N, provided at least one of the alkenyl carbon atoms remains. The heteroalkenyl group may be C-linked or hetero-linked, i.e. it may be linked to the remainder of the molecule through a carbon atom or through O, $S(O)_w$ or N.

The term "heterocycloalkenyl" includes cycloalkenyl groups in which up to three carbon atoms, in one embodiment up to two carbon atoms, in another embodiment one carbon atom, are each replaced independently by O, $S(O)_w$ or N, provided at least one of the cycloalkenyl carbon atoms remains. Examples of heterocycloalkenyl groups include 3,4-dihydro-2H-pyranyl, 5-6-dihydro-2H-pyranyl, 2H-pyranyl, 1,2,3,4-tetrahydropyridinyl and 1,2,5,6-tetrahydropyridinyl. The heterocycloalkenyl group may be C-linked or N-linked, i.e. it may be linked to the remainder of the molecule through a carbon atom or through a nitrogen atom.

The term "heteroalkynyl" includes alkynyl groups in which up to three carbon atoms, in one embodiment up to two carbon atoms, in another embodiment one carbon atom, are each replaced independently by O, $S(O)_w$ or N, provided at least one of the alkynyl carbon atoms remains. The heteroalkynyl group may be C-linked or hetero-linked, i.e. it may be linked to the remainder of the molecule through a carbon atom or through O, $S(O)_w$ or N.

The term "heteroalkylene" includes alkylene groups in which up to three carbon atoms, in one embodiment up to two carbon atoms, in another embodiment one carbon atom, are each replaced independently by O, $S(O)_w$ or N, provided at least one of the alkylene carbon atoms remains.

The term "heteroalkenylene" includes alkenylene groups in which up to three carbon atoms, in one embodiment up to two carbon atoms, in another embodiment one carbon atom, are each replaced independently by O, $S(O)_w$ or N, provided at least one of the alkenylene carbon atoms remains.

Aryl

The term "aryl" includes monovalent, aromatic, cyclic hydrocarbyl groups, such as phenyl or naphthyl (e.g. 1-naphthyl or 2-naphthyl). In general, the aryl groups may be monocyclic or polycyclic fused ring aromatic groups. Preferred aryl groups are $C_6$-$C_{14}$aryl.

Other examples of aryl groups are monovalent derivatives of aceanthrylene, acenaphthylene, acephenanthrylene, anthracene, azulene, chrysene, coronene, fluoranthene, fluorene, as-indacene, s-indacene, indene, naphthalene, ovalene, perylene, phenalene, phenanthrene, picene, pleiadene, pyrene, pyranthrene and rubicene.

The term "arylalkyl" means alkyl substituted with an aryl group, e.g. benzyl.

Heteroaryl

The term "heteroaryl" includes aryl groups in which one or more carbon atoms are each replaced by heteroatoms independently selected from O, S, N and $NR^N$, where $R^N$ is defined below (and in one embodiment is H or alkyl (e.g. $C_{1-6}$alkyl)).

In general, the heteroaryl groups may be monocyclic or polycyclic (e.g. bicyclic) fused ring heteroaromatic groups. Typically, heteroaryl groups contain 5-14 ring members (preferably 5-10 members) wherein 1, 2, 3 or 4 ring members are independently selected from O, S, N and $NR^N$. In one embodiment, a heteroaryl group may be 5, 6, 9 or 10 membered, e.g. 5-membered monocyclic, 6-membered monocyclic, 9-membered fused-ring bicyclic or 10-membered fused-ring bicyclic.

Monocyclic heteroaromatic groups include heteroaromatic groups containing 5-6 ring members wherein 1, 2, 3 or 4 ring members are independently selected from O, S, N or $NR^N$.

In one embodiment, 5-membered monocyclic heteroaryl groups contain 1 ring member which is an —$NR^N$— group, an —O— atom or an —S— atom and, optionally, 1-3 ring members (e.g. 1 or 2 ring members) which are =N— atoms (where the remainder of the 5 ring members are carbon atoms).

Examples of 5-membered monocyclic heteroaryl groups are pyrrolyl, furanyl, thiophenyl, pyrazolyl, imidazolyl, isoxazolyl, oxazolyl, isothiazolyl, thiazolyl, 1,2,3 triazolyl, 1,2,4 triazolyl, 1,2,3 oxadiazolyl, 1,2,4 oxadiazolyl, 1,2,5 oxadiazolyl, 1,3,4 oxadiazolyl, 1,3,4 thiadiazolyl, pyridyl, pyrimidinyl, pyridazinyl, pyrazinyl, 1,3,5 triazinyl, 1,2,4 triazinyl, 1,2,3 triazinyl and tetrazolyl.

Examples of 6-membered monocyclic heteroaryl groups are pyridinyl, pyridazinyl, pyrimidinyl and pyrazinyl.

In one embodiment, 6-membered monocyclic heteroaryl groups contain 1 or 2 ring members which are =N— atoms (where the remainder of the 6 ring members are carbon atoms).

Bicyclic heteroaromatic groups include fused-ring heteroaromatic groups containing 9-14 ring members wherein 1, 2, 3, 4 or more ring members are independently selected from O, S, N or $NR^{11}$.

In one embodiment, 9-membered bicyclic heteroaryl groups contain 1 ring member which is an $-NR^N-$ group, an —O— atom or an —S— atom and, optionally, 1-3 ring members (e.g. 1 or 2 ring members) which are =N— atoms (where the remainder of the 9 ring members are carbon atoms).

Examples of 9-membered fused-ring bicyclic heteroaryl groups are benzofuranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c] pyridinyl, pyrazolo[3,4-c]pyridinyl, pyrazolo[3,4-b] pyridinyl, isoindolyl, indazolyl, purinyl, indolininyl, imidazo[1,2-a]pyridinyl, imidazo[1,5-a]pyridinyl, pyrazolo [1,2-a]pyridinyl, pyrrolo[1,2-b]pyridazinyl and imidazo[1,2-c]pyrimidinyl.

In one embodiment, 10-membered bicyclic heteroaryl groups contain 1-3 ring members which are =N— atoms (where the remainder of the 10 ring members are carbon atoms). Examples of 10-membered fused-ring bicyclic heteroaryl groups are quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b] pyrazinyl and pyrimido[4,5-d]pyrimidinyl.

The term "heteroarylalkyl" means alkyl substituted with a heteroaryl group.

General

Unless indicated explicitly otherwise, where combinations of groups are referred to herein as one moiety, e.g. arylalkyl, the last mentioned group contains the atom by which the moiety is attached to the rest of the molecule.

Where reference is made to a carbon atom of an alkyl group or other group being replaced by O, $S(O)_w$ or N, what is intended is that:

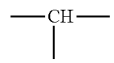

is replaced by

—CH= is replaced by —N=;
≡C—H is replaced by ≡N; or
—$CH_2$— is replaced by —O—, —$S(O)_w$— or —$NR^N$—.

By way of clarification, in relation to the above mentioned heteroatom containing groups (such as heteroalkyl etc.), where a numerical of carbon atoms is given, for instance $C_{3-6}$heteroalkyl, what is intended is a group based on $C_{3-6}$alkyl in which one of more of the 3-6 chain carbon atoms is replaced by O, $S(O)_w$ or N. Accordingly, a $C_{3-6}$heteroalkyl group, for example, will contain less than 3-6 chain carbon atoms.

Where mentioned above, $R^N$ is H, alkyl, cycloalkyl, aryl, heteroaryl, —C(O)-alkyl, —C(O)-aryl, —C(O)-heteroaryl, —$S(O)_w$-alkyl, —$S(O)_w$-aryl or —$S(O)_w$-heteroaryl. $R^N$ may, in particular, be H, alkyl (e.g. $C_{1-6}$alkyl) or cycloalkyl (e.g. $C_{3-6}$cycloalkyl).

Where mentioned above, w is independently 0, 1 or 2, for example 2. Typically, w is 0. Where a group has at least 2 positions which may be substituted, the group may be substituted by both ends of an alkylene or heteroalkylene chain to form a cyclic moiety.

Prodrugs Compounds of the Invention and Derivatives Thereof

As used herein, unless it is detailed otherwise, the terms "compounds of the invention" and "compound of formula (I) etc. include pharmaceutically acceptable derivatives thereof, polymorphs, isomers and isotopically labelled variants thereof. It is thus intended that this applies to all other formulae describing compounds according to the present invention as described herein and their pharmaceutically acceptable derivatives and embodiments thereof disclosed herein.

Pharmaceutically Acceptable Derivatives

The term "pharmaceutically acceptable derivative" herein includes any pharmaceutically acceptable salt, solvate (e.g. hydrate) of the prodrug compounds. In an embodiment, the pharmaceutically acceptable derivative is a pharmaceutically acceptable salt, solvate (e.g. hydrate) of the compound, i.e. compound of formula (I), typically a pharmaceutically acceptable salt thereof. In other words, the term "pharmaceutically acceptable salt" may thus optionally replace the term "pharmaceutically acceptable derivative" as recited anywhere herein.

Pharmaceutically Acceptable Salts

The term "pharmaceutically acceptable salt" includes a salt prepared from pharmaceutically acceptable non-toxic acids or bases including inorganic or organic acids and bases.

Compounds of the invention that contain basic, e.g. amino, groups are capable of forming pharmaceutically acceptable salts with acids. In one embodiment, pharmaceutically acceptable acid addition salts of the compounds of the invention include, but are not limited to, those of inorganic acids such as hydrohalic acids (e.g. hydrochloric, hydrobromic and hydroiodic acid), sulfuric acid, nitric acid and phosphoric acids. In one embodiment, pharmaceutically acceptable acid addition salts of the compounds of the invention include, but are not limited to, those of organic acids such as aliphatic, aromatic, carboxylic and sulfonic classes of organic acids, examples of which include: aliphatic monocarboxylic acids such as formic acid, acetic acid, propionic acid or butyric acid; aliphatic hydroxy acids such as lactic acid, citric acid, tartaric acid or malic acid; dicarboxylic acids such as maleic acid or succinic acid; aromatic carboxylic acids such as benzoic acid, p-chlorobenzoic acid, phenylacetic acid, diphenylacetic acid or triphenylacetic acid; aromatic hydroxyl acids such as o-hydroxybenzoic acid, p-hydroxybenzoic acid, 1-hydroxynaphthalene-2-carboxylic acid or 3-hydroxynaphthalene-2-carboxylic acid; and sulfonic acids such as methanesulfonic acid, ethanesulfonic acid or benzenesulfonic acid. Other pharmaceutically acceptable acid addition salts of the compounds of the invention include, but are not limited to, those of glycolic acid, glucuronic acid, furoic acid, glutamic acid, anthranilic acid, salicylic acid, mandelic acid, embonic (pamoic) acid, pantothenic acid, stearic acid, sulfanilic acid, algenic acid and galacturonic acid. Wherein the compound of the invention comprises a plurality of basic groups, multiple centres may be protonated to provide multiple salts, e.g. di- or tri-salts of compounds of the invention. For example, a hydrohalic acid salt of a compound of the invention as described herein may be a monohydrohalide, dihydrohalide or trihydrohalide, etc. In one embodiment, the salts include, but are not limited to those resulting from addition of any of the acids disclosed above. In one embodiment of the compound of the invention, two basic groups form acid addition salts. In a further embodiment, the two addition salt counterions are the same species, e.g. dihydrochloride, dihydrosulphide etc. Typically, the pharmaceutically acceptable salt is may be a hydrochloride salt, such as a dihydrochloride salt.

Compounds of the invention which contain acidic, e.g. carboxyl and/or —$SO_3H$ groups are capable of forming pharmaceutically acceptable salts with bases. In embodiments, pharmaceutically acceptable basic salts of the compounds of the invention include, but are not limited to, metal salts such as alkali metal or alkaline earth metal salts (e.g. sodium, potassium, magnesium or calcium salts) and zinc or aluminium salts. In one embodiment, pharmaceutically acceptable basic salts of the compounds of the invention include, but are not limited to, salts formed with ammonia or pharmaceutically acceptable organic amines or heterocyclic bases such as ethanolamines (e.g. diethanolamine), benzylamines, N-methyl-glucamine, amino acids (e.g. lysine) or pyridine.

Hemisalts of acids and bases may also be formed, e.g. hemisulphate salts.

Pharmaceutically acceptable salts of compounds of the invention may be prepared by methods well-known in the art. Thus, in typical embodiments of the aspects and embodiments of the invention, the pharmaceutically acceptable derivative thereof is a base addition salt, such as a metal salt (e.g. a sodium salt), or a salt formed using ammonia, a pharmaceutically acceptable organic amine or a heterocyclic base.

For a review of pharmaceutically acceptable salts, see Stahl and Wermuth, Handbook of Pharmaceutical Salts: Properties, Selection and Use (Wiley-VCH, Weinheim, Germany, 2002).

Amorphous & Crystalline Forms

The compounds of the invention may exist in solid states from amorphous through to crystalline forms. All such solid forms are included within the invention, including solvated (e.g. hydrated) and non-solvated forms, as described below.

Solvates & Hydrates

The compounds of the invention may exist in both unsolvated and solvated solid forms. The term "solvate" includes molecular complexes comprising a compound of the invention and one or more pharmaceutically acceptable solvent molecules such as water or $C_{1-6}$ alcohols, e.g. ethanol. The term "hydrate" means a "solvate" where the solvent is water.

Isomeric Forms

Compounds of the invention may exist in one or more geometrical, optical, enantiomeric, diastereomeric and tautomeric forms, including, but not limited to, cis- and trans-forms, E- and Z-forms, R-, S- and meso-forms, keto- and enol-forms. All such isomeric forms are included within the invention. The isomeric forms may be in isomerically pure or enriched form, as well as in mixtures of isomers (e.g. racemic or diastereomeric mixtures).

Accordingly, the invention provides, for use in the methods and treatments described herein:
stereoisomeric mixtures of compounds of the invention;
a diastereomerically enriched or diastereomerically pure isomer of a compound of the invention; or
an enantiomerically enriched or enantiomerically pure isomer of a compound of the invention.

Where appropriate, isomers can be separated from their mixtures by the application or adaptation of known methods (e.g. chromatographic techniques—such as chiral chromatography—, resolution techniques and recrystallization techniques). Where appropriate, isomers can be prepared by the application or adaptation of known methods (e.g. asymmetric synthesis).

Isotopic Labelling

The invention includes pharmaceutically acceptable isotopically-labelled compounds of the invention wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of the invention, for example those incorporating a radioactive isotope, are useful in drug and/or substrate tissue distribution studies. The radioactive isotopes $^{3}H$ and $^{14}C$ are particularly useful for this purpose in view of their ease of incorporation and ready means of detection.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds of the invention can generally be prepared by conventional techniques known to those skilled in the art or by processes analogous to those described herein using an appropriate isotopically-labelled reagent in place of the non-labelled reagent previously employed.

Typically, where the present disclosure refers to a pharmaceutically acceptable derivative of a compound, e.g. a compound of the invention, the derivative may suitably be a pharmaceutically acceptable salt.

Treatment of Diseases and Conditions

The present invention provides a solid prodrug composition, dispersion, an injectable formulation, or a pharmaceutical or veterinary composition as defined herein, for use as a medicament. Said medicament may be used as a monotherapy or it may be combined with any one or more other drugs, such that a combination therapy of prodrug compounds and/or compositions of the present invention with said one or more other drugs is provided. Such "other drugs" include, but are not limited to abacavir, didanosine, emtricitabine, lamivudine, stavudine, tenofovir disoproxil fumarate, zidovudine, efavirenz, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, cobicistat or any combination thereof. In addition, "other drugs" may also include combinations such as, but not limited to, epzicom (abacavir and lamivudine), triumeq (abacavir, dolutegravir, and lamivudine), trizivir (abacavir, lamivudine, and zidovudine), evotaz (atazanavir and cobicistat), prezcobix (darunavir and cobicistat), atripla (efavirenz, emtricitabine, and tenofovir disoproxil fumarate), genvoya (elvitegravir, cobicistat, emtricitabine, and tenofovir alafenamide fumarate), stribild (elvitegravir, cobicistat, emtricitabine, and tenofovir disoproxil fumarate), odefsey (emtricitabine, rilpivirine, and tenofovir alafenamide), complera (emtricitabine, rilpivirine, and tenofovir disoproxil fumarate), descovy (emtricitabine and tenofovir alafenamide), truvada (emtricitabine and tenofovir disoproxil fumarate), combivir (lamivudine and zidovudine) and kaletra (lopinavir and ritonavir).

In principle, the solid prodrug composition, dispersion, injectable formulation, or pharmaceutical or veterinary composition defined herein can be used for the treatment and/or propylaxis of an HIV infection. Treatment and/or propylaxis of an infection such as an HIV infection is contemplated. Moreover, prodrugs or solid prodrug compositions of the present invention may be used for the treatment and/or prevention of HIV via either pre-exposure prophylaxis (PrEP) and/or post-exposure prophylaxis (PEP) applications.

The solid prodrug composition, dispersion, injectable formulation, or pharmaceutical or veterinary composition defined herein can be used for the treatment and/or propylaxis of cancer and/or hepatitis B is also contemplated.

The present invention further provides a solid prodrug composition, dispersion, injectable formulation, or pharmaceutical or veterinary composition as defined herein for use in the treatment and/or prevention of HIV, cancer and/or hepatitis B.

The present invention further provides a use of a solid prodrug composition, dispersion, an injectable formulation, or pharmaceutical or veterinary composition as defined herein in the manufacture of a medicament for use in the treatment and/or prevention of HIV, cancer and/or hepatitis B.

The present invention further provides a method of treating and/or preventing HIV and cancer, the method comprising administering a therapeutically effective amount of a solid prodrug composition, a dispersion, an injectable formulation, or a pharmaceutical or veterinary composition as defined herein, to a patient suffering from or at risk of suffering from HIV, cancer and/or hepatitis B.

In any or all of the above-described uses, the administered form of nanoparticles of the prodrug preferably provides a controlled release bolus formulation of the prodrug compound, which, when administered to a patient, releases the prodrug into the bloodstream of the patient over a period of at least about two weeks from the date of administration. Further preferably the period of release is at least about three weeks, yet further preferably at least about one month, more preferably at least about three months, and most preferably at least about six months, from the date of administration of the injection.

Therapeutic Definitions

As used herein, "treatment" includes curative and prophylactic treatment. As used herein, a "patient" means an animal, preferably a mammal, preferably a human, in need of treatment.

The amount of the compound of the invention administered should be a therapeutically effective amount where the compound or derivative is used for the treatment of a disease or condition and a prophylactically effective amount where the compound or derivative is used for the prevention of a disease or condition.

The term "therapeutically effective amount" used herein refers to the amount of compound needed to treat or ameliorate a targeted disease or condition. The term "prophylactically effective amount" used herein refers to the amount of compound needed to prevent a targeted disease or condition. The exact dosage will generally be dependent on the patient's status at the time of administration. Factors that may be taken into consideration when determining dosage include the severity of the disease state in the patient, the general health of the patient, the age, weight, gender, diet, time, frequency and route of administration, drug combinations, reaction sensitivities and the patient's tolerance or response to therapy. The precise amount can be determined by routine experimentation, but may ultimately lie with the judgement of the clinician. An effective dose may in instances be from 0.01 mg/kg/day (mass of drug compared to mass of patient) to 1000 mg/kg/day, e.g. 1 mg/kg/day to 100 mg/kg/day. Compositions may be administered individually to a patient or may be administered in combination with other agents, drugs or hormones.

Routes of Administration

The solid prodrug compositions, dispersions, and pharmaceutical or veterinary compositions of the invention, whether as a monotherapy or as a combination therapy (as discussed below), may be administered to a patient by any convenient route of administration. More than one route of administration may be used in combination within a defined treatment and/or prophylactic regime, especially for a combination therapy, in which one component of the combination may be administered via one route, whilst another component of the combination may be administered via a different route. All such combinations are hereby contemplated.

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, infraarterial, intracardiac, intrathecal, intraspinal, intracapsular, subcapsular, intraorbital, intraperitoneal, intratracheal, subcuticular, intraarticular, subarachnoid, and intrasternal; or by implant of a depot or reservoir, for example, subcutaneously or intramuscularly.

Most preferably, the route of administration is by parenteral implant of a depot or reservoir formulation.

Preferably, the injectable formulation of the present invention is a depot formulation administered so as to provide a controlled release in the patient over at least a period of weeks, preferably months.

Combination Therapy

The prodrugs or prodrug composition of the invention may be administered alone or may be administered in combination with another compound of the invention or another therapeutic agent (i.e. a different agent to the compound of the invention). Preferably, the compound of the invention and the other therapeutic agent are administered in a therapeutically effective amount.

The prodrug or prodrug composition of the present invention may be administered either simultaneously with, or before or after, the other therapeutic agent. The compound of the present invention may be administered separately, by the same or different route of administration, or together in the same pharmaceutical composition.

In one embodiment, the invention provides a product comprising a prodrug or prodrug composition of the invention and another therapeutic agent as a combined preparation for simultaneous, separate or sequential use in therapy, i.e. in treating HIV and or cancer. In one embodiment, the therapy is the treatment of HIV and/or cancer. Products provided as a combined preparation include a composition comprising the prodrug and/or prodrug composition of the present invention and the other therapeutic agent together in the same pharmaceutical composition, or the prodrug and/or prodrug composition and the other therapeutic agent in separate form, e.g. in the form of a kit.

In an embodiment, the invention thus provides a pharmaceutical composition comprising a prodrug and/or prodrug composition and another therapeutic agent. Optionally, the pharmaceutical composition may comprise a pharmaceutically acceptable excipient, as described above in "Administration and formulation".

In one embodiment, the invention provides a kit comprising two or more separate pharmaceutical compositions, at least one of which contains a prodrug and/or prodrug composition of the present invention. In one embodiment, the kit comprises means for separately retaining said compositions, such as a container, divided bottle or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention may typically comprise directions for administration.

In the combination therapies of the invention, the prodrug and/or prodrug composition of the present invention and the other therapeutic agent may be manufactured and/or formulated by the same or different manufacturers. Moreover, the prodrug and/or prodrug composition of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

It will be understood that the prodrug compounds, compositions and combinations discussed above may be used in the treatments and uses herein described with respect to treating HIV, cancer and/or hepatitis B.

BRIEF DESCRIPTION OF FIGURES

FIG. 1 includes table 1 presenting the IUPAC name, structure, yield, NMR data and/or melting point data for compounds of the present invention.

FIG. 4 illustrates half-life measurements in pooled mixed gender human plasma and female skeletal muscle S9 for compounds of the present invention.

FIG. 5 illustrates kinetic analysis data for the conversion of prodrug compound 17 to 13.

FIG. 6 illustrates kinetic analysis data for the conversion of prodrug compound 5 to 13.

FIG. 7 illustrates half-life measurements in human liver S9 for prodrug compounds 20 and 21.

FIG. 12 illustrates hydrolysis data measured in mouse or human plasma/liver of compounds of the present invention.

FIG. 13 illustrates half-life measurements for prodrug compound 23.

METHODS AND EXAMPLES

Figure 2:
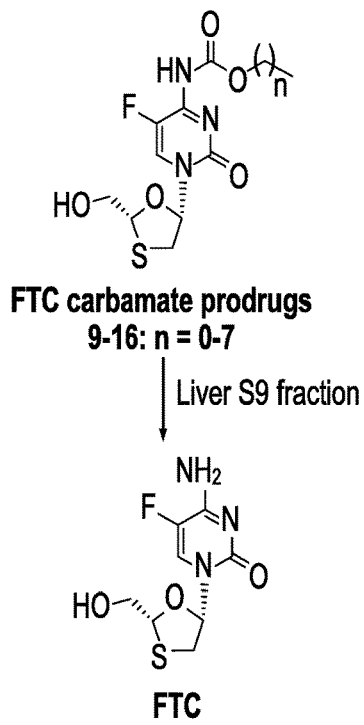
FIG. 2 illustrates hydrolysis measurement measured in pooled mixed gender human liver S9 for compounds of the present invention.

The following examples are intended to illustrate the invention and are not to be construed as being limitations thereon. If not mentioned otherwise, all evaporations are performed under reduced pressure, between 50 mmHg and 100 mmHg. The structure of final products, intermediates and starting materials is confirmed by standard analytical methods, e.g., microanalysis, melting point (m.p.) and spectroscopic characteristics, e.g. MS, IR and NMR. Abbreviations used are those conventional in the art.

Preparation of Prodrug Compounds

In general, compounds 1-26 (as illustrated in FIG. 1) may be prepared according to the general methods described below. The skilled person will appreciate that further compounds of the invention are accessible via these general methods by modification of the starting materials and/or substituent groups included in these general methods.

General Method for Synthesis of 5'-Alkoxycarbonyl Emtricitabine Carbamates (Prodrug Compounds 1-8)

In a flame-dried 25 mL round-bottom flask, cooled under argon, emtricitabine (1.0 eq., 0.5 M) was suspended in DCM. Pyridine (3.0 eq., 1.5 M) was then added to the flask and the resulting mixture was cooled to 0° C. in an ice-water bath. The reaction was initiated by the dropwise addition of the appropriate alkyl chloroformate (2.1 eq., 1.05 M). The reaction mixture was left to stir at 0° C. before then being warmed to room temperature. The reaction was monitored by TLC and considered to be complete after 3 hours. The reaction mixture was condensed under reduced pressure and the resulting crude residue was purified via silica flash chromatography (0-10% MeOH in DCM gradient) to provide prodrug compounds 1-8 as a clear oil.

General Procedure for Synthesis of Emtricitabine Carbamates (Prodrug Compounds 9-16)

In a 20 mL vial, compounds 1-8 (1.0 eq., 0.5 M) were suspended in THF. Lithium hydroxide (10 eq., 5 M) was then added followed by the dropwise addition of water (~20 drops) to increase the solubility of the reaction mixture. The reaction mixture was then left at room temperature to stir. The reaction was monitored by TLC and was considered to be complete after 18 hours. The reaction mixture was condensed under reduced pressure and the resulting crude residue was purified via silica flash chromatography (0-10% MeOH in DCM gradient) to provide compounds 9-16 as a white solid.

General Procedure for Synthesis of 5'-Acyloxy Emtricitabine Carbamates (Prodrug Compounds 17-22)

In a flame-dried 10 mL round-bottom flask, cooled under argon, pyridine (2.0 eq., 0.4 M) was dissolved in DCM. The flask was then cooled to 0° C. in an ice-water bath. The appropriate acyl chloride (1.2 eq., 0.24 M) was then added dropwise to the flask. The reaction was left to stir at 0° C. under argon for 15 minutes. Compounds 13-16 (1.0 eq., 0.2 M) were added to the acyl chloride-pyridine mixture. The reaction mixture was then left to stir at 0° C. for 3 hours. The reaction was monitored by TLC and once complete, the mixture was condensed under reduced pressure. The resulting crude residue was purified via silica flash chromatography (0-100% EtOAc in Hexanes gradient) to provide compounds 17-22 as a clear oil.

Synthesis of (Z)—N'-(5-fluoro-1-((2R,5S)-2-(hydroxymethyl)-1,3-oxathiolan-5-yl)-2-oxo-1,2-dihydropyrimidin-4-yl)-N,N-dimethylformimidamide (prodrug compound 23)

Emtricitabine (255 mg, 1.03 mmol, 1.0 equiv.) was suspended in 4.1 mL of methanol at room temperature. To the suspension was added N,N-dimethylformamide dimethyl acetal (0.68 ml, 5.15 mmol, 5.0 equiv.) in one portion at room temperature to provide a colourless solution after approximately 5 minutes. After approximately a further 1-2 hours a precipitate formed. The reaction mixture was stirred for 21 hours at room temperature in total. The reaction mixture was then condensed and volatiles removed under reduced pressure using a rotary evaporator. The resulting residue was then dried under high vacuum for 3 hours to afford compound 23 (311 mg; white solid; quantitative yield). Compound 23 was used without further purification.

Synthesis of 2-(4-((1-((2R,5S)-2-(((tert-butyldimethylsilyl)oxy)methyl)-1,3-oxathiolan-5-yl)-5-fluoro-2-oxo-1,2-dihydropyrimidin-4-yl)amino)-2-methyl-4-oxobutan-2-yl)-3,5-dimethylphenyl acetate (Prodrug Compound 24)

To a solution of 3-(2-acetoxy-4,6-dimethylphenyl)-3-methylbutanoic acid (205 mg, 0.77 mmol) in anhydrous DMF (1.55 ml) was added HATU (294 mg, 0.77 mmol) in one portion at room temperature followed by the addition of diisopropylethylamine (0.30 ml, 1.74 mmol). After stirring at room temperature for 5 minutes, 4-amino-1-((2R,5S)-2-(((tert-butyldimethylsilyl)oxy)methyl)-1,3-oxathiolan-5-yl)-5-fluoropyrimidin-2(1H)-one (279 mg, 0.77 mmol) was added in one portion. The reaction mixture was stirred for 3 days at room temperature. The reaction mixture was then diluted with water and saturated aqueous $Na_2CO_3$ and extracted with EtOAc (3×15 mL). The organic layers were combined, washed with brine, dried with anhydrous $MgSO_4$ and concentrated in vacuo. The resulting residue was then purified by flash chromatography (0-100% EtOAc in Hexanes gradient) to provide compound 24 (305 mg; 65% yield) as clear colourless glass.

Synthesis of 2-(4-((5-fluoro-1-((2R,5S)-2-(hydroxymethyl)-1,3-oxathiolan-5-yl)-2-oxo-1,2-dihydropyrimidin-4-yl)amino)-2-methyl-4-oxobutan-2-yl)-3,5-dimethylphenyl acetate (Prodrug Compound 25)

To a solution of 2-(4-((1-((2R,5S)-2-(((tert-butyldimethylsilyl)oxy)methyl)-1,3-oxathiolan-5-yl)-5-fluoro-2-oxo-1,2-dihydropyrimidin-4-yl)amino)-2-methyl-4-oxobutan-2-yl)-3,5-dimethylphenyl acetate (compound 24) (218 mg, 0.36 mmol) in THF (1.8 mL) was added trimethylamine trihydrofluoride (292 µL, 1.79 mmol) in one portion at room temperature. After approximately 5 hours at room temperature, TLC indicated that the starting material was fully consumed. To the reaction mixture was then added water (15 mL) and EtOAc (15 mL). The resulting mixture was then extracted with EtOAc (3×10 mL), the organic layers were combined, washed with brine, dried with anhydrous $MgSO_4$ and concentrated in vacuo. The resulting residue was then purified by reverse phase (C18) flash chromatography (0 to 100% MeCN in H2O gradient) to provide compound 25 (153 mg; 86% yield) as a clear colourless glass.

Synthesis of (2S)-isopropyl (((((R)-1-(6-(3-(2-acetoxy-4,6-dimethylphenyl)-3-methylbutanamido)-9H-purin-9-yl)propan-2-yl)oxy)methyl)(phenoxy)phosphoryl)-L-alaninate (Prodrug Compound 26)

To a solution of 3-(2-acetoxy-4,6-dimethylphenyl)-3-methylbutanoic acid (284 mg, 1.08 mmol) in 0.4 M NMM/DMF (2.5 mL) was added HATU (391 mg, 1.03 mmol) in one portion at room temperature. After stirring at room temperature for 5 minutes, to the mixture was added (2S)-isopropyl2-((((((R)-1-(6-amino-9H-purin-9-yl)propan-2-yl)oxy)methyl)(phenoxy)phosphoryl)amino)propanoate (466 mg, 0.99 mmol) in one portion and the resulting reaction mixture was stirred for 3 days at room temperature. Saturated aqueous $Na_2CO_3$ was then added the mixture then extracted with EtOAc (3×15 mL). The organic layers were combined, washed with brine, dried with anhydrous $MgSO_4$ and concentrated in vacuo. The resulting residue was then purified by flash chromatography (0 to 10% MeOH/$CHCl_3$ gradient) to provide compound 26 (87 mg; 12% yield) as clear colourless glass.

Kinetic Analysis

General Procedure for Preliminary Hydrolysis Measurements of Emtricitabine Carbamate Prodrug Compounds 10-16 and Capecitabine To evaluate the hydrolysis rates of compounds 10-16, HPLC coupled with UV detection was used. This was performed using the following method (0% to 100% acetonitrile in $Et_3NHOAc$ (50 mM, pH 8) gradient) over 10 minutes at a flow rate of 3 mL $min^{-1}$, held at 100% acetonitrile for 3 minutes, ramped down to 5% acetonitrile over 0.2 minutes and then held for 2.8 minutes. Pooled mixed gender human liver S9 (20.0 mg/mL, Xenotech) was pre-incubated at 37° C. for 5 minutes. Compounds 10-16 (1 mM) were then added and the mixture incubated at 37° C.

Aliquots were taken at each time point and quenched in an equal volume of ice-cold methanol. The quenched aliquots were then centrifuged at 14000 rpm for 5 minutes. The supernatant was diluted 10 fold into Tris buffer (30 mM, pH 7.4) and injected onto the HPLC for analysis.

Hydrolysis measurements of compounds 10-16 at 1 mM in 20.0 mg/mL pooled mixed gender human liver S9 are shown in FIG. 2 and demonstrate that emtricitabine carbamates with longer alkyl chains are more rapidly cleaved.

General Procedure for Kinetic Analysis of Emtricitabine Carbamate Prodrug Compounds 9-16 and Capecitabine Via UV Reaction mixtures containing Tris buffer (30 mM, pH 7.4) and mixed pooled gender liver S9 (10.0 mg/mL) were pre-incubated at 37° C. for 5 min. Reactions are initiated by the addition of emtricitabine prodrug compounds 9-16 and capecitabine (concentrations vary from 200 uM to 10 mM for capecitabine and compounds 13-16, concentrations up to 20 mM for compound 12 and concentrations up to 60 mM for compounds 9-11). After incubation at 37° C., aliquots were taken at each time point and quenched in two volumes of ice-cold methanol. The quenched aliquots were then centrifuged at 14000 rpm for 5 minutes. The supernatant was diluted into Tris buffer (30 mM, pH 7.4) to yield concentrations appropriate for analysis and read spectrophotometrically monitoring a decrease in substrate at 305 nm.

Figure 3:
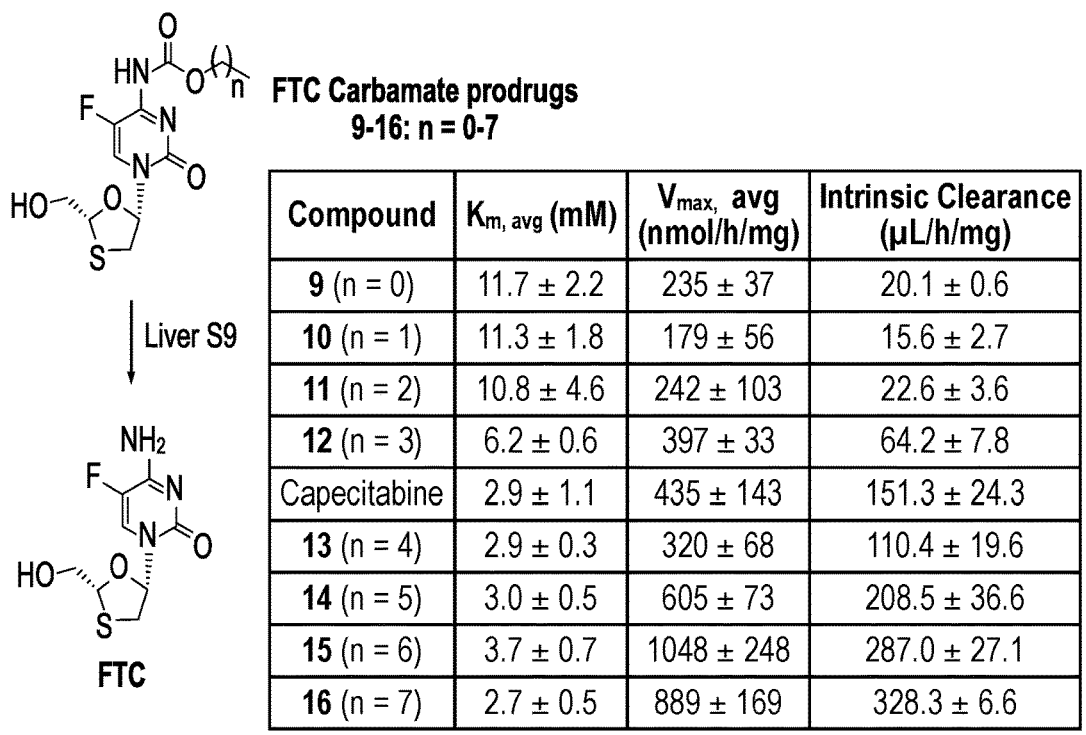
FIG. 3 illustrates kinetic analysis data measuring hydrolysis in pooled mixed gender human liver S9 for compounds of the present invention.

The results of the kinetic analysis of emtricitabine carbamate compounds 9-16 is illustrated in FIG. 3. FIG. 3 demonstrates that carbamate to emtricitabine hydrolysis, measured in pooled mixed gender human liver S9, results in emtricitabine carbamates with longer alkyl chains having a higher intrinsic clearance. This is indicative of a more rapid rate of hydrolysis.

General Procedure for Half-Life Measurements of Prodrug Compounds 9-16 in Plasma and Muscle S9

To evaluate the hydrolysis rates of emtricitabine compounds 9-16, HPLC coupled with UV detection was used with the following method (0% to 100% acetonitrile in Et$_3$NHOAc (50 mM, pH 8) gradient) over 10 minutes at a flow rate of 3 mL min$^{-1}$, held at 100% acetonitrile for 3 minutes, ramped down to 5% acetonitrile over 0.2 minutes and then held for 2.8 minutes. Male human plasma (Bioreclamation) or female human skeletal muscle S9 (7.96 mg/mL, Bioreclamation) was pre-incubated at 37° C. for 5 minutes. Compounds 9-16 (1 mM) were added and the reaction was incubated at 37° C. Aliquots were taken at each time point and quenched in two volumes of ice-cold methanol. The quenched aliquots were then centrifuged at 14000 rpm for 5 minutes. The supernatant was diluted 10 fold into Tris buffer (30 mM, pH 7.4) and injected onto the HPLC for analysis.

The results of the half-life analysis in pooled mixed gender human plasma and female skeletal muscle S9 are illustrated in FIG. 4. FIG. 4 indicates long hydrolysis half-lives for compounds 9-16 regardless of alkyl chain length.

General Procedure for Kinetic Analysis of 5'-Acetoxy Emtricitabine Carbamates Prodrug Compound Hydrolysis A reaction mixture containing Tris buffer (30 mM, pH 7.4) and mixed pooled gender liver S9 (1 mg/mL, 3.0 mg/mL, or 4.0 mg/mL) are pre-incubated at 37° C. for 5 minutes. To the reaction mixtures is added compound 17 which initiates the hydrolysis reaction (concentrations of compound 17 ranging from 200 μM to 10 mM). After incubation at 37° C., aliquots were taken at each time point and quenched in two volumes of ice-cold methanol. The quenched aliquots were then centrifuged at 14000 rpm for 3 minutes. The supernatant was diluted into Tris buffer (30 mM, pH 7.4) to yield samples with concentrations appropriate for analysis. The samples were analyzed by HPLC with UV detection using the following method (0% to 100% acetonitrile in Et$_3$NHOAc (50 mM, pH 8) gradient) over 10 minutes at a flow rate of 3 mL min$^{-1}$, held at 100% acetonitrile for 3 minutes, ramped down to 5% acetonitrile over 0.2 minutes and then held for 2.8 minutes.

Kinetic analysis data for the conversion of compound 17 to compound 13 via 5'-acetoxy hydrolysis is illustrated in FIG. 5. The hydrolysis was performed under conditions in which the pentyl carbamate group of compound 17 is stable in 1.0 mg/mL pooled mixed gender human liver S9. It was observed that the intrinsic clearance for the 5'-acetoxy hydrolysis is greater than that for the carbamate group hydrolysis.

Kinetic analysis data for the conversion of compound 5 to compound 13 via 5'-pentoxycarbonyl hydrolysis is illustrated in FIG. 6 (concentrations of compound 5 ranging from 200 μM to 10 mM). The hydrolysis was performed under conditions in which the pentyl carbamate group is stable in 3.0 mg/mL pooled mixed gender human liver S9. It was observed that the intrinsic clearance for 5'-pentoxycarbonyl hydrolysis is greater than that for carbamate group hydrolysis but reduced when compared to the intrinsic clearance of the 5'-acetoxy hydrolysis. Kinetic analysis data for the conversion of compound 17 to compound 13 via 5'-acetoxy hydrolysis and the conversion of compound 5 to compound 13 via 5'-pentoxycarbonyl hydrolysis is presented in Table 1 below.

TABLE 1

| Compound | $K_M$ (mM) | $V_{max}$ (nmol/h/mg) | Intrinsic Clearance (μL/h/mg) |
|---|---|---|---|
| 17 | 1.31 | 4877 | 3723 |
| 5 | 0.6 | 948 | 1580 |

Kinetic analysis data for compounds 20 and 21 in human liver S9 was generated in accordance with the general procedure described above. The data, as illustrated in FIG. 7 shows comparable half-lives for compounds 20 and 21.

Procedure for Log P Determinations of Emtricitabine Carbamate Prodrug Compounds

Figures 8, 9:
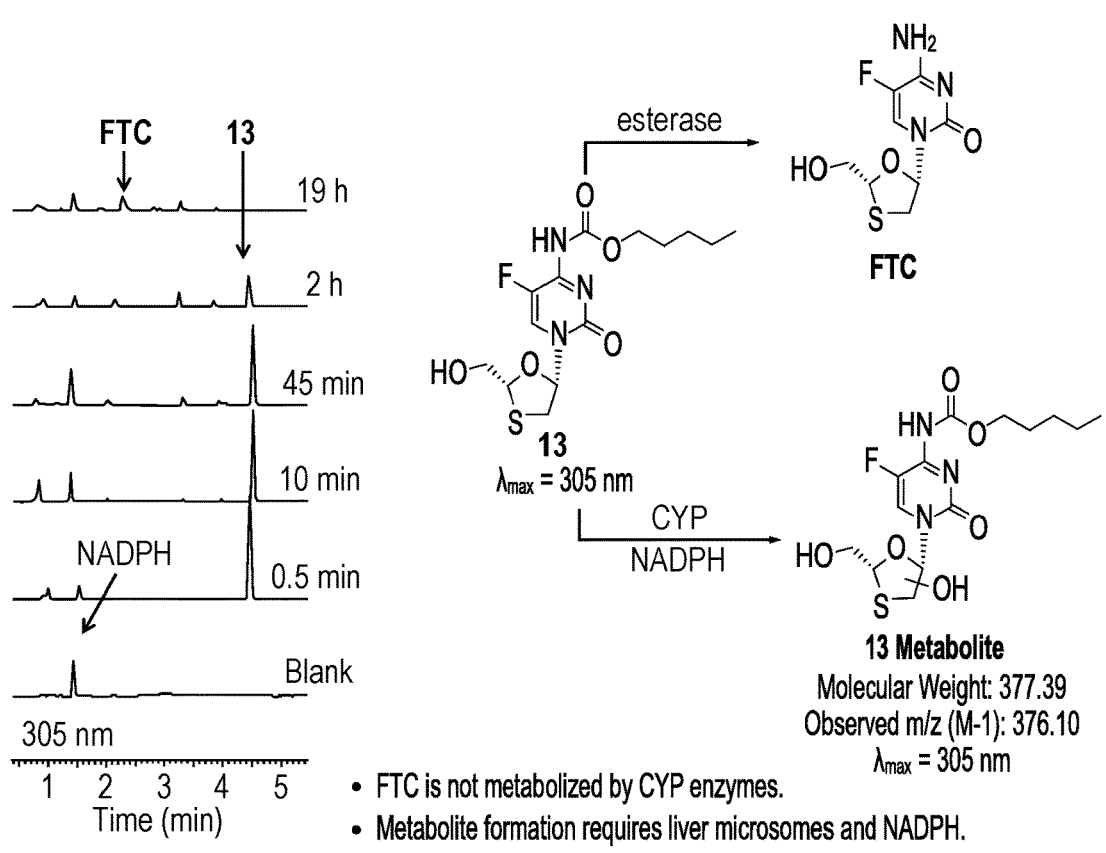
FIG. 8 presents log P measurements for compounds of the present invention.
FIG. 9 illustrates HPLC data for the analysis of cytochrome P450 activity on prodrug compounds of the present invention.

Carbamate compounds were dissolved in 1-octanol and mixed vigorously with an equal volume of deionized water. The mixture was then allowed to separate and each layer collected, diluted and measured by HPLC coupled with a UV detection system (5% to 100% acetonitrile/Et$_3$NHOAc (50 mM, pH 8) gradient) over 10 minutes at a flow rate of 3 mL min$^{-1}$. The log P values for emtricitabine carbamate prodrug compounds, taken as an average of triplicate measurements, are illustrated in FIG. 8. It was observed that there is an increase in log P as the carbamate group alkyl chain length increases.

Procedure for Analysis of Cytochrome P450 Activity on Emtricitabine and Prodrug Compound 13

Reaction mixtures containing phosphate buffer (100 mM, pH 7.4), mixed pooled gender human liver microsomes (2.0 mg/mL), NADP+ (1 mM), glucose-6-phosphate (5 mM), and glucose-6-phosphate dehydrogenase (1.5 Unit/mL) were pre-incubated at 37° C. for 5 minutes. The reactions were then initiated via the addition of emtricitabine or compound 13 (1 mM). After incubation at 37° C., aliquots were taken at each time point and quenched in two volumes of ice-cold methanol. The quenched aliquots were then centrifuged at 14000 rpm for 4 minutes. The supernatant was then diluted into phosphate buffer (100 mM, pH 7.4) to yield samples with concentrations suitable for analysis. The samples were analyzed by HPLC with UV detection using the following method (0% to 100% acetonitrile in Et$_3$NHOAc (50 mM, pH 8) gradient) over 10 minutes at a flow rate of 3 mL min$^{-1}$, held at 100% acetonitrile for 3 minutes, ramped down to 5% acetonitrile over 0.2 minutes and then held for 2.8 minutes.

it was observed that emtricitabine was not metabolized by CYP enzymes in 2.0 mg/mL pooled mixed gender human liver microsomes. However, compound 13 was metabolized only in the presence of NADPH. Further LC-MS analysis suggests that the compound 13 metabolite was hydroxylated, as shown in FIG. 9.

Procedure for Analysis of UGT Activity on Emtricitabine and Prodrug Compound 13

Reaction mixtures containing phosphate buffer (100 mM, pH 7.4), mixed pooled gender human liver S9 (2.0 mg/mL), MgCl$_2$ (10 mM), UDPGA (8 mM), and D-saccharic acid-1, 4-lactone (2 mM) were pre-incubated at 37° C. for 5 minutes. The reactions were then initiated by the addition of emtricitabine or compound 13 (1 mM). After incubation at 37° C., aliquots were taken at each time point and quenched in two volumes of ice-cold methanol. The quenched aliquots were then centrifuged at 14000 rpm for 4 minutes. The supernatant was then diluted into phosphate buffer (100 mM, pH 7.4) to yield samples with concentrations suitable for analysis. The samples were analyzed by HPLC with UV detection using the following method (0% to 100% acetonitrile in Et$_3$NHOAc (50 mM, pH 8) gradient) over 10 minutes at a flow rate of 3 mL min$^{-1}$, held at 100% acetonitrile for 3 minutes, ramped down to 5% acetonitrile over 0.2 minutes and then held for 2.8 minutes.

Figure 10:
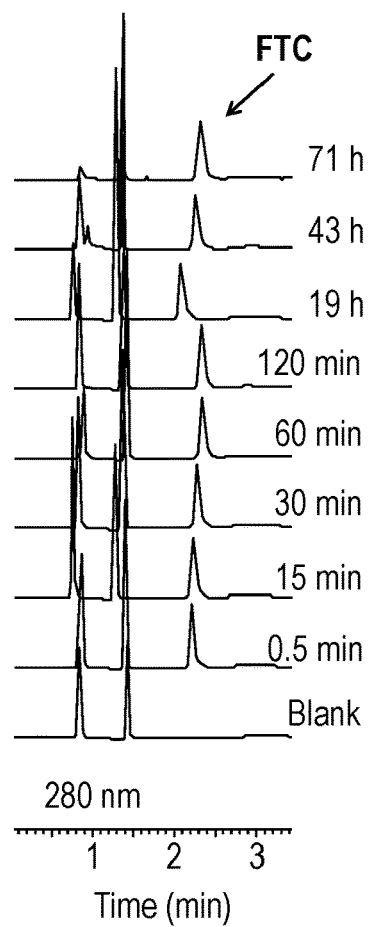
FIGS. 10 and 11 illustrate HPLC data for the UGT enzyme metabolism of prodrugs of the present invention.
Figure 11:
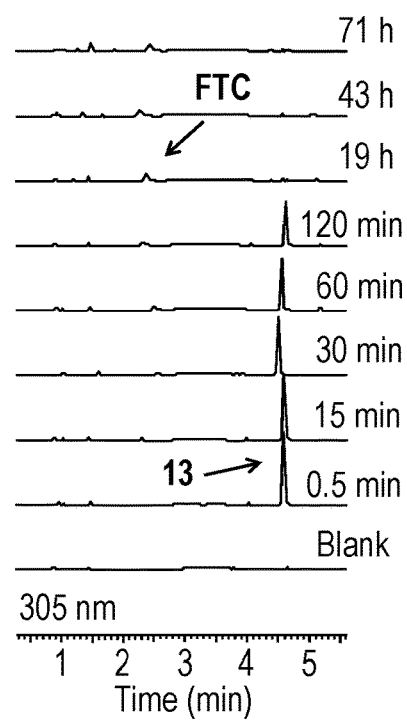
Figure 14:
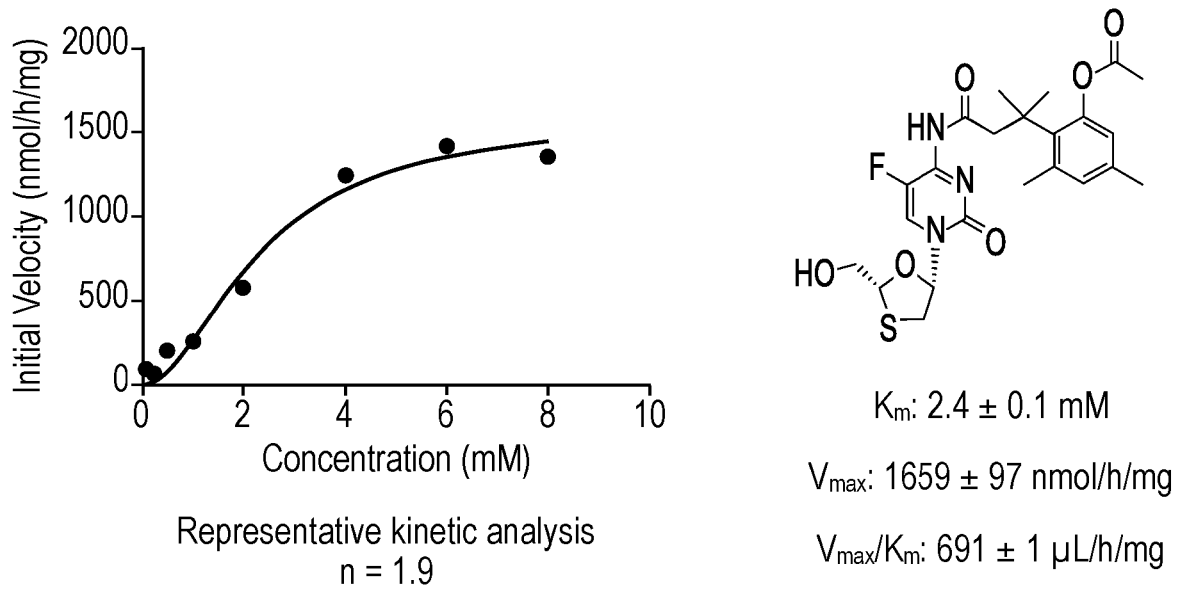
FIG. 14 illustrates half-life measurements for prodrug compound 25.

HPLC analysis, as shown in FIG. 10, illustrates that emtricitabine is not metabolized by UGT enzymes. HPLC analysis, as shown in FIG. 11, illustrates that compound 13 is also not metabolized by UGT enzymes. The only reaction observed was the conversion of compound 13 into emtricitabine via carbamate hydrolysis.

General Procedure for Analysis of Prodrug Hydrolysis in Mouse, Rat, and Human Liver S9 or Plasma Reaction mixtures containing either mouse liver S9 (20.8 mg/mL), mouse plasma, rat liver S9 (1 mg/mL) and phosphate buffer (100 mM, pH 7.4), rat plasma, human liver S9 (1.0 mg/mL) and phosphate buffer (100 mM, pH 7.4) or human plasma were pre-incubated at 37° C. for 5 minutes. Reactions were then initiated by addition of compounds 4, 8 or 16 (1 mM in mouse, 0.5 mM in rat and human). After incubation at 37° C., aliquots are taken at each time point and quenched in two volumes of ice-cold methanol. The quenched aliquots were then centrifuged at 14000 rpm for 5 minutes. The supernatant was then diluted into phosphate buffer (30 mM, pH 7.4) to yield samples with concentrations suitable for analysis. The samples were analyzed by HPLC with UV detection and the resulting hydrolysis data can be seen in FIG. 12.

It was observed that the hydrolysis rate for emtricitabine carbamate compound 16 (1 mM) is comparable in mouse and human liver S9. However, the hydrolysis rate of compound 16 in mouse plasma is dramatically enhanced relative to human plasma (illustrated in FIG. 3).

Table 2 shows half-life data for compounds 4 and 8 (0.5 mM) for both rat plasma/liver and human plasma/liver. In all cases, the half-lives for compound 4 are shorter than that of compound 8. The data indicates that the octyl carbonate hydrolysis of compound 8 occurs less readily than butyl carbamate hydrolysis of compound 4. In all cases, the half-life indicates the depletion of starting material compounds. In rat compartments, the evidence suggests that the carbamate group of the prodrug compounds is cleaved before the carbonate groups. In human compartments, only carbonate cleavage is observed.

TABLE 2

| Compound | Rat Plasma t$_{1/2}$ (min) | Rat Liver t$_{1/2}$ (min) | Human Plasma t$_{1/2}$ (min) | Human Liver t$_{1/2}$ (min) |
|---|---|---|---|---|
| 4 | 5.8 | 4.6 | 59.2 | 10.3 |
| 8 | 16.7 | 33.3 | 578 | 151 |

General Procedure for Half-Life Measurements of Emtricitabine Amidine Prodrug Compound 23

To evaluate the hydrolysis rates of emtricitabine amidine prodrugs, HPLC coupled with UV detection was used with the following method (0% to 100% acetonitrile in Et$_3$NHOAc (50 mM, pH 8) gradient) over 10 minutes at a flow rate of 3 mL min$^{-1}$, held at 100% acetonitrile for 3 minutes, ramped down to 5% acetonitrile over 0.2 minutes and then held for 2.8 minutes. Normal human serum (Bioreclamation) or phosphate buffer (100 mM, pH 7.4) was pre-incubated at 37° C. for 5 minutes. Emtricitabine amidine compound 23 (1 mM) was then added and the reaction mixture was incubated at 37° C. Aliquots were taken at each time point and quenched in three volumes of ice-cold methanol. The quenched aliquots were then centrifuged at 14000 rpm for 7 minutes. The supernatant was injected onto a HPLC system for analysis, the resulting data can be seen illustrated in FIG. 13. Half-life data for emtricitabine amidine compound 23 can be seen as presented in Table 3 below.

TABLE 3

| Conditions | Half-Life (h) |
|---|---|
| Phosphate Buffer (100 mM, pH 7.4) | 95 |
| Human Serum | 5.8 |

General Procedure for Kinetic Analysis of Emtricitabine Trimethyl Lock Prodrugs Via UV A reaction mixture containing Tris buffer (30 mM, pH 7.4) and mixed pooled gender liver S9 (10.0 mg/mL) was pre-incubated at 37° C. for 5 minutes. The reaction was then initiated by the addition of emtricitabine trimethyl lock compound 25 (concentration of compound 25 ranging from 100 μM to 8 mM). After incubation at 37° C., aliquots were taken at each time point and quenched in two volumes of ice-cold methanol. The quenched aliquots were then centrifuged at 14000 rpm for 5 minutes. The supernatant was diluted into Tris buffer (30 mM, pH 7.4) to yield samples having concentrations appropriate for analysis and read spectrophotometrically monitoring a decrease in substrate at 312 nm. The kinetic analysis data has been summarized in Table 4 below.

TABLE 4

| Compound | K$_M$ (mM) | V$_{max}$ (nmol/h/mg) | Intrinsic Clearance (μL/h/mg) |
|---|---|---|---|
| 25 | 2.4 | 1659 | 691 |

General Procedure for Half-Life Measurements of Emtricitabine Trimethyl Lock Prodrugs To evaluate the hydrolysis rates of emtricitabine trimethyl lock prodrugs, HPLC coupled with UV detection was used with the following method (0% to 100% acetonitrile in $Et_3NHOAc$ (50 mM, pH 8) gradient) over 10 minutes at a flow rate of 3 mL min$^{-1}$, held at 100% acetonitrile for 3 minutes, ramped down to 5% acetonitrile over 0.2 minutes and then held for 2.8 minutes. Human plasma (Bioreclamation) or human skeletal muscle S9 (7.96 mg/mL, Bioreclamation) was pre-incubated at 37° C. for 5 minutes. Emtricitabine trimethyl lock compound 25 (1 mM) was added and the reaction was incubated at 37° C. Aliquots were taken at each time point and quenched in three volumes of ice-cold methanol. The quenched aliquots were then centrifuged at 14000 rpm for 5 minutes. The supernatant was diluted in Tris buffer (100 mM, pH 7.4) and injected onto the HPLC for analysis. Half-life data for emtricitabine trimethyl lock compound 25 is presented in Table 5 below.

TABLE 5

| Conditions | Half-Life (h) |
| --- | --- |
| Human plasma | 0.4 |
| Human muscle S9 (7.96 mg/mL) | 1 |

Figure 15:
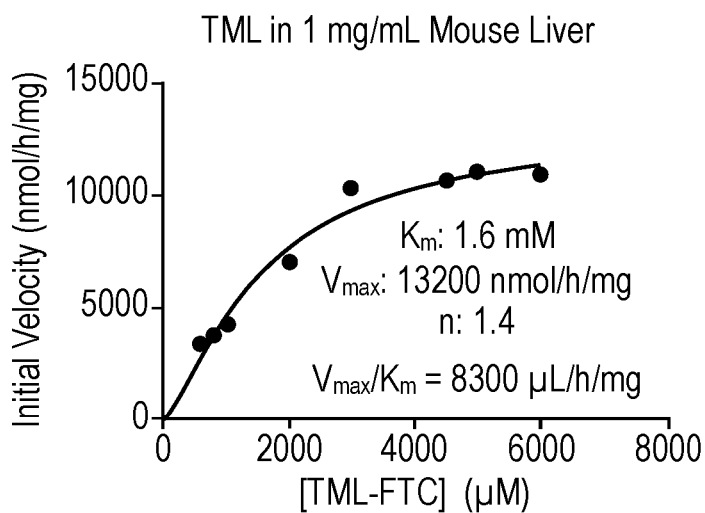
FIG. 15 illustrates kinetic analysis data for prodrug compound 25.

General Procedure for Kinetic Analysis of Emtricitabine Trimethyl Lock Prodrugs in Mouse Liver S9 Via UV A reaction mixture containing Tris buffer (30 mM, pH 7.4) and mixed pooled gender mouse liver S9 (1.0 mg/mL) were pre-incubated at 37° C. for 5 minutes. The reaction is then initiated by the addition of emtricitabine trimethyl lock compound 25 (concentration of compound 25 ranging from 600 μM to 6 mM). After incubation at 37° C., aliquots were taken at each time point and quenched in two volumes of ice-cold methanol. The quenched aliquots were then centrifuged at 14000 rpm for 5 minutes. The supernatant was diluted into Tris buffer (30 mM, pH 7.4) to yield concentrations appropriate for analysis and read spectrophotometrically monitoring a decrease in substrate at 312 nm. The kinetic analysis data in mouse liver S9, as illustrated in FIG. 15, has been summarized in Table 6 below.

TABLE 6

| Compound | $K_M$ (mM) | $V_{max}$ (nmol/h/mg) | Intrinsic Clearance (μL/h/mg) |
| --- | --- | --- | --- |
| 25 | 1.6 | 13200 | 8300 |

General Procedure for Half-Life Measurements of Tenofovir Alafenamide Trimethyl Lock Prodrug in Human Plasma To evaluate the hydrolysis rates of tenofovir alafenamide compound 26, HPLC coupled with UV detection was used with the following method (0% to 100% acetonitrile in $Et_3NHOAc$ (50 mM, pH 8) gradient) over 10 minutes at a flow rate of 3 mL min$^{-1}$, held at 100% acetonitrile for 3 minutes, ramped down to 5% acetonitrile over 0.2 minutes and then held for 2.8 minutes. Human plasma (Bioreclamation) was pre-incubated at 37° C. for 5 minutes. Compound 26 (1 mM) was added and the reaction was incubated at 37° C. Aliquots were taken at each time point and quenched in two volumes of ice-cold methanol. The quenched aliquots were then centrifuged at 14000 rpm for 5 minutes. The supernatant was diluted in Tris buffer (100 mM, pH 7.4) and injected onto the HPLC for analysis.

Figure 16:
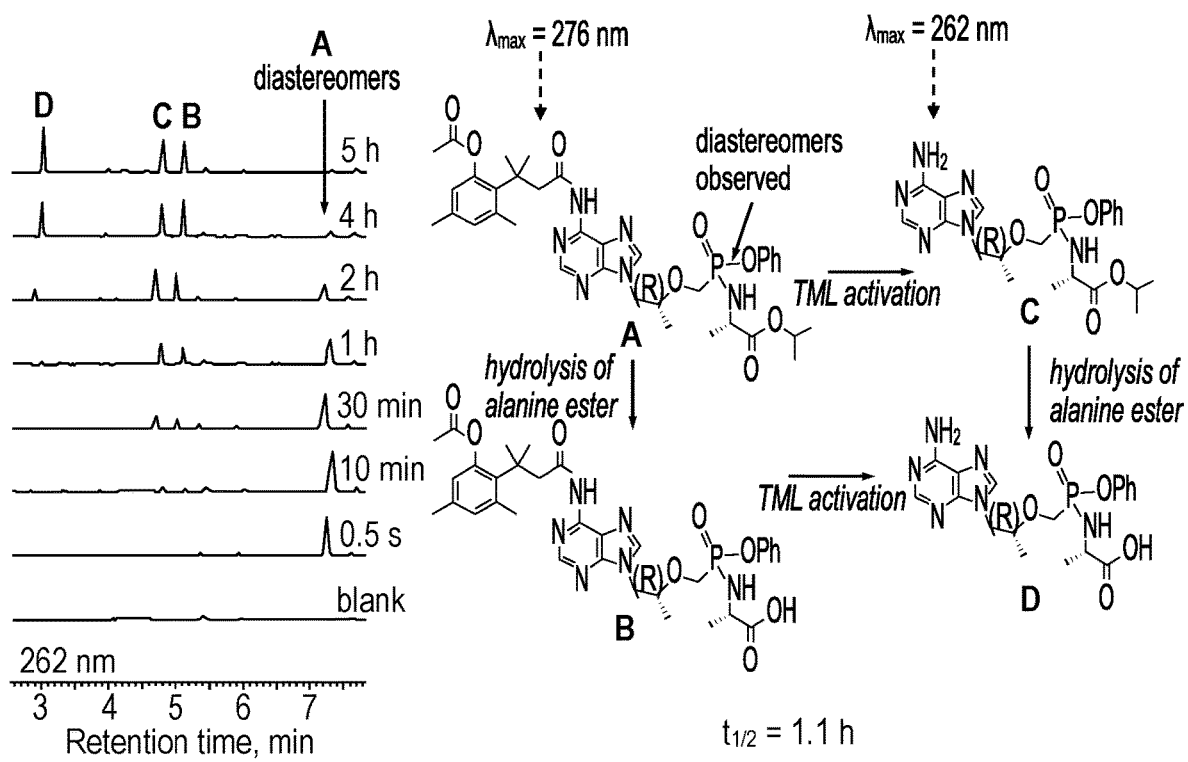
FIG. 16 illustrates the hydrolysis analysis of prodrug compound 26 in human plasma.

The HPLC analysis data of tenofovir alafenamide compound 26 in human plasma, illustrated in FIG. 16, shows that hydrolysis (through two potential pathways) occurs with a half-life of 1.1 h.

Single-Round Infectivity Assays

Procedure for Single-Round Infectivity Assays

Based on the kinetic analysis data provided above, compounds 16 and 25 were demonstrated to be most efficiently hydrolysed and, therefore, were selected for single-round infectivity assays.

Peripheral blood mononuclear cells were isolated from healthy blood donors using Hypaque-Ficoll gradient centrifugation. CD4+ T cells were selected by magnetic beads (Miltenyi) and activated using anti-CD3 and anti-CD28 antibodies. Activated cells were seeded onto a 96-well plate at a concentration of 1×10$^5$ cells/well in RPMI1640 supplemented with 10% FBS, cytokine-rich supernatant, and 50% heat-inactivated human serum. Test compounds were added at this step and maintained throughout the culture. Cells were incubated at 37° C. for 21 hours. Pseudotype (GFP-tagged) HIV was then added to the culture via spinoculation and incubated for 3 days. Cells were then washed and stained with Zombie Red viability stain. Infectivity was quantified using flow cytometry.

The IC$_{50}$ for emtricitabine obtained closely matches literature reported values. In addition, viability staining indicates that there is little to no toxicity of FTC on CD4+ T cells. The IC$_{50}$ obtained for compounds 25 and 16 shows comparable potency to the parent emtricitabine. Viability staining also indicates little to no toxicity of 16 and 25 on CD4+ T cells. The IC$_{50}$ data for these compounds is presented in Table 7 below.

TABLE 7

| Compound | IC$_{50}$ (nM) ± SD |
| --- | --- |
| Emtricitabine | 14.4 ± 4.1 |
| 16 | 39.4 ± 17.6 |
| 25 | 28.6 ± 1.2 |

Stability Assessment of Single-Round Infectivity Assay Well Media

Well media used in the single-round infectivity assays as described above, comprised of RPMI1640 medium supplemented with 10% FBS, cytokine-rich supernatant, 50% heat-inactivated human serum and HEPES buffer (12 mM). The emtricitabine test compounds were incubated in well media at 37° C. At various time points, aliquots were quenched in two volumes of ice-cold methanol. Quenched mixtures were then centrifuged at 14000 rpm for 5 minutes. The supernatant was diluted 10-fold into Tris buffer (30 mM, pH 7.4) and then analyzed via HPLC coupled with UV detection.

Stability studies indicate that both compounds 16 and 25 were hydrolyzed to the parent emtricitabine in a time-frame matching the time of pre-incubation in single-round infectivity assays. This is likely due to the presence of heat-inactivated serum still containing active esterases. The antiviral potency of 16 and 25 is thus due to parent emtricitabine revealed following carbamate hydrolysis. Well media half-life data is provided in Table 8 below.

TABLE 8

| Compound | Well Media Half-Life (h) |
| --- | --- |
| 16 | 18 |
| 25 | 0.83 |

Preparation of Prodrug Nanoparticles

In general, prodrug nanoparticles of the present invention may be prepared according to the general methods described below. The skilled person will appreciate that further nanoparticles of the invention are accessible via these general methods by modification of the prodrug compound, carrier materials, reagents or the reaction conditions included in these general methods.

Initial Screening Approach for Prodrug Nanoparticles

Prodrug nanoparticles based on prodrug compounds 1-26, prepared and investigated as described above, were synthesised. The prodrug nanoparticles were formed using carrier materials (i.e. polymers and surfactants) selected based on their ability to stabilise nanoparticles in aqueous environments as well as their safety profiles according to the FDA's GRAS list. These selected carrier materials are listed in Table 9 below.

TABLE 9

| Polymer | Surfactant |
| --- | --- |
| Pluronics ® F-68 | Vitamin-E-polyethylene glycol-succinate (TPGS) |
| Pluronics ® F-127 | Sodium deoxycholate (NDC) |
| Polyvinyl alcohol (PVA) | Polyoxyethylene (20) sorbitan monolaurate (Tween ™ 20) |
| Kollicoat ™ | Polyoxyethylene (20) sorbitan monooleate (Tween ™ 80) |
| Polyethylene Glycol (PEG) k1 (Mw 1,000) | Dioctyl sulfosuccinate sodium salt (AOT) |
| Hydroxylpropyl methyl cellulose (HPMC), Polyvinylpyrrolidone k30 ('PVP k30') | Polyethylene glycol (15)-hydroxystearate (Solutol ™ HS) |

Screening of Prodrug Particles Containing Prodrug Compounds at 10 wt % Loadings

For each prodrug compound 1-23 and 25 42 binary combinations (i.e. each polymer was systematically combined with each surfactant) of the polymers and surfactants (listed in Table 9) were used to prepare prodrug nanoparticles, loaded with 10 wt % prodrug compound, for the initial screening. The prodrug compound loadings for each of the prodrug nanoparticles were 10 wt % compared to carrier materials. The 10 wt % loaded prodrug nanoparticles were prepared according to the procedure below.

Procedure for the Preparation of 10 wt % Loaded Prodrug Nanoparticles

Stock solutions of carrier materials were dissolved in water at a concentration of 22.5 mg/ml and left to roll overnight to ensure full dissolution. Prodrugs were dissolved in chloroform at a concentration of 10 mg/mL, using a magnetic stirrer bar and magnetic stirrer plate, at room temperature to ensure full dissolution. The resultant prodrug solutions were not left rolling overnight, due to the likely hydrolysis of the modified carbamate and/or carbonate groups.

Into a 4 mL glass vial was added 266.6 µL of polymer solution, along with 133.4 µL of surfactant solution. To this total of 400 µL aqueous phase, 100 µL of prodrug solution in chloroform was added giving a ratio of 1:4 of organic phase to aqueous phase. This two phase mixture was then sonicated (Covaris S2x ultrasonicator, with a duty cycle of 20%, an intensity of 250, cycles per burst of 500 in frequency sweeping mode). This provided homogenous emulsions. Following sonication, the emulsions were immediately frozen in liquid nitrogen prior to being freeze dried for 48 hours using a Benchtop K freeze dryer (Virtis) at a setting of −100° C. and a pressure of <20 pBar.

At the end of the 48 hours freeze drying process, the samples were sealed and placed in a humidity controlled desiccator prior to analysis. The dried prodrug nanoparticle monoliths had a composition of 1 mg prodrug, 3 mg surfactant, and 6 mg polymer.

Physical characterisation of the prodrug nanoparticles (after dispersion in water) such as hydrodynamic diameter and polydispersity index (PDI) were analysed using Dynamic Light Scattering (DLS) (also referred to as Photon Correlation Spectroscopy (PCS)). Dynamic light scattering measurements were carried out at 25° C. on a Malvern Instruments Ltd. Zetasizer Nano S spectrometer using the following parameters.

Particle Type: Nanoparticles (Refractive Index 1.330, Absorption 0.010)

Dispersant: Water (Viscosity 0.8872 cP, Refractive Index 1.330)

Temperature: 25° C.

Cell Type: Polystyrene disposable cuvette

Measurement Angle: 172° Back Scatter

Number of Measurements: 3

Number of runs per measurement: Automatic

Prodrug nanoparticles "hits" were then identified based on their ability to disperse in water (at a concentration of 1 mg/mL), having Z-average hydrodynamic diameters of less than 1000 nm and PDI values of less than 0.5.

Figure 17:
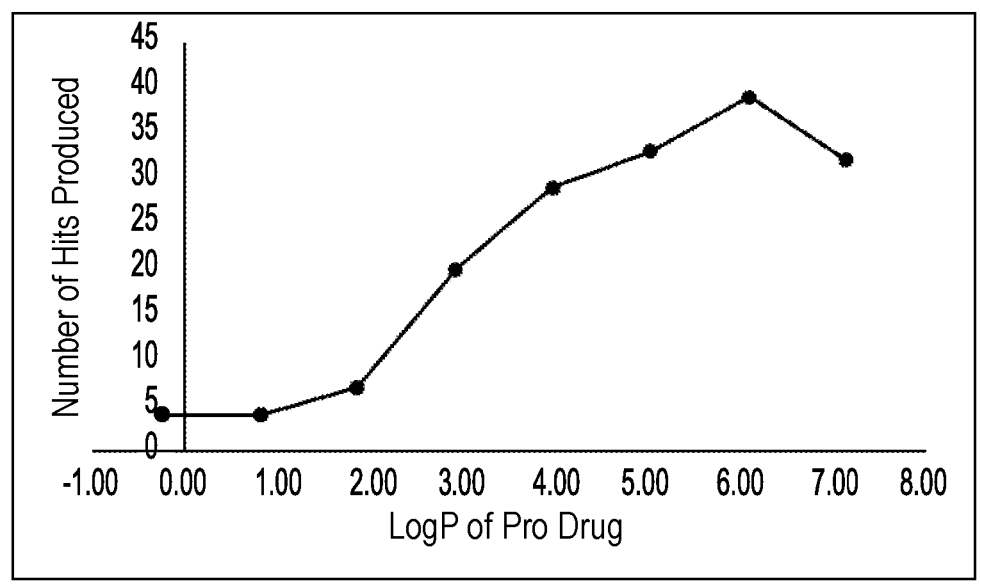
FIG. 17 illustrates the relationship between log P value and the number of hits identified during initial screening studies as described herein.

It was observed that there is a clear correlation between the log P of the prodrug compound and the number of prodrug nanoparticle "hits" formed from the 42 binary combinations of polymer/surfactant. With being bound theory, the data suggest that as the carbon chain length of the carbonate/carbamate groups of the prodrug compounds 1-8 increases, the number of prodrug nanoparticle "hits" formed from the 42 binary combinations of polymer/surfactant increases. FIG. 17 illustrates the relationship between the log P of carbonate/carbamate prodrug compounds 1-8 and the number of prodrug nanoparticle "hits" formed from the 42 binary combinations of polymer/surfactant.

Prodrug nanoparticles based on the carbonate/carbamate prodrug compounds 1-8 having narrow size distributions with PDI values of less than (<0.2) were selected. It was also observed that at a minimum carbon chain length of 4 of the carbonate/carbamate groups there was an enhanced quality of prodrug nanoparticles produced. This is illustrated in FIG. 18 where prodrug nanoparticles of the present invention show narrow hydrodynamic size distributions.

Figures 18, 19:
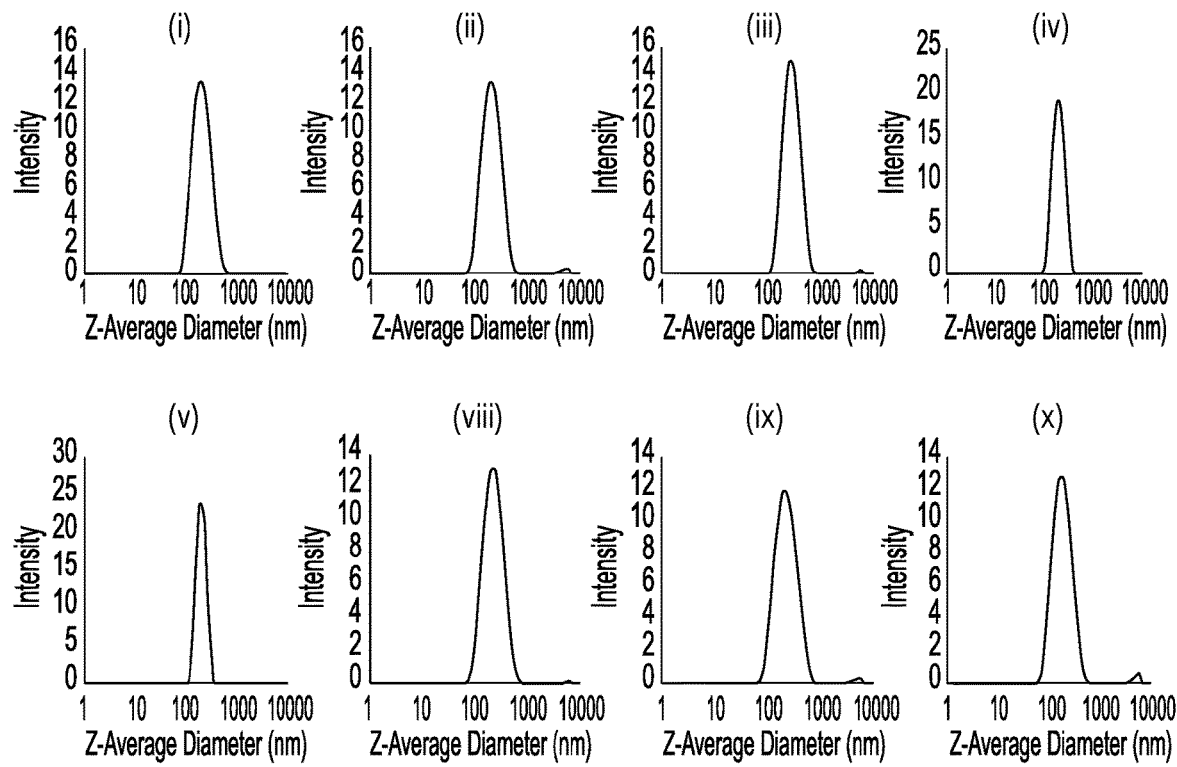
FIG. 18 illustrates hydrodynamic diameter distribution traces for prodrug nanoparticles hits of the present invention.
FIG. 19 illustrates a meta-analysis of hits identified across the full range of the prodrug compositions of the present invention.

FIG. 19 illustrates a heat map showing the frequency of "hits" produced for each binary combination of polymer/surfactant. The data indicates that the prodrug nanoparticles containing sodium deoxycholate (NDC) surfactant had an increased likelihood of being identified as a "hit" as compared to the other surfactants.

TABLE 10

| Prodrug nanoparticle composition | Prodrug compound | Polymer | Surfactant | Z-average hydrodynamic diameter (nm) | PDI |
|---|---|---|---|---|---|
| (i) | 4 | PVA | Tween™ 80 | 177 | 0.176 |
| (ii) | 4 | Pluronics ® F-68 | NDC | 180 | 0.181 |
| (iii) | 4 | Kollicoat™ | NDC | 250 | 0.173 |
| (iv) | 5 | PVP k30 | Tween™ 20 | 184 | 0.073 |
| (v) | 5 | PVA | Tween™ 20 | 193 | 0.010 |
| (vi) | 5 | Pluronics ® F-127 | Tween™ 20 | 184 | 0.060 |
| (vii) | 6 | Kollicoat™ | AOT | 226 | 0.013 |
| (viii) | 7 | PVP k30 | Tween™ 20 | 197 | 0.143 |
| (ix) | 7 | Kollicoat™ | Tween™ 80 | 192 | 0.197 |
| (x) | 8 | Pluronics ® F-68 | NDC | 165 | 0.187 |

Table 10 shows a selection of prodrug nanoparticles (i)-(x) identified from the initial screening approach at 10 wt % prodrug compound loading which demonstrate narrow size distributions.

Screening of Prodrug Particles Containing Prodrug Compounds at 50 wt % and 70 Wt % Loadings Similar screening approaches were performed for the prodrug nanoparticles having prodrug compound loadings of 50 wt % and 70 wt %. The prodrug nanoparticles were prepared according to the procedures described below.

Procedure for the Preparation of 50 wt % Loaded Prodrug Nanoparticles

Stock solutions of polymer were dissolved in water at a concentration of 13.3 mg/mL, with surfactants dissolved in water at a concentration of 10 mg/mL and left to roll overnight to ensure full dissolution. Prodrugs compounds were dissolved in chloroform at a concentration of 50 mg/mL, using a magnetic stirrer bar and magnetic stirrer plate, at room temperature, to ensure full dissolution. The resultant prodrug solutions were not left rolling overnight, due to the likely hydrolysis of the modified carbamate and/or carbonate groups.

In a 4 mL glass vial, 300 µL of polymer solution was added, along with 100 µL of surfactant solution. To this total of 400 µL aqueous phase, 100 µL of prodrug compound in solution of chloroform as added, giving a ratio of 1:4 organic to aqueous phase. The samples were then processed using sonication and freeze drying as for the 10 wt % samples described above. The dried nanoparticle monoliths had a composition of 5 mg drug, 1 mg surfactant, and 4 mg polymer.

The number of "hits" (as described above) for the prodrug nanoparticles containing prodrug compounds at 50 wt % was lower compared to the number of "hits" identified during the 10 wt % loading screen. Prodrug nanoparticles containing prodrug compound 1 at 50 wt % loading together with the NDC/PVP k30 and NDC/Kollicoat™ combinations produced "hits". Prodrug nanoparticles containing prodrug compound 4 at 50 wt % loading together with the following surfactant/polymer combinations produced "hits" (TPGS/Pluronics® F-127, TPGS/Kollicoat™, TPGS/PVA, Tween™ 20/PVA and Tween™ 80/PVA). Prodrug nanoparticles containing prodrug compound 8 at 50 wt % loading together with the following surfactant/polymer combinations produced "hits" (TPGS/Pluronics® F-68, TPGS/HMPC, TPGS/Pluronics® F-127, TPGS/Kollicoat™ TPGS/PVA, Tween™ 20/HMPC, Tween™ 20/PVA, Tween™ 80/HMPC, Tween™ 80/Kollicoat™, NDC/HMPC, NDC/Pluronics® F-127, NDC/Kollicoat™, NDC/PVA, AOT/HMPC, AOT/PVA, Solutol™ HS/Pluronics® F-68 and Solutol™ HS/HMPC).

Procedure for the Preparation of 70 wt % Loaded Prodrug Nanoparticles Stock solutions of polymer were dissolved in water at a concentration of 10 mg/mL, with surfactants dissolved in water at a concentration of 5 mg/mL and left to roll overnight to ensure full dissolution. Prodrugs compounds were dissolved in chloroform at a concentration of 70 mg/mL, using a magnetic stirrer bar and magnetic stirrer plate, at room temperature, to ensure full dissolution. The resultant prodrug solutions were not left rolling overnight, due to the likely hydrolysis of the modified carbamate and/or carbonate groups.

In a 4 mL glass vial, 200 µL of polymer solution was added, along with 200 µL of surfactant solution. To this total of 400 µL aqueous phase, 100 µL of pro drug in solution of chloroform was added, giving a ratio of 1:4 organic to aqueous phase. The samples were then processed using sonication and freeze drying as for 10 wt % samples described above. The dried nanoparticle monoliths had a composition of 7 mg drug, 1 mg surfactant, and 2 mg polymer The number of "hits" (as described above) for the prodrug nanoparticles containing prodrug compounds at 70 wt % was lower compared to the number of "hits" identified during the 50 wt % loading screen. Prodrug nanoparticles containing prodrug compound 4 at 70 wt % loading together with the Tween™ 20/PVA and AOT/HMPC surfactant/polymer combinations produced "hits". Prodrug nanoparticles containing prodrug compound 8 at 70 wt % loading together with TPGS/Pluronics® F-127 and NDC/Polyethylene glycol k1 surfactant/polymer combinations also produced "hits".

Summary of Initial Screening Results

Based on the physicochemical properties determined during the initial screening studies performed on the prodrug nanoparticles having prodrug compound loadings of 10 wt %, 50 wt % and 70 wt %, the most promising surfactant/polymer combinations were identified. These were prodrug nanoparticles containing prodrug compound 4 (at both 50 wt % and 70 wt % loadings) and Tween™ 20/PVA as well as prodrug nanoparticles containing prodrug compound 8 (at both 50 wt % and 70 wt % loadings) and TPGS/Pluronics® F-127.

Figure 20:
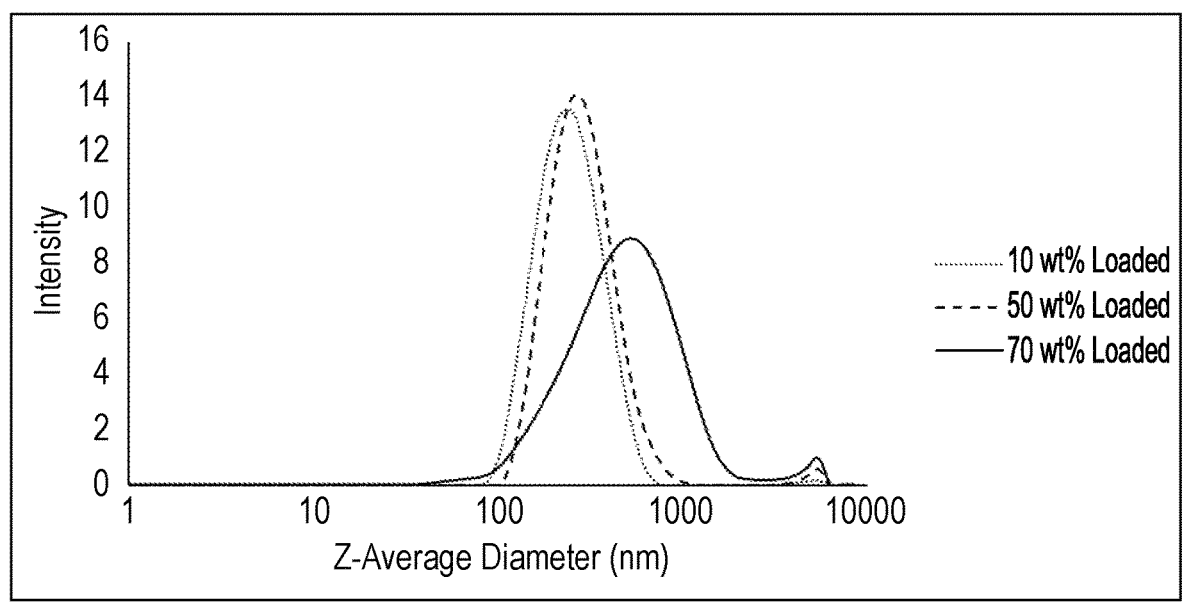
FIGS. 20 and 21 illustrate hydrodynamic diameter distribution traces for prodrug nanoparticles of the present invention at different wt % loadings.
Figure 21:
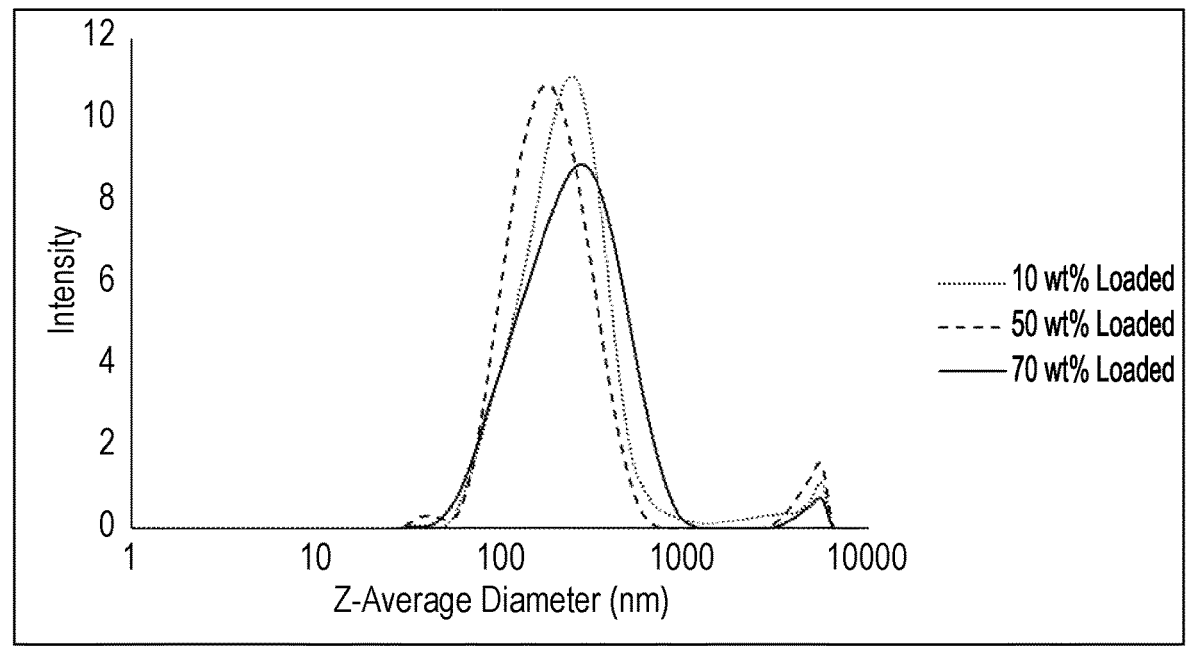

Table 11 shows that these prodrug nanoparticles (xi)-(xiv) possess narrow size distributions. FIG. 20 illustrates the hydrodynamic size distributions for prodrug nanoparticles containing prodrug compound 4 (10 wt %, 50 wt % and 70 wt %) and Tween™ 20/PVA. FIG. 21 illustrates the hydrodynamic size distributions for prodrug nanoparticles containing prodrug compound 8 (10 wt %, 50 wt % and 70 wt %) and TPGS/Pluronics® F-127.

TABLE 11

| Prodrug nanoparticle | Prodrug compound | Prodrug loading (wt %) | Polymer | Surfactant | Z-average hydrodynamic diameter (nm) | PDI |
|---|---|---|---|---|---|---|
| xi | 4 | 50 | PVA | Tween™ 20 | 291 | 0.240 |
| xii | 4 | 70 | PVA | Tween™ 20 | 412 | 0.437 |
| xiii | 8 | 50 | Pluronics ® F-127 | TPGS | 177 | 0.279 |

TABLE 11-continued

| Prodrug nano-particle | Prodrug compound | Prodrug loading (wt %) | Polymer | Surfactant | Z-average hydro-dynamic diameter (nm) | PDI |
|---|---|---|---|---|---|---|
| xiv | 8 | 70 | Pluronics® F-127 | TPGS | 240 | 0.415 |

In Vivo Pharmacokinetic Studies

In vivo pharmacokinetic studies were performed to determine the plasma concentrations of long-acting emtricitabine prodrug nanoparticles following intramuscular administration. The prodrug nanoparticles consist of novel emtricitabine prodrugs loaded into solid prodrug nanoparticles. The effects 12 solid prodrug nanoparticles compositions intramuscularly administered over a period of 7 days was investigated. Compositions containing a polymer/surfactant combination of Pluronics® F-127/TPGS and PVA/Tween™ 20 were selected based on their excellent performance during the initial screening studies described above. The compositions containing a polymer/surfactant combination of HMPC/NDC and HMPC/AOT were selected in order to further investigate the effect of the polymer/surfactant combination on the pharmacokinetic profile of the compositions. Table 12 provides details of the solid prodrug nanoparticles compositions selected for the study.

TABLE 12

| Prodrug nanoparticle | Prodrug compound | Prodrug loading (wt %) | Polymer | Surfactant |
|---|---|---|---|---|
| xiv | 8 | 70 | Pluronics® F-127 | TPGS |
| xii | 4 | 70 | PVA | Tween™ 20 |
| xv | 4 | 50 | Pluronics® F-127 | TPGS |
| xvi | 6 | 50 | Pluronics® F-127 | TPGS |
| xiii | 8 | 50 | Pluronics® F-127 | TPGS |
| xi | 4 | 50 | PVA | Tween™ 20 |
| xvii | 6 | 50 | PVA | Tween™ 20 |
| xviii | 8 | 50 | PVA | Tween™ 20 |
| xix | 6 | 50 | HMPC | NDC |
| xx | 8 | 50 | HMPC | NDC |
| xxi | 6 | 50 | HMPC | AOT |
| xxii | 8 | 50 | HMPC | AOT |

General Procedure for In Vivo Studies

Adult male Wistar rats (~300 g) were divided into 12 groups (1 rat per group). Groups were dosed with the prodrug nanoparticles (as shown in Table 12 above) (10 mg/Kg of emtricitabine, adjusted for mz of emtricitabine in each prodrug) via intramuscular injection in the musculus biceps femoris. Food and water was provided ad libitum throughout the procedure.

Following habituation (7 days) the rats received a single dose of the prodrug nanoparticles via intramuscular injection (0.1 mL as a suspension in distilled water) as outlined above. The rats were anesthetised during injection (isoflurane), EMLA was given topically and buprenorphine provided subcutaneously (0.3 mg/mL). Blood samples were then collected (500 µl) post dosing from the tail vein (detailed in Table 13 below). The weight of each rat was determined prior to sampling and used as an estimation of healthiness. At the point of termination the rats were sacrificed using the rising gradient of $CO_2$ followed by cervical dislocation.

Analysis of In Vivo Data

Bioanalysis was performed on a TSQ Endura (Thermoscientific) using a validated assay for emtricitabine in plasma. A calibration curve of emtricitabine was prepared in rat plasma via serial dilution, ranging from 1.9 to 500 ng/ml. Extraction was performed using protein precipitation. Linearity was then assessed by three independent preparations of the standard curve. Maximum allowed deviation of standards was set at 15% of the stated value, excluding the LLOQ where deviation was set at no more than 20%.

Inter and intra assay accuracy and precision was assessed by preparation of three concentrations (in the range of the standard curve 5, 200 and 400 ng/mL) with each preparation in triplicate. The mean value of each concentration was be within 15% of the stated concentration (except the lower concentration, where deviation was <20%).

Plasma concentrations of emtricitabine following administration of nanoparticle prodrugs were then plotted using GraphPad Prism (v7.0a) and pharmacokinetic parameters ($C_{max}$, $T_{max}$ and AUC) were calculated using the PKsolver plugin. The data can be seen in Table 13.

TABLE 13

| Prodrug nanoparticle | Prodrug compound | $C_{max}$ (ng/mL) | Cmin (ng/mL) | $AUC_{144}$ (ng/h/mL) | $T_{max}$ (h) |
|---|---|---|---|---|---|
| xiv | 8 | 2.36 | <2.00 | 170.50 | 72 |
| xii | 4 | 1.34 | <2.00 | 89.04 | 24 |
| xv | 4 | 1.57 | <2.00 | 86.00 | 24 |
| xvi | 6 | 19.83 | <2.00 | 802.34 | 24 |
| xiii | 8 | 6.04 | <2.00 | 305.90 | 48 |
| xi | 4 | 3.57 | <2.00 | 236.05 | 24 |
| xvii | 6 | 12.11 | <2.00 | 443.18 | 24 |
| xviii | 8 | 3.31 | <2.00 | 169.09 | 72 |
| xix | 6 | 42.8 | 22.116 | 3449.71 | 24 |
| xx | 8 | 33.96 | 24.075 | 3731.00 | 24 |
| xxi | 6 | 88.57 | 2.452 | 3960.91 | 24 |
| xxii | 8 | 47.1 | 16.867 | 3695.12 | 24 |

Table 14 below shows that solid prodrug nanoparticle compositions of the present invention demonstrated sustained release over 144 h. Solid prodrug nanoparticle compositions having polymer/surfactant combinations of HMPC/NDC and HMPC/AOT performed particularly well in the in vivo studies.

TABLE 14

| Prodrug nanoparticle | Emtricitabine concentration at 144 h (ng/mL) |
|---|---|
| xix | 22.12 |
| xx | 24.10 |
| xxii | 16.87 |

The invention claimed is:

1. A solid or semi-solid composition comprising nanoparticles of a prodrug compound of emtricitabine dispersed within one or more carrier materials, wherein the log P value of the prodrug compound is at least about 1 and greater than the log P value of emtricitabine, wherein the prodrug compound is selected from the group consisting of:

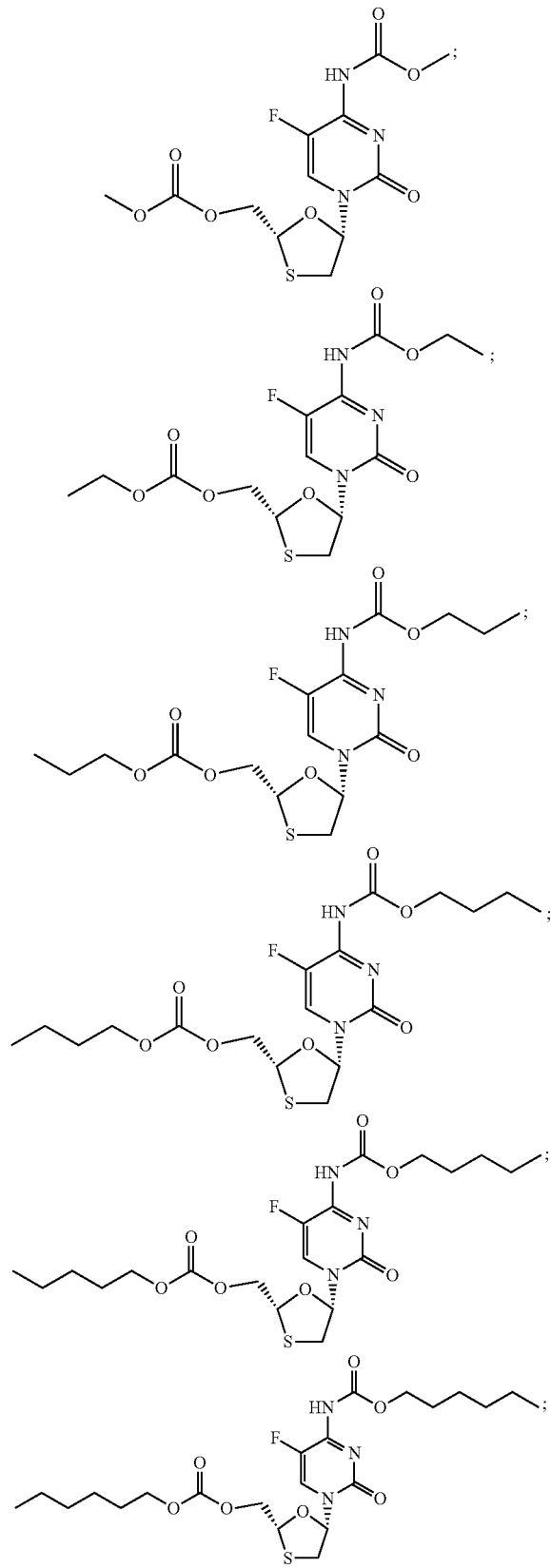

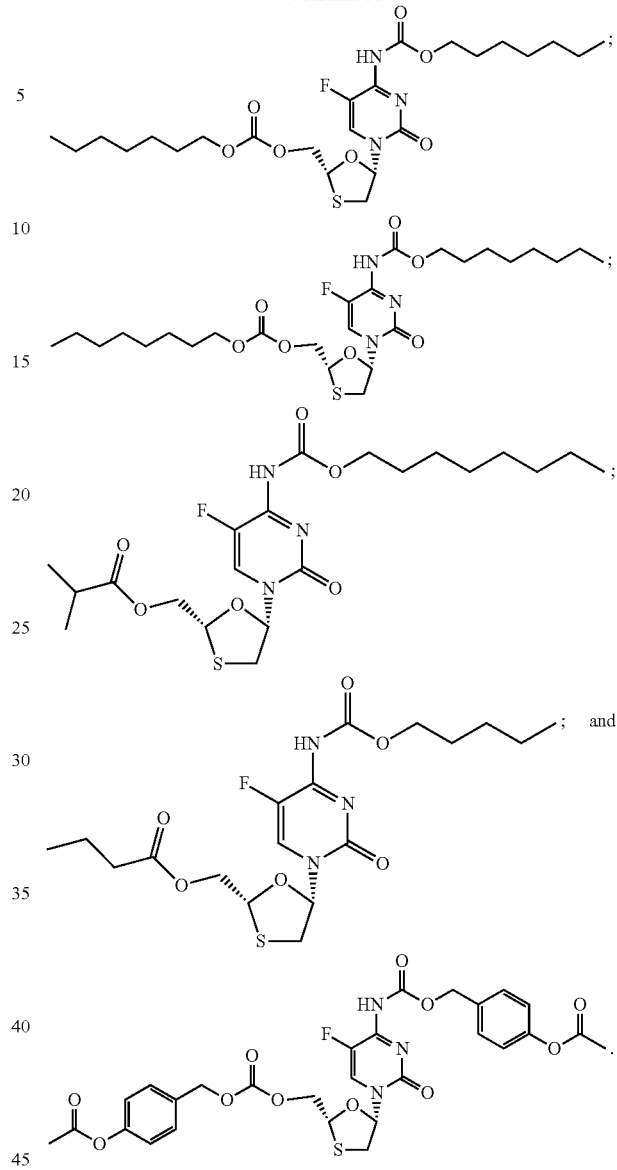

2. The composition of claim 1, wherein the one or more carrier materials comprise a hydrophilic polymer and/or surfactant.

3. The composition of claim 2, wherein the hydrophilic polymer is selected from the group consisting of ethylene oxide-propylene oxide block copolymers, polyvinyl alcohol ('PVA'), polyvinyl alcohol-polyethylene glycol graft copolymer; polyethylene glycol k1 (having average $M_w$ of 1,000), hydroxylpropyl methyl cellulose (HPMC), polyvinylpyrrolidone k30 ('PVP k30') and any combination thereof.

4. The composition of claim 2, wherein the surfactant is selected from the group consisting of vitamin-E-polyethylene glycol-succinate, sodium deoxycholate (NDC), polyoxyethylene (20) sorbitan monolaurate, polyoxyethylene (20) sorbitan monooleate, dioctyl sulfosuccinate sodium salt (AOT), polyethylene glycol (15)-hydroxystearate and any combination thereof.

5. The composition of claim 1, wherein the one or more carrier materials are provided in any one of the following combinations:

poloxamer 188 AND vitamin-E-polyethylene glycol-succinate;
poloxamer 188 AND sodium deoxycholate;
poloxamer 188 AND polyoxyethylene (20) sorbitan monolaurate;
poloxamer 188 AND polyoxyethylene (20) sorbitan monooleate;
poloxamer 188 AND dioctyl sulfosuccinate sodium salt;
poloxamer 188 AND polyethylene glycol (15)-hydroxystearate;
poloxamer 407 AND vitamin-E-polyethylene glycol-succinate;
poloxamer 407 AND sodium deoxycholate;
poloxamer 407 AND polyoxyethylene (20) sorbitan monolaurate;
poloxamer 407 AND polyoxyethylene (20) sorbitan monooleate;
poloxamer 407 AND dioctyl sulfosuccinate sodium salt;
poloxamer 407 AND polyethylene glycol (15)-hydroxystearate;
polyvinyl alcohol AND vitamin-E-polyethylene glycol-succinate;
polyvinyl alcohol AND sodium deoxycholate;
polyvinyl alcohol AND polyoxyethylene (20) sorbitan monolaurate;
polyvinyl alcohol AND polyoxyethylene (20) sorbitan monooleate;
polyvinyl alcohol AND dioctyl sulfosuccinate sodium salt;
polyvinyl alcohol-polyethylene glycol graft copolymer AND vitamin-E-polyethylene glycol-succinate;
polyvinyl alcohol-polyethylene glycol graft copolymer AND sodium deoxycholate;
polyvinyl alcohol-polyethylene glycol graft copolymer AND polyoxyethylene (20) sorbitan monolaurate;
polyvinyl alcohol-polyethylene glycol graft copolymer AND dioctyl sulfosuccinate sodium salt;
polyethylene glycol k1 AND sodium deoxycholate;
polyethylene glycol k1 AND polyoxyethylene (20) sorbitan monolaurate;
polyethylene glycol k1 AND polyoxyethylene (20) sorbitan monooleate;
polyethylene glycol k1 AND dioctyl sulfosuccinate sodium salt;
polyethylene glycol k1 AND polyethylene glycol (15)-hydroxystearate;
hydroxylpropyl methyl cellulose AND vitamin-E-polyethylene glycol-succinate;
hydroxylpropyl methyl cellulose AND sodium deoxycholate;
hydroxylpropyl methyl cellulose AND polyoxyethylene (20) sorbitan monolaurate;
hydroxylpropyl methyl cellulose AND polyoxyethylene (20) sorbitan monooleate;
hydroxylpropyl methyl cellulose AND dioctyl sulfosuccinate sodium salt;
hydroxylpropyl methyl cellulose AND polyethylene glycol (15)-hydroxystearate;
polyvinylpyrrolidone k30 AND vitamin-E-polyethylene glycol-succinate;
polyvinylpyrrolidone k30 AND sodium deoxycholate;
polyvinylpyrrolidone k30 AND polyoxyethylene (20) sorbitan monolaurate;
polyvinylpyrrolidone k30 AND polyoxyethylene (20) sorbitan monooleate;
polyvinylpyrrolidone k30 AND dioctyl sulfosuccinate sodium salt; or
polyvinylpyrrolidone k30 AND polyethylene glycol (15)-hydroxystearate.

6. The composition of claim 1, wherein the composition is a solid.

7. A process for preparing a composition according to claim 1, the process comprising:
(i) preparing an oil-in-water emulsion comprising:
an oil phase comprising a prodrug compound as defined in claim 1; and
an aqueous phase comprising one or more selected carrier materials, wherein the one or more carrier materials comprise a hydrophilic polymer and/or surfactant; and
(ii) removing the oil and water from the oil-in-water emulsion to form the composition.

8. A process for preparing a composition according to claim 1, the process comprising:
(i) preparing a single phase solution comprising a prodrug compound as defined in claim 1, and one or more selected carrier materials, wherein the one or more carrier materials comprise a hydrophilic polymer and/or surfactant, in one or more solvents; and
(ii) removing the one or more solvents to form the solid composition.

9. A pharmaceutical or veterinary composition in injectable form comprising a composition according to claim 1, and optionally one or more additional (pharmaceutically acceptable) excipients.

10. An intramuscularly-injectable formulation of nanoparticles of a prodrug compound as defined in claim 1.

11. A subcutaneously-injectable formulation of nanoparticles of a prodrug compound as defined in claim 1.

12. An aqueous dispersion, comprising a plurality of nanoparticles of a prodrug compound as defined in claim 1 dispersed in an aqueous medium, each nanoparticle of the prodrug compound being a core around at least some of which an outer layer composed of one or more carrier materials is provided, wherein the prodrug is present in a concentration of at least 10 mg/mL.

13. An oily dispersion, comprising a plurality of nanoparticles of a prodrug compound as defined in claim 1 and one or more carrier materials dispersed in an oily medium, wherein the prodrug is present in a concentration of at least 10 mg/mL.

14. A method of treating an HIV infection, the method comprising administering a therapeutically effect amount of a composition according to claim 1, or an injectable pharmaceutical or veterinary composition thereof.

15. A prodrug compound selected from any one of the following formulae:
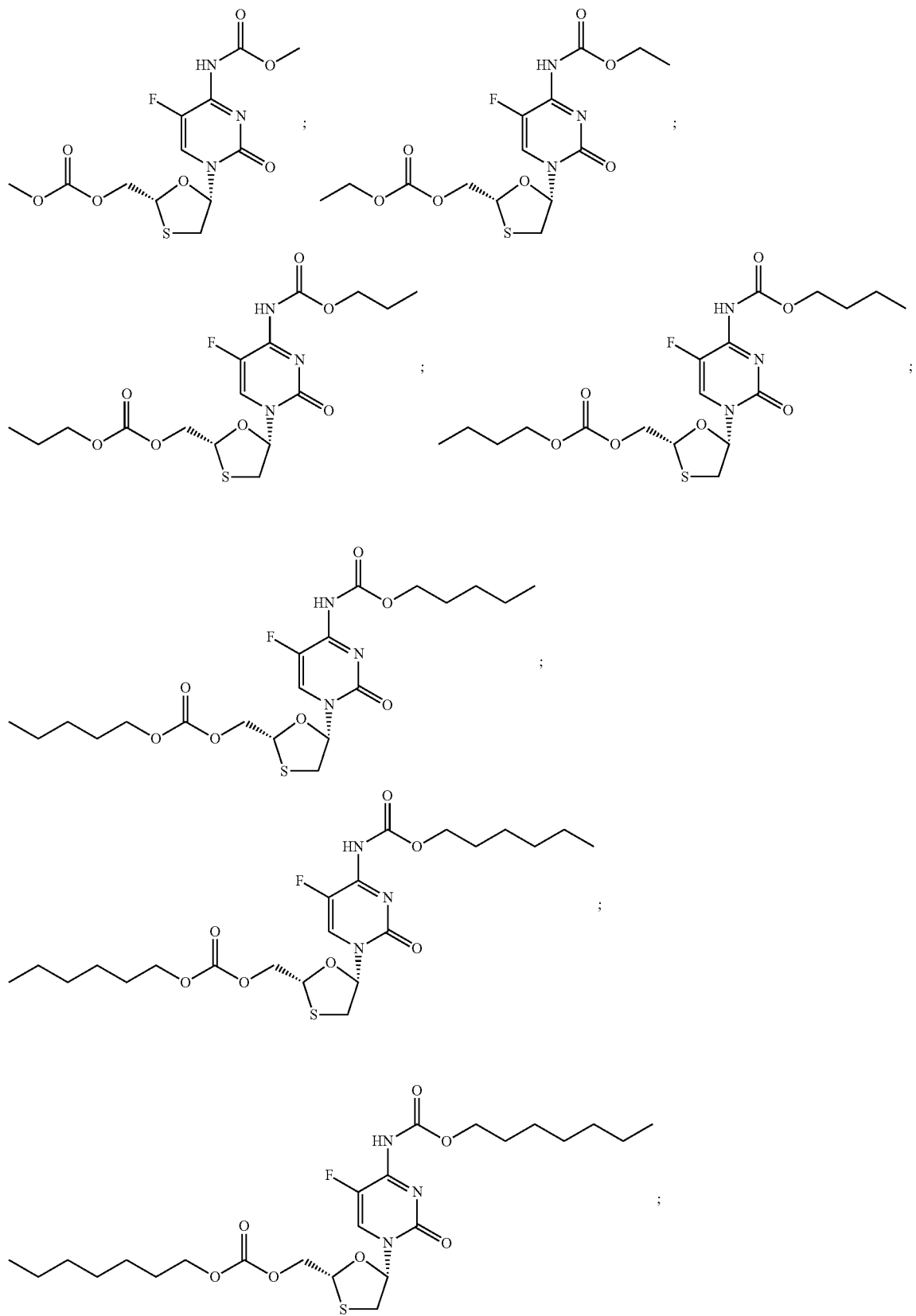

-continued

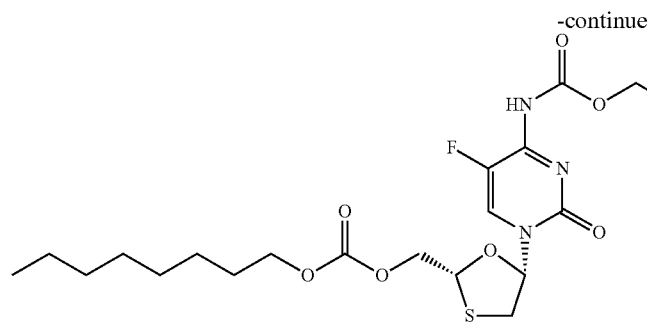

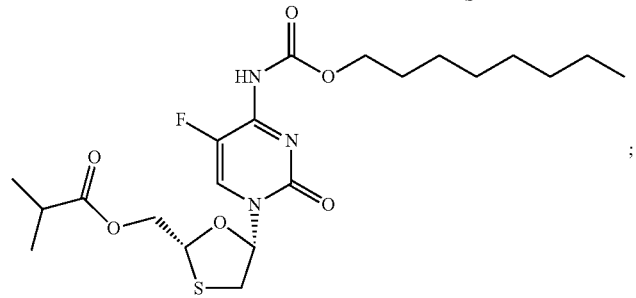

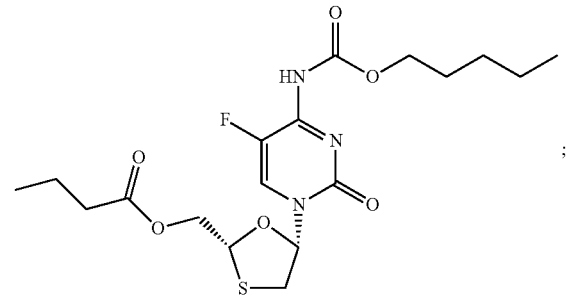

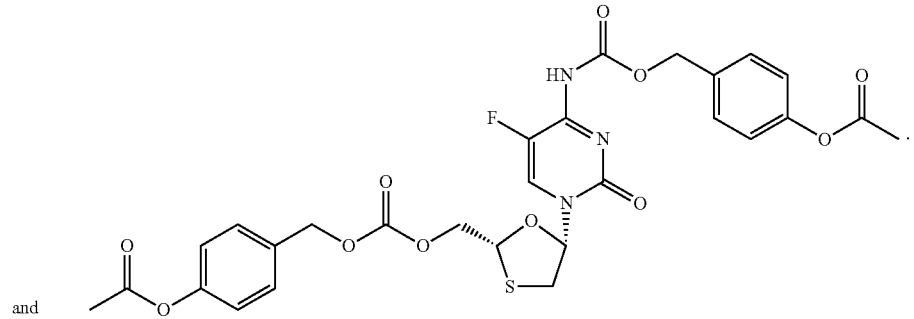 [SMILES: CC(=O)Oc1ccc(COC(=O)Nc2nc(=O)n([C@@H]3CS[C@H](COC(=O)OCc4ccc(OC(C)=O)cc4)O3)cc2F)cc1]

and

16. A method of treating an HIV infection, the method comprising administering a therapeutically effect amount of a prodrug compound according to claim 15.

17. A method of treating an HIV infection, the method comprising administering a therapeutically effect amount of a formulation of nanoparticles of the prodrug according to claim 1;
wherein the formulation of nanoparticles is an intramuscularly-injectable formulation, a subcutaneously-injectable formulation, an aqueous dispersion, or an oily dispersion,
wherein the aqueous dispersion comprises a plurality of nanoparticles of the prodrug compound dispersed in an aqueous medium, each nanoparticle of the prodrug compound being a core around at least some of which an outer layer composed of one or more carrier materials is provided, wherein the prodrug is present in a concentration of at least 10 mg/mL;
wherein the oily dispersion comprises a plurality of nanoparticles of the prodrug compound and one or more carrier materials dispersed in an oily medium, wherein the prodrug is present in a concentration of at least 10 mg/mL.

18. The composition of claim 1, wherein the composition is a semi-solid.

* * * * *